(12) United States Patent
Deck et al.

(10) Patent No.: US 12,396,726 B2
(45) Date of Patent: Aug. 26, 2025

(54) CLAMPING ASSEMBLY FOR LINEAR SURGICAL STAPLER

(71) Applicant: Cilag GmbH International, Zug (CH)

(72) Inventors: Andrew C. Deck, Cincinnati, OH (US); Brian D. Schings, Maineville, OH (US); Jason D. Jones, Cincinnati, OH (US); Gregory J. Bakos, Mason, OH (US); David K. Norvell, Monroe, OH (US); Christopher J. Schall, Mason, OH (US); Joshua Uth, Mason, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 197 days.

(21) Appl. No.: 17/671,843

(22) Filed: Feb. 15, 2022

(65) Prior Publication Data

US 2022/0225987 A1    Jul. 21, 2022

Related U.S. Application Data

(63) Continuation of application No. 16/102,170, filed on Aug. 13, 2018, now Pat. No. 11,278,285.

(51) Int. Cl.
*A61B 17/072* (2006.01)

(52) U.S. Cl.
CPC ............ *A61B 17/07207* (2013.01); *A61B 2017/07228* (2013.01); *A61B 2017/07257* (2013.01); *A61B 2017/07271* (2013.01)

(58) Field of Classification Search
CPC .... A61B 17/07207; A61B 2017/07228; A61B 2017/07257; A61B 2017/07271; A61B 2017/00477; A61B 2017/0725
(Continued)

(56) References Cited

U.S. PATENT DOCUMENTS 2,066,157 A    12/1936  Pankonin
2,083,227 A    6/1937   Drypolcher
(Continued)

FOREIGN PATENT DOCUMENTS

CN    104490437 A    4/2015
CN    104739472 A    7/2015
(Continued)

OTHER PUBLICATIONS

Brazil Office Action dated Jun. 1, 2023, for Application No. BR112021002623-1, 4 pages.
(Continued)

*Primary Examiner* — Robert F Long
(74) *Attorney, Agent, or Firm* — FROST BROWN TODD LLP

(57) ABSTRACT

A surgical stapler includes a first elongate member having a distal portion that supports an anvil surface, and a second elongate member having a distal portion configured to receive a staple cartridge. The stapler further includes a pin rotatably coupled with the first elongate member, and a clamp member movably coupled with the second elongate member. The clamp member is operable to releasably capture the pin to thereby clamp the first elongate member against the second elongate member. The pin is configured to rotate relative to the first elongate member in response to being captured by the clamp member.

17 Claims, 39 Drawing Sheets

(58) Field of Classification Search
USPC .......................................... 227/175.1–182.1
See application file for complete search history.

(56) References Cited

U.S. PATENT DOCUMENTS

| | | |
|---|---|---|
| 2,311,412 A | 2/1943 | Pankonin |
| 2,469,984 A | 5/1949 | Pankonin |
| 2,939,146 A | 6/1960 | Abrams |
| 2,946,059 A | 7/1960 | Wandel |
| 4,047,654 A | 9/1977 | Alvarado |
| 4,180,196 A | 12/1979 | Hueil et al. |
| 4,312,363 A | 1/1982 | Rothfuss et al. |
| 4,354,628 A | 10/1982 | Green |
| 4,453,661 A | 6/1984 | Genyk et al. |
| 4,506,819 A | 3/1985 | Rand |
| 4,520,817 A | 6/1985 | Green |
| 4,522,327 A | 6/1985 | Korthoff et al. |
| 4,580,712 A * | 4/1986 | Green .................. A61B 17/072 227/19 |
| 4,608,981 A | 9/1986 | Rothfuss et al. |
| 4,878,608 A | 11/1989 | Mitsuhashi |
| 4,930,674 A | 6/1990 | Barak |
| 4,984,729 A | 1/1991 | Balma |
| 4,991,764 A | 2/1991 | Mericle |
| 5,071,052 A | 12/1991 | Rodak et al. |
| 5,074,454 A | 12/1991 | Peters |
| 5,137,198 A * | 8/1992 | Nobis .................. A61B 17/072 227/175.3 |
| 5,141,144 A | 8/1992 | Foslien |
| 5,180,092 A | 1/1993 | Crainich |
| 5,183,196 A | 2/1993 | Miyashita |
| 5,190,203 A * | 3/1993 | Rodak .................. A61B 17/072 227/19 |
| 5,312,023 A | 5/1994 | Green et al. |
| 5,337,937 A | 8/1994 | Remiszewski et al. |
| 5,389,098 A | 2/1995 | Tsuruta et al. |
| 5,395,034 A | 3/1995 | Allen et al. |
| 5,445,304 A * | 8/1995 | Plyley .................. A61B 17/07207 227/176.1 |
| 5,465,894 A | 11/1995 | Clark et al. |
| 5,489,058 A | 2/1996 | Plyley et al. |
| 5,533,521 A | 7/1996 | Granger |
| 5,551,622 A | 9/1996 | Yoon |
| 5,571,090 A | 11/1996 | Sherts |
| 5,636,779 A | 6/1997 | Palmer |
| 5,749,893 A | 5/1998 | Vidal et al. |
| 5,792,135 A | 8/1998 | Madhani et al. |
| 5,792,165 A | 8/1998 | Klieman et al. |
| 5,817,084 A | 10/1998 | Jensen |
| 5,878,193 A | 3/1999 | Wang et al. |
| 5,893,506 A * | 4/1999 | Powell .................. A61B 17/07207 227/176.1 |
| 5,988,479 A | 11/1999 | Palmer |
| 6,152,347 A | 11/2000 | Wilson et al. |
| 6,231,565 B1 | 5/2001 | Tovey et al. |
| 6,364,888 B1 | 4/2002 | Niemeyer et al. |
| 6,783,524 B2 | 8/2004 | Anderson et al. |
| 7,032,799 B2 | 4/2006 | Viola et al. |
| 7,296,722 B2 | 11/2007 | Ivanko |
| 7,334,717 B2 * | 2/2008 | Rethy .................. A61B 17/105 227/175.3 |
| 7,524,320 B2 | 4/2009 | Tierney et al. |
| 7,568,604 B2 | 8/2009 | Ehrenfels et al. |
| 7,691,098 B2 | 4/2010 | Wallace et al. |
| 7,806,891 B2 | 10/2010 | Nowlin et al. |
| 7,905,381 B2 | 3/2011 | Baxter, III et al. |
| 7,954,686 B2 | 6/2011 | Baxter, III et al. |
| 8,348,129 B2 | 1/2013 | Bedi et al. |
| 8,365,971 B1 | 2/2013 | Knodel |
| 8,479,969 B2 | 7/2013 | Shelton, IV |
| 8,523,041 B2 | 9/2013 | Ishitsuki et al. |
| 8,561,870 B2 | 10/2013 | Baxter, III et al. |
| 8,573,461 B2 | 11/2013 | Shelton, IV et al. |
| 8,573,465 B2 | 11/2013 | Shelton, IV |
| 8,602,288 B2 | 12/2013 | Shelton, IV et al. |
| 8,616,431 B2 | 12/2013 | Timm et al. |
| 8,783,541 B2 | 7/2014 | Shelton, IV et al. |
| 8,789,740 B2 | 7/2014 | Baxter, III et al. |
| 8,800,838 B2 | 8/2014 | Shelton, IV |
| 8,820,605 B2 | 9/2014 | Shelton, IV |
| 8,844,789 B2 | 9/2014 | Shelton, IV et al. |
| 8,998,061 B2 * | 4/2015 | Williams ............. A61B 17/068 227/176.1 |
| 9,155,537 B2 | 10/2015 | Katre et al. |
| 9,161,807 B2 | 10/2015 | Garrison |
| 9,301,759 B2 | 4/2016 | Spivey et al. |
| 9,402,629 B2 | 8/2016 | Ehrenfels et al. |
| 9,451,959 B2 | 9/2016 | Patankar et al. |
| 9,539,007 B2 | 1/2017 | Dhakad et al. |
| 9,724,095 B2 | 8/2017 | Gupta et al. |
| 9,987,007 B2 | 6/2018 | Kapadia |
| 10,512,461 B2 | 12/2019 | Gupta et al. |
| 10,631,866 B2 | 4/2020 | Laurent et al. |
| 10,667,818 B2 | 6/2020 | McLain et al. |
| 10,687,819 B2 | 6/2020 | Stokes et al. |
| 10,874,398 B2 | 12/2020 | Baxter, III et al. |
| 10,898,187 B2 | 1/2021 | Deck et al. |
| 10,898,197 B2 | 1/2021 | Baxter, III et al. |
| 10,905,419 B2 | 2/2021 | Schings et al. |
| 10,932,781 B2 | 3/2021 | Jones et al. |
| 11,033,266 B2 | 6/2021 | Jones et al. |
| 11,045,193 B2 | 6/2021 | Schings et al. |
| 11,278,285 B2 | 3/2022 | Deck et al. |
| 2002/0005427 A1 | 1/2002 | Aoki |
| 2004/0267311 A1 | 12/2004 | Viola et al. |
| 2005/0222616 A1 * | 10/2005 | Rethy .................. A61B 17/105 606/215 |
| 2006/0231583 A1 | 10/2006 | Kumayama |
| 2008/0142565 A1 * | 6/2008 | Ehrenfels ......... A61B 17/07207 227/176.1 |
| 2008/0167680 A1 | 7/2008 | Voegele et al. |
| 2008/0188844 A1 * | 8/2008 | McGreevy ........... A61B 18/082 606/28 |
| 2009/0078739 A1 * | 3/2009 | Viola ............... A61B 17/07292 227/180.1 |
| 2009/0209986 A1 | 8/2009 | Stewart et al. |
| 2009/0302093 A1 | 12/2009 | Kasvikis |
| 2009/0308907 A1 | 12/2009 | Nalagatla et al. |
| 2009/0308909 A1 | 12/2009 | Nalagatla et al. |
| 2010/0072253 A1 | 3/2010 | Baxter, III et al. |
| 2010/0213241 A1 | 8/2010 | Bedi |
| 2010/0282820 A1 * | 11/2010 | Kasvikis ............... A61B 17/068 227/181.1 |
| 2010/0288815 A1 | 11/2010 | Maemori |
| 2011/0084115 A1 | 4/2011 | Bedi et al. |
| 2011/0087276 A1 * | 4/2011 | Bedi ................ A61B 17/07207 227/175.1 |
| 2011/0226837 A1 | 9/2011 | Baxter, III et al. |
| 2011/0257679 A1 | 10/2011 | Ishitsuki et al. |
| 2011/0278343 A1 | 11/2011 | Knodel et al. |
| 2011/0290851 A1 * | 12/2011 | Shelton, IV ..... A61B 17/07207 227/176.1 |
| 2012/0024936 A1 * | 2/2012 | Baxter, III ........ A61B 17/07207 227/180.1 |
| 2012/0248169 A1 * | 10/2012 | Widenhouse ...... A61B 17/0644 227/175.1 |
| 2012/0312858 A1 * | 12/2012 | Patankar .......... A61B 17/07207 227/176.1 |
| 2012/0312859 A1 * | 12/2012 | Gupta .............. A61B 17/07207 227/176.1 |
| 2013/0037595 A1 | 2/2013 | Gupta et al. |
| 2013/0037597 A1 * | 2/2013 | Katre ................. A61B 17/0686 227/176.1 |
| 2013/0140343 A1 * | 6/2013 | Knodel ................ A61B 17/068 227/176.1 |
| 2013/0306703 A1 | 11/2013 | Ehrenfels et al. |
| 2014/0200580 A1 | 7/2014 | Joseph et al. |
| 2014/0239037 A1 * | 8/2014 | Boudreaux ...... A61B 17/07207 227/175.1 |
| 2014/0353357 A1 | 12/2014 | Agarwal et al. |
| 2015/0018875 A1 | 1/2015 | Knodel |
| 2015/0034695 A1 | 2/2015 | Kapadia |
| 2015/0066022 A1 | 3/2015 | Shelton, IV et al. |

(56) References Cited

U.S. PATENT DOCUMENTS

| | | | |
|---|---|---|---|
| 2015/0282866 A1* | 10/2015 | Rothweiler | A61B 18/1445 |
| | | | 606/51 |
| 2015/0327855 A1 | 11/2015 | Katre | |
| 2016/0135811 A1 | 5/2016 | Gupta et al. | |
| 2016/0199084 A1* | 7/2016 | Takei | A61B 17/295 |
| | | | 606/170 |
| 2016/0213377 A1 | 7/2016 | Shankarsetty et al. | |
| 2016/0249920 A1 | 9/2016 | Gupta et al. | |
| 2016/0262756 A1 | 9/2016 | Patankar et al. | |
| 2016/0310136 A1 | 10/2016 | Gupta et al. | |
| 2016/0338701 A1 | 11/2016 | Patankar et al. | |
| 2016/0338702 A1 | 11/2016 | Ehrenfels et al. | |
| 2017/0079652 A1 | 3/2017 | Dhakad et al. | |
| 2017/0095251 A1* | 4/2017 | Thompson | A61F 5/0089 |
| 2017/0143335 A1 | 5/2017 | Gupta et al. | |
| 2017/0143336 A1 | 5/2017 | Shah et al. | |
| 2017/0325811 A1 | 11/2017 | Gupta et al. | |
| 2018/0015767 A1 | 1/2018 | Kim | |
| 2018/0221102 A1 | 8/2018 | Wang et al. | |
| 2018/0296213 A1 | 10/2018 | Strobl | |
| 2018/0317915 A1 | 11/2018 | McDonald, II | |
| 2019/0239881 A1* | 8/2019 | Laurent | A61B 17/115 |
| 2019/0239882 A1* | 8/2019 | McLain | A61B 17/1114 |
| 2019/0239885 A1* | 8/2019 | Stokes | A61B 17/115 |
| 2020/0046350 A1* | 2/2020 | Deck | A61B 17/07207 |
| 2020/0046353 A1* | 2/2020 | Deck | A61B 17/07207 |
| 2020/0223045 A1 | 7/2020 | Young et al. | |
| 2020/0405298 A1* | 12/2020 | Ding | A61B 17/07207 |
| 2021/0369270 A1* | 12/2021 | Schings | A61B 17/07207 |
| 2023/0397911 A1* | 12/2023 | Deck | A61B 17/115 |

FOREIGN PATENT DOCUMENTS

| | | |
|---|---|---|
| EP | 0061466 A1 | 10/1982 |
| EP | 0178941 B1 | 4/1986 |
| EP | 0677273 B1 | 10/1995 |
| EP | 1702567 B1 | 9/2006 |
| EP | 2532312 B1 | 12/2012 |
| EP | 2804541 A | 11/2014 |
| EP | 3065649 A1 | 9/2016 |
| EP | 2741685 B1 | 1/2017 |
| EP | 3155988 A1 | 4/2017 |
| EP | 2804541 B1 | 10/2017 |
| JP | H06-26812 U | 4/1994 |
| JP | H10-24742 A | 1/1998 |
| JP | 2004-140395 A | 5/2004 |
| WO | WO 2013/109445 A2 | 7/2013 |
| WO | WO 2017/056028 A1 | 4/2017 |
| WO | WO 2018/044669 A1 | 3/2018 |

OTHER PUBLICATIONS

European Search Report, partial, and Provisional Written Opinion dated Dec. 2, 2019, for Application No. 19191305.2, 16 pages.

European Search Report, Extended, and Written Opinion dated Feb. 28, 2020, for Application No. 19191305.2, 21 pages.

European Communication dated Apr. 28, 2023, for Application No. 19191305.2, 6 pages.

Indian Office Action dated Oct. 12, 2022, for Application No. 202117004565, 7 pages.

International Search Report and Written Opinion dated Feb. 28, 2020, for International Application No. PCT/IB2019/056698, 23 pages.

Japanese Notification of Reasons for Refusal dated May 30, 2023, for Application No. 2021-507549, 7 pages.

Japanese first Office Action dated Jul. 9, 2024, for Application No. 2023-175839, 9 pages.

* cited by examiner

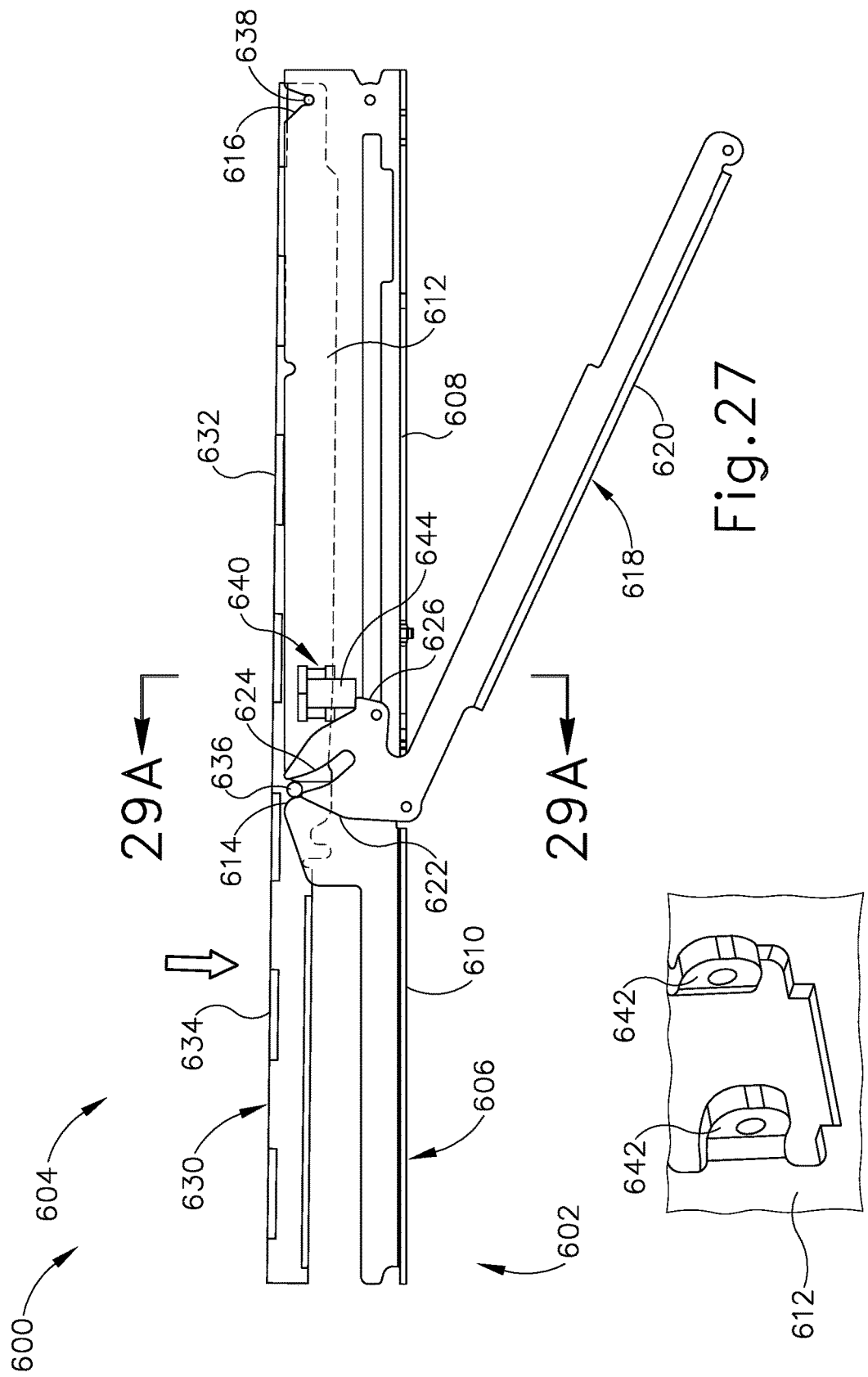

CLAMPING ASSEMBLY FOR LINEAR SURGICAL STAPLER

This application is a continuation of U.S. patent application Ser. No. 16/102,170, entitled "Clamping Assembly for Linear Surgical Stapler," filed Aug. 13, 2018 and issued as U.S. Pat. No. 11,278,285 on Mar. 22, 2022.

BACKGROUND

In some surgical operations, such as a gastrointestinal anastomosis, it may be desirable to clamp down on one or more layers of tissue, cut through the clamped layers, and simultaneously drive staples through the layers to substantially seal the severed layers of tissue together near their severed ends. One such instrument that may be used in such operations is a linear surgical stapler, also referred to as a "linear cutter." A linear surgical stapler generally includes a first half (referred to as a "cartridge half" or "reload half") having a distal jaw configured to support a staple cartridge (or "reload"), and a second half (referred to as an "anvil half") having a distal jaw that supports an anvil surface having staple forming features. The stapler further includes a moveable clamp lever configured to releasably clamp the stapler halves together. The stapler halves are configured to pivot relative to one another to receive and clamp tissue between the two distal jaws when the clamp lever is closed. A firing assembly of the stapler is configured to be actuated to cut the clamped layers and simultaneously drive staples through the tissue on either side of the cut line. After firing the stapler, the clamp lever may be opened and the stapler halves separated to release the severed and stapled tissue.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 27 depicts a side elevational view of another exemplary linear surgical stapler, with shrouds of the stapler being omitted to reveal details of a clamp lever lockout member, showing the clamp lever locked out in an open position;

FIG. 28 depicts an enlarged perspective view of a support structure for the clamp lever lockout member of FIG. 27;

Figure 1:
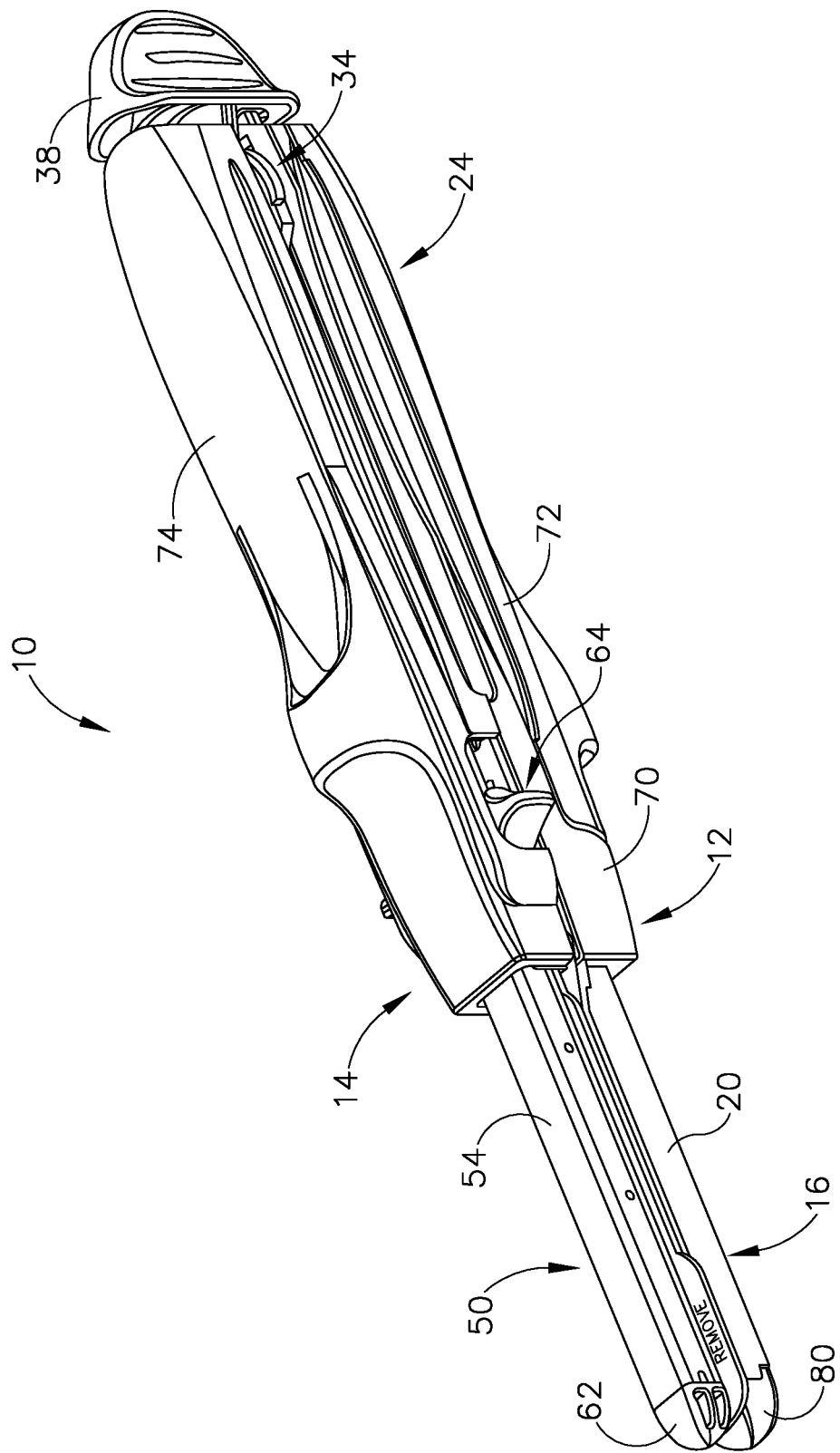
FIG. 1 depicts a distal perspective view of an exemplary linear surgical stapler, showing a cartridge half and an anvil half of the stapler coupled together with a clamp lever of the cartridge half in a fully closed position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about" and "approximately" for any numerical values or ranges indicate a suitable dimensional tolerance that allows the part or collection of components to function for its intended purpose as described herein.

I. Exemplary Linear Surgical Stapler

A. Overview of Linear Surgical Stapler

Figure 2:
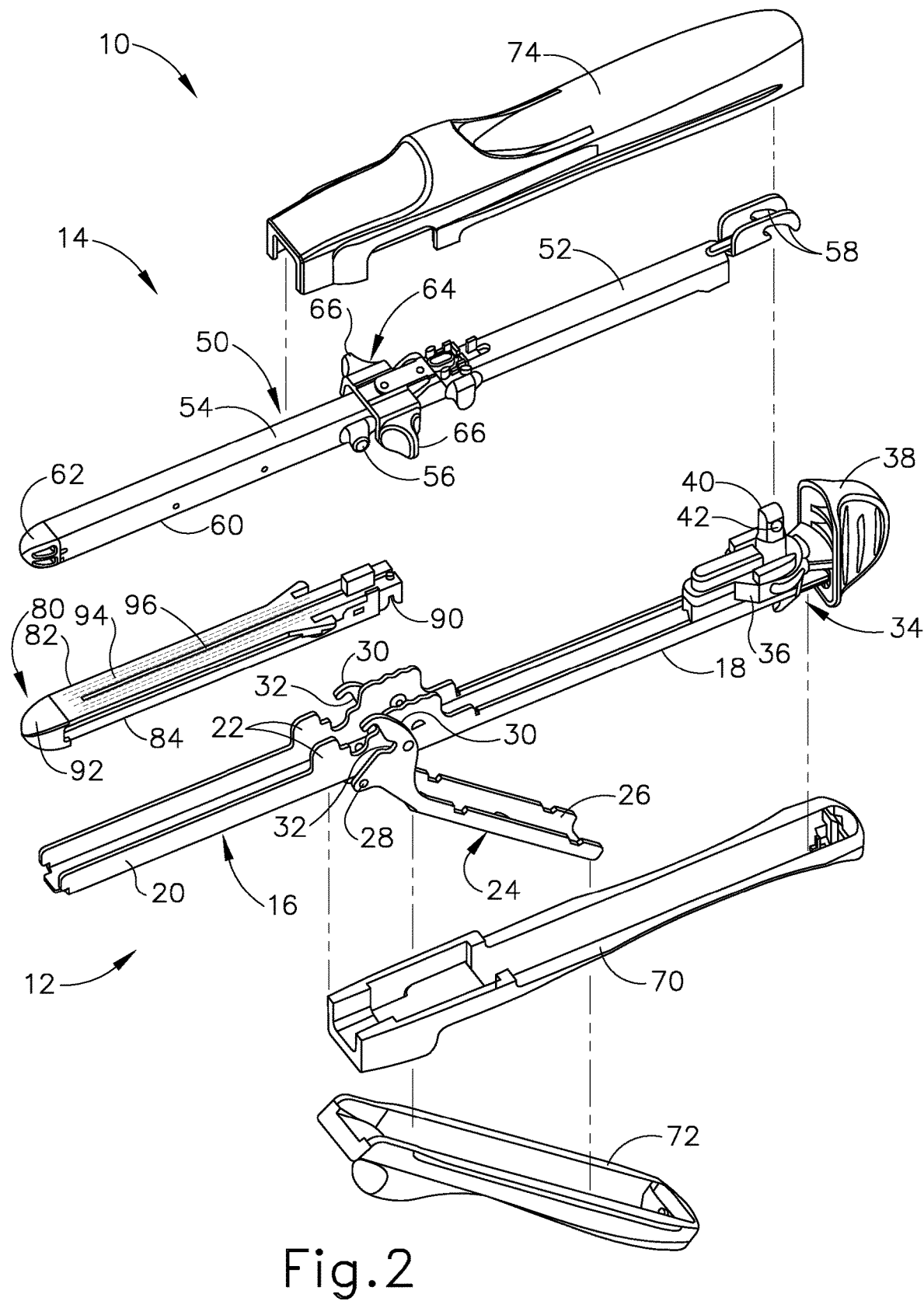
FIG. 2 depicts an exploded perspective view of the linear surgical stapler of FIG. 1.

FIGS. 1 and 2 show an exemplary linear surgical stapler (10) (also referred to as a "linear cutter") suitable for use in a variety of cutting and stapling procedures, such as a gastrointestinal anastomosis procedure. Linear surgical stapler (10) includes a cartridge half (12) (also referred to as a "reload half") and an anvil half (14) configured to releasably couple together to clamp tissue therebetween. Cartridge half (12) includes an elongate cartridge channel (16) having a proximal frame portion (18) that slidably retains a portion of a firing assembly (34), a distal jaw portion (20) that supports a staple cartridge (80) (or "reload"), and a pair of upright side flanges (22) arranged medially therebetween.

Cartridge half (12) further includes a clamp lever (24) pivotably coupled to an underside of cartridge channel (16) in approximate alignment with side flanges (22). Clamp lever (24) includes an elongate lever arm (26) having a free proximal end and a distal end that is pivotably coupled to cartridge channel (16) with a pivot pin (28). A pair of opposed jaws (30) extends distally from the distal end of lever arm (26) alongside flanges (22) of cartridge channel (16). Each jaw (30) includes a respective elongate slot (32) having a closed proximal end and an open distal end, and which defines upper and lower camming surfaces configured to engage a respective latch projection (56) of anvil half (14). As described below, clamp lever (24) is operable to pivot relative to cartridge channel (16) between open and closed positions to releasably clamp anvil half (14) against cartridge half (12) and thereby capture tissue layers therebetween.

As shown best in FIG. 2, firing assembly (34) of cartridge half (12) includes a slider block (36) slidably retained within proximal frame portion (18) of cartridge channel (16), an actuator (38) (or "firing knob") movably coupled with slider block (36), and an elongate actuating beam (not shown) extending distally from slider block (36) and configured to couple with a sled (100) (see FIG. 3) housed within staple cartridge (80). Actuator (38) of the present example is configured to pivot about the proximal end of cartridge half (12) to provide for "dual-sided firing" of stapler (10). Specifically, actuator (38) may be positioned along either lateral side of cartridge half (12) to perform a distal firing stroke, such that stapler (10) may be conveniently fired in a variety of orientations during a surgical procedure.

Figure 5A:
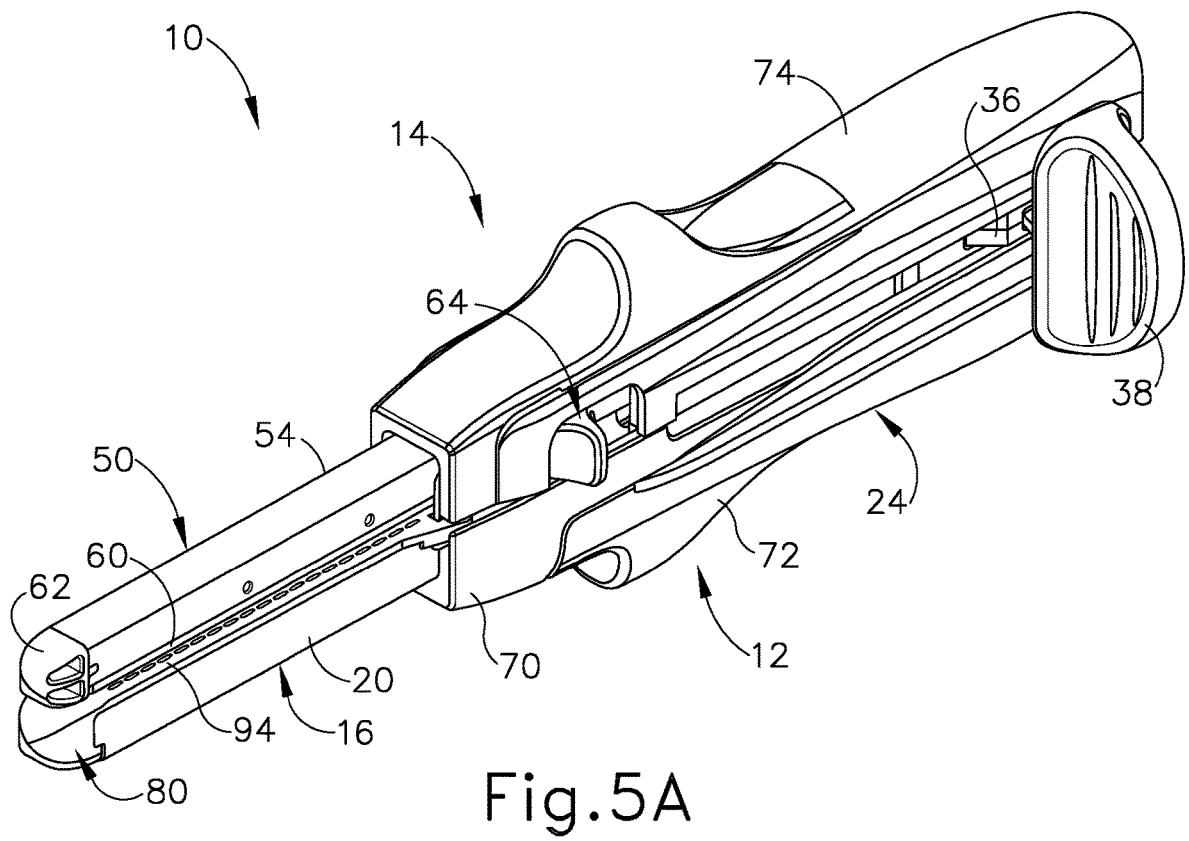
FIG. 5A depicts a distal perspective view of the linear surgical stapler of FIG. 1, showing an actuator of the stapler in a proximal, pre-fired position.
Figure 5B:
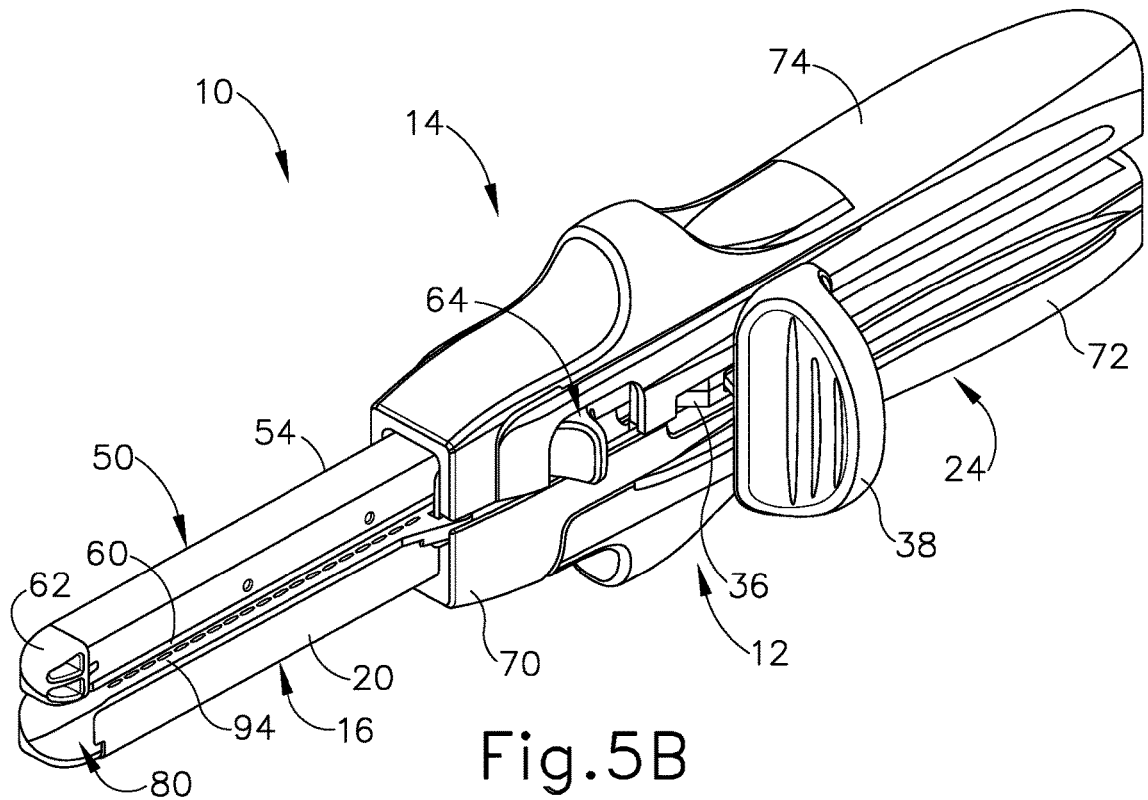
FIG. 5B depicts a distal perspective view of the linear surgical stapler of FIG. 1, showing the actuator in a distal, fired position.

Slider block (36) is configured to be translatably driven within proximal frame portion (18) by actuator (38) between a proximal home position shown in FIGS. 2 and 5A, and a distal fired position shown in FIG. 5B. In the proximal home position, slider block (36) abuts a post (40) fixed at a proximal end of cartridge channel (16). A free end of post (40) supports a laterally extending pivot pin (42). As described below, actuator (38) may be driven distally when stapler halves (12, 14) are fully coupled together and clamp lever (24) is closed. Distal advancement of actuator (38) along either lateral side of stapler (10) drives slider block (36) and the elongate actuating beam distally, which in turn drives sled (100) distally through staple cartridge (80). As described below, distal translation of sled (100) through staple cartridge (80) provides for simultaneous stapling and cutting of tissue clamped between stapler halves (12, 14).

As shown best in FIGS. 1 and 2, anvil half (14) of linear surgical stapler (10) includes an elongate anvil channel (50) having a proximal frame portion (52) and a distal jaw portion (54). Anvil channel (50) further includes a latch feature in the form of a pair of projections (56) that extend transversely from a medial portion of anvil channel (50) in a direction toward cartridge half (12). Each latch projection (56) may include a circular rotating cap configured to be captured within the slot (32) of a respective clamp lever jaw (30) when anvil half (14) is coupled with cartridge half (12) and clamp lever (24) is pivoted from the open position to the closed position, as described below. A pair of hooks (58) extend proximally from a proximal end of frame portion (52) and are configured to releasably capture opposed lateral ends of proximal pivot pin (42) of cartridge half (12). Distal jaw portion (54) supports an anvil surface in the form of an anvil plate (60) having a plurality of staple forming pockets (not shown), and additionally supports a distal tip member (62). In other versions of stapler (10), the anvil surface may be formed integrally with or otherwise be rigidly connected to distal jaw portion (54) of anvil channel (50).

Anvil half (14) of the present example further includes a staple height adjustment mechanism (64) mounted to a medial portion of anvil channel (50). Staple height adjustment mechanism (64) is operatively coupled with anvil plate (60), for example via one or more camming features (not shown), and includes a pair of user-engageable projections (66). Longitudinal adjustment of projections (66) between a plurality of predetermined positions causes anvil plate (60) to move transversely relative to distal jaw portion (54) of anvil channel (50). This enables adjustment of a transverse gap distance between anvil plate (60) and a deck (94) of staple cartridge (80) that defines the height of staples being formed. A larger gap distance, and thus a greater staple height, may be set when stapling tissues of greater thicknesses. Conversely, a smaller gap distance, and thus a smaller staple height, may be set when stapling tissues of lesser thicknesses. It will be appreciated that staple height adjustment mechanism (64) may be omitted in some versions, in which case the anvil surface may be fixed relative to anvil channel (50). For instance, the anvil surface may be formed integrally with or otherwise fixedly secured to distal jaw portion (54).

As shown best in in FIGS. 1 and 2, linear surgical stapler (10) further includes a plurality of shrouds (70, 72, 74) that cover select portions of stapler (10) and promote effective grip and manipulation of stapler (10) by an operator during use. In the present example, cartridge half (12) includes a first shroud (70) that covers an outwardly facing side of proximal frame portion (18) of cartridge channel (16). Cartridge half (12) further includes a second shroud (72) that covers an outwardly facing side of clamp lever (24) and is configured to pivot with clamp lever (24) relative to cartridge channel (16) and first shroud (70). Anvil half (14) includes a third shroud (74) that covers an outwardly facing side of proximal frame portion (52) of anvil channel (50), including proximal hooks (58). Each shroud (70, 72, 74) may be coupled with its respective components of stapler (10) by any suitable means apparent to those of ordinary skill in the art. Additionally, each shroud (70, 72, 74) may be formed of one or more materials and be provided with texturing suitable to promote effective gripping of the shroud (70, 72, 74) by an operator to enable safe and efficient use of stapler (10) during a surgical procedure.

Figure 3:
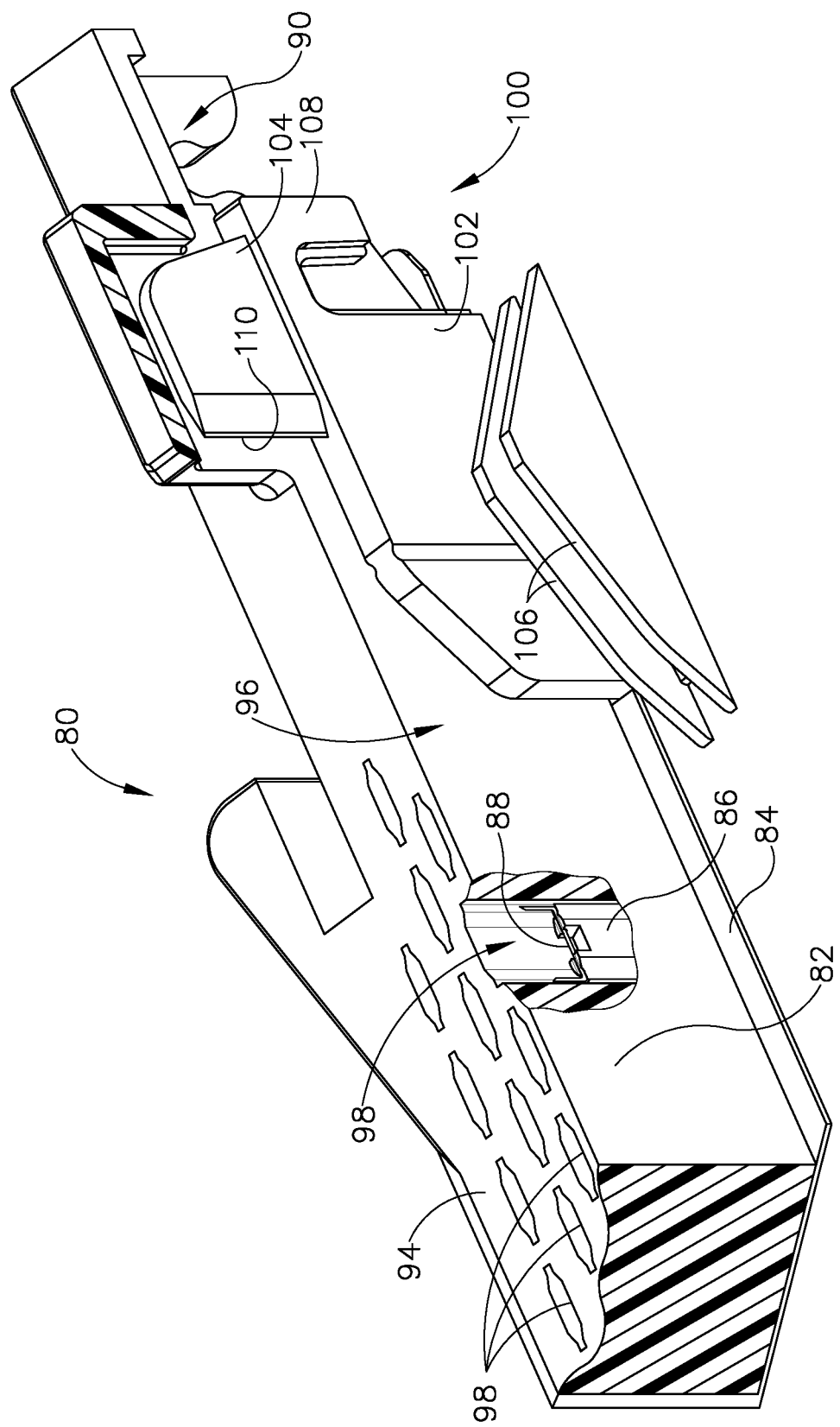
FIG. 3 depicts a cross-sectional perspective view of a staple cartridge assembly of the linear surgical stapler of FIG. 1.

As shown in FIGS. 2 and 3, staple cartridge (80) of the present example is an assembly that comprises a cartridge body (82), a pan (84) that covers an open lower side of cartridge body (82), and a plurality of staple drivers (86) housed within cartridge body (82) and each being configured to drive a respective staple (88). Cartridge body (82) includes a proximal end having coupling features (90) configured to releasably engage corresponding coupling features (not shown) of distal jaw portion (20) of cartridge channel (16), and a distal end defining a tapered nose (92). An upper side of cartridge body (82) defines a generally planar deck (94) through which a longitudinal slot (96) and a plurality of staple cavities (98) open. Each staple cavity (98) houses a respective staple driver (86) and a staple (88). As shown in FIG. 3, an interior of cartridge body (82) slidably houses a sled (100) that comprises a sled body (102) and knife member (104). Lateral sides of sled body (102) support a plurality of cam ramps (106) that taper distally. A proximal end of sled body (102) includes a downwardly extending tab (108) configured to lockingly engage a distal end of the elongate actuating beam (not shown) of firing assembly (34) when staple cartridge (80) is mounted to cartridge half (12) of stapler (10). Knife member (104) extends upwardly from an upper side of sled body (102) and presents a distally facing cutting edge (110) configured to cut tissue.

Sled (100) is configured to translate distally through cartridge body (82) in response to distal actuation of firing assembly (34), such that knife member (104) translates distally through longitudinal slot (96) to cut tissue clamped between stapler halves (12, 14). Simultaneously, cam ramps (106) translate distally through respective interior slots (not shown) of cartridge body (82) to actuate staple drivers (86) and staples (88) upwardly through staple cavities (98) so that free ends of staples (88) pierce through the clamped tissue and deform against staple forming pockets of anvil plate (60). In this manner, distal actuation of firing assembly (34) provides for simultaneous severing and stapling of tissue clamped between the distal end effector portions of stapler halves (12, 14).

Linear surgical stapler (10) and staple cartridge (80) may be further configured and operable in accordance with one or more teachings of U.S. Pat. No. 7,905,381, entitled "Surgical Stapling Instrument with Cutting Member Arrangement," issued Mar. 15, 2011; U.S. Pat. No. 7,954,686, entitled "Surgical Stapler with Apparatus for Adjusting Staple Height," issued Jun. 7, 2011; U.S. Pat. No. 8,348,129, entitled "Surgical Stapler Having A Closure Mechanism," issued Jan. 8, 2013; and/or U.S. Pat. No. 8,789,740, entitled "Linear Cutting and Stapling Device with Selectively Disengageable Cutting Member," issued Jul. 29, 2014. The disclosure of each of these references is incorporated by reference herein.

B. Exemplary Use of Linear Surgical Stapler

Figure 4A:
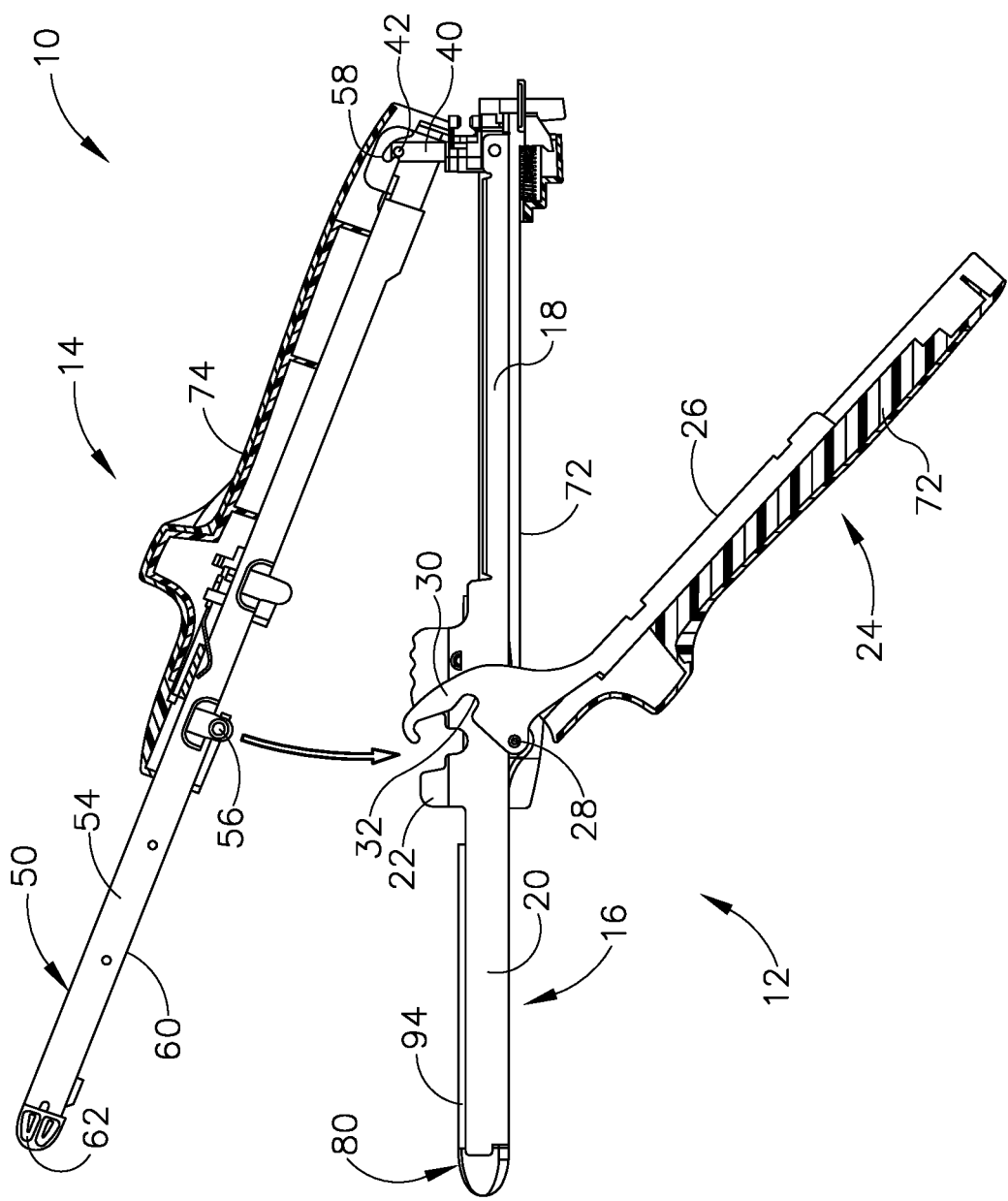
FIG. 4A depicts a cross-sectional side view of the linear surgical stapler of FIG. 1, showing the stapler halves coupled together at their proximal ends with the clamp lever in an open position.
Figure 4B:
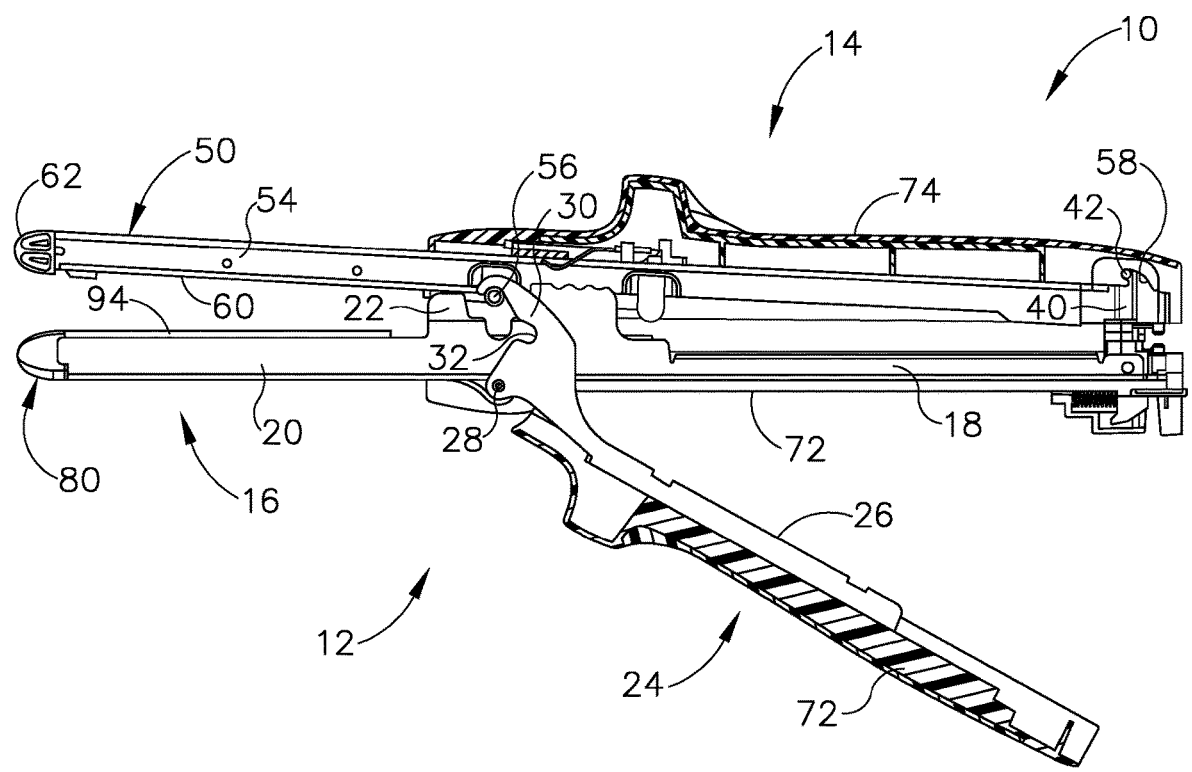
FIG. 4B depicts a cross-sectional side view of the linear surgical stapler of FIG. 1, showing the stapler halves coupled together with the clamp lever in a partially closed position.
Figure 4C:
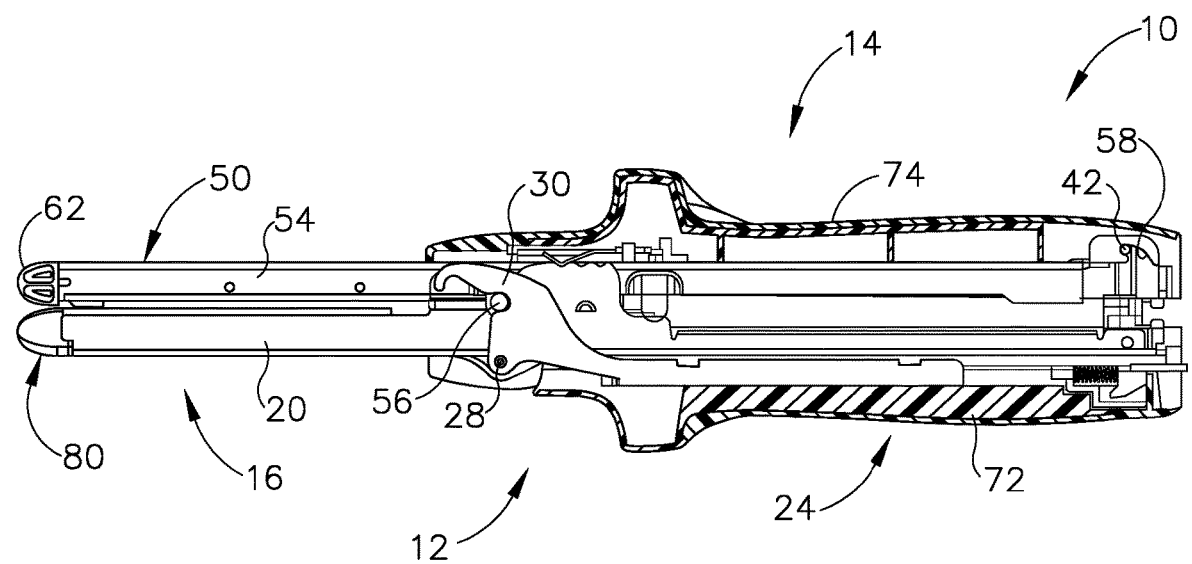
FIG. 4C depicts a cross-sectional side view of the linear surgical stapler of FIG. 1, showing the stapler halves coupled together with the clamp lever in a fully closed position.

FIGS. 4A-4C show exemplary coupling of stapler halves (12, 14) during a surgical procedure. As shown in FIG. 4A, the proximal end of anvil half (14) is aligned with the proximal end of cartridge half (12) such that proximal pivot pin (42) of cartridge half (12) is received by proximal hooks (58) of anvil half (14). With clamp lever (24) in the open position, anvil half (14) is then pivoted toward cartridge half (12), about proximal pivot pin (42), to direct latch projections of anvil half (14) into slots (32) of clamp lever jaws (30). Once latch projections (56) are received by clamp lever jaws (30), clamp lever (24) is pivoted toward the partially closed position shown in FIG. 4B. In this partially closed position of clamp lever (24), anvil half (14) is partially clamped with cartridge half (12) such that stapler (10) may now be held with a single hand without halves (12, 14) undesirably separating from one another. Additionally, in this state, the distal portions of stapler halves (12, 14) remain spaced apart from one another to permit positioning of tissue between the distal portions. It will be appreciated that tissue may be positioned between the distal portions of stapler halves (12, 14) before or upon achieving this partially clamped state.

As shown in FIG. 4C, clamp lever (24) is then pivoted further toward its fully closed position such that the camming surfaces of clamp lever jaws (30) draw latch projections of anvil half (14) proximally against the closed proximal ends of slots (32) of clamp lever jaws (30), thereby fully clamping stapler halves (12, 14) together with tissue positioned securely therebetween. Once halves (12, 14) of stapler (10) are in a fully clamped state, actuator (38) may be manipulated to fire staple cartridge (80). In particular, as shown in FIGS. 5A and 5B, actuator (38) is pivoted about the proximal end of stapler (10) to overlie one of the lateral sides of stapler (10). Actuator (38) is then driven distally to actuate firing assembly (34) in the manner described above and thereby simultaneously sever and staple the clamped tissue. Upon completing a distal firing stroke, actuator (38) may be returned to its proximal home position shown in FIG. 2, and clamp lever (24) may then be opened to separate stapler halves (12, 14) from one another and release the stapled and severed tissue.

II. Exemplary Linear Surgical Stapler Having Rotating Distal Anvil Pin

As described above in connection with FIGS. 4A-4C, anvil half (14) of linear surgical stapler (10) is clamped against cartridge half (12) by closing clamp lever (24) such that clamp lever jaws (30) capture and draw latch projections (56) proximally into jaw slots (32). Frictional engagement between jaws (30) and latch projections (56) is a significant contributing factor in the amount of closing force that an operator must exert on clamp lever (24). The exemplary linear surgical stapler (200) described below is suitably configured to minimize this frictional engagement to thereby minimize the requisite closing force. In particular, stapler (200) includes a stepped distal anvil pin (278) configured to rotate when engaged by clamp lever (240), as described in greater detail below.

A. Overview of Linear Surgical Stapler

Figure 6:
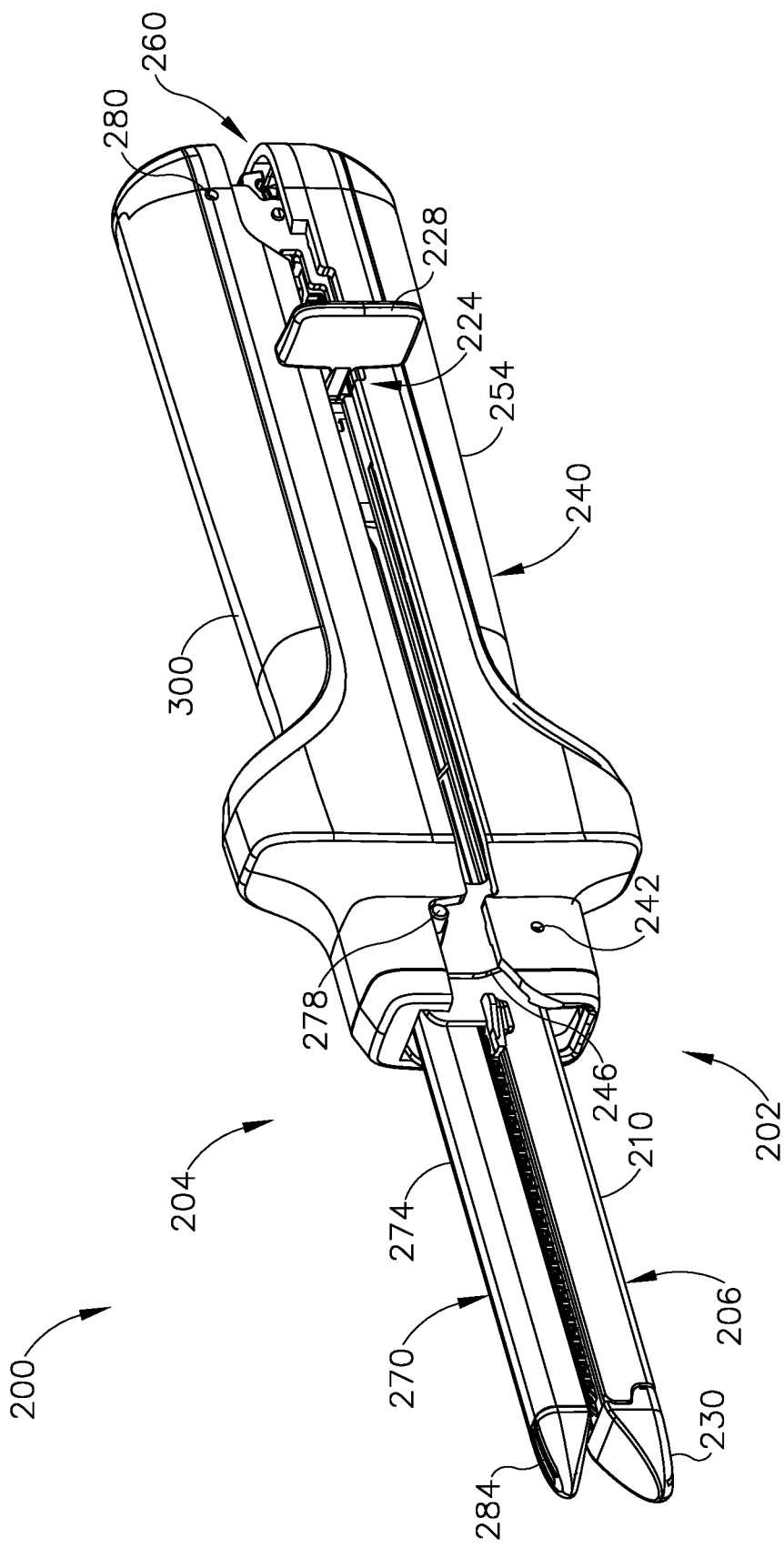
FIG. 6 depicts a distal perspective view of another exemplary linear surgical stapler, showing a cartridge half and an anvil half of the stapler coupled together with a clamp lever of the cartridge half in a fully closed position.
Figure 7:
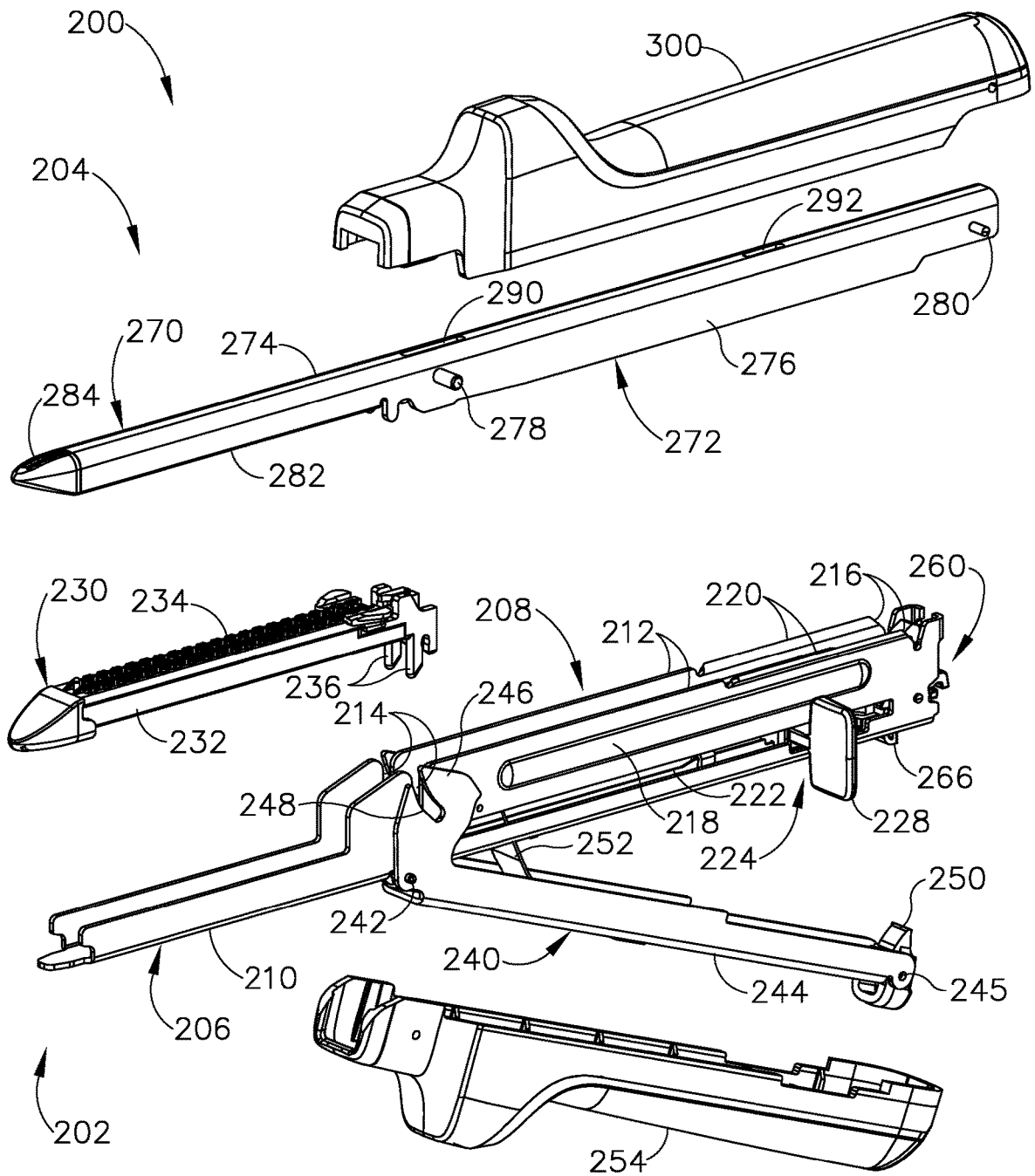
FIG. 7 depicts an exploded perspective view of the linear surgical stapler of FIG. 6.

FIGS. 6 and 7 show an exemplary linear surgical stapler (200) (or "linear cutter") that is generally similar to linear surgical stapler (10) described above except as otherwise described below. Linear surgical stapler (200) includes a cartridge half (202) (or "reload half") and an anvil half (204) configured to releasably couple together to clamp tissue therebetween for simultaneous cutting and stapling of the clamped tissue.

Cartridge half (202) includes an elongate body in the form of an elongate cartridge channel (206) having a proximal frame portion (208) and distal jaw portion (210). Proximal frame portion (208) includes a laterally opposed pair of upright side flanges (212), each having a vertical slot (214) arranged at a distal end thereof, and a tapered notch (216) arranged at a proximal end thereof. An outwardly projecting stiffening rib (218) extends longitudinally between distal slot (214) and the proximal notch (216) of each side flange (212) and is configured to provide the side flange (212) with enhanced stiffness. An outwardly flared upper segment (220) defines an upper edge of a proximal portion of each side flange (212) and is configured to facilitate receipt of anvil half (204) by cartridge half (202), described in greater detail below.

Each side flange (212) of cartridge half (202) further includes an elongate firing slot (222) extending longitudinally between proximal notch (216) and distal slot (214) along a lower side of side flange (212). Elongate firing slots (222) are configured to guide a firing assembly (224) slidably retained within proximal frame portion (208) between proximal and distal positions. Firing assembly (224) includes, among other features, a slider block (226) and a pair of actuators (228) (or "firing knobs") pivotably coupled with slider block (226) to provide dual-sided firing of stapler (10). Firing assembly (224) may be further configured in accordance with the teachings of U.S. patent application Ser. No. 16/102,164, entitled "Firing System for Linear Surgical Stapler," filed on Aug. 13, 2018, issued as U.S. Pat. No. 10,898,187 on Jan. 26, 2021, the disclosure of which is incorporated by reference herein.

Distal jaw portion (210) of cartridge channel (206) is configured to receive a staple cartridge (230) (or "reload"), which may be similar to staple cartridge (80) described above except as otherwise described below. Staple cartridge (230) includes a cartridge body (232) that houses a plurality of staple drivers and staples (not shown) similar to staple drivers (86) and staples (88). Cartridge body (232) further includes a longitudinal slot (234) configured to slidably receive a knife member (not shown) of firing assembly (224), and a pair of interior slots (not shown) configured to slidably receive a pair of cam ramps (not shown) of firing assembly (224). In other versions, staple cartridge (230) and firing assembly (224) may be alternatively configured such that the knife member and cam ramps are housed within cartridge body (232), similar to staple cartridge (80). Staple cartridge (230) of the present version further includes a pair of proximal coupling legs (236) configured to be directed through an opening (not shown) in a base wall of cartridge channel (206) and releasably coupled to a clamp lever pivot pin (242) with a snap-fit engagement.

Cartridge half (202) further includes a clamp lever (240) pivotably coupled to cartridge channel (206) with clamp lever pivot pin (242), which is arranged in approximate alignment with distal slots (214) of cartridge channel side flanges (212). Clamp lever (240) includes an elongate lever arm (244) having a free proximal end (245) and a distal end that is pivotably coupled to a lower portion of cartridge channel (206) with pivot pin (242). A pair of opposed jaws (246) extend distally from the distal end of lever arm (244) alongside cartridge channel side flanges (212). Each jaw (246) includes a curved slot (248) having a closed proximal end and an open distal end configured to receive a distal coupling member (278) of anvil half (204), as described below.

Clamp lever (240) is operable to pivot relative to cartridge channel (206) between an open position (see FIG. 11A) in which proximal end (245) of lever arm (244) is spaced from cartridge channel frame portion (208), and a closed position (see FIG. 11B) in which proximal end (245) confronts cartridge channel frame portion (208). Actuation of clamp lever (240) from the open position to the closed position operates to clamp anvil half (204) against cartridge half (202). In particular, the curvature of each jaw slot (248) defines respective upper and lower camming surfaces configured to engage and draw the distal coupling member (278) of anvil half (204) toward cartridge channel (206) as clamp lever (240) is pivotably closed, as described in greater detail below.

As shown in FIG. 7, cartridge half (202) further includes a clamp lever latch member (250) arranged at proximal end (245) of lever arm (244). As described in greater detail below, clamp lever latch member (250) is resiliently biased to engage a proximal end of cartridge channel (206) and thereby releasably retain clamp lever (240) in the closed position, for instance while stapler (200) is being fired. A resilient member shown in the form of a flat spring (252) biases clamp lever (240) toward the open position. Accordingly, flat spring (252) promotes disengagement of lever jaws (246) from anvil half (204) upon disengagement of clamp lever latch member (250) from the proximal end of cartridge channel (206), as described below.

Figure 14:
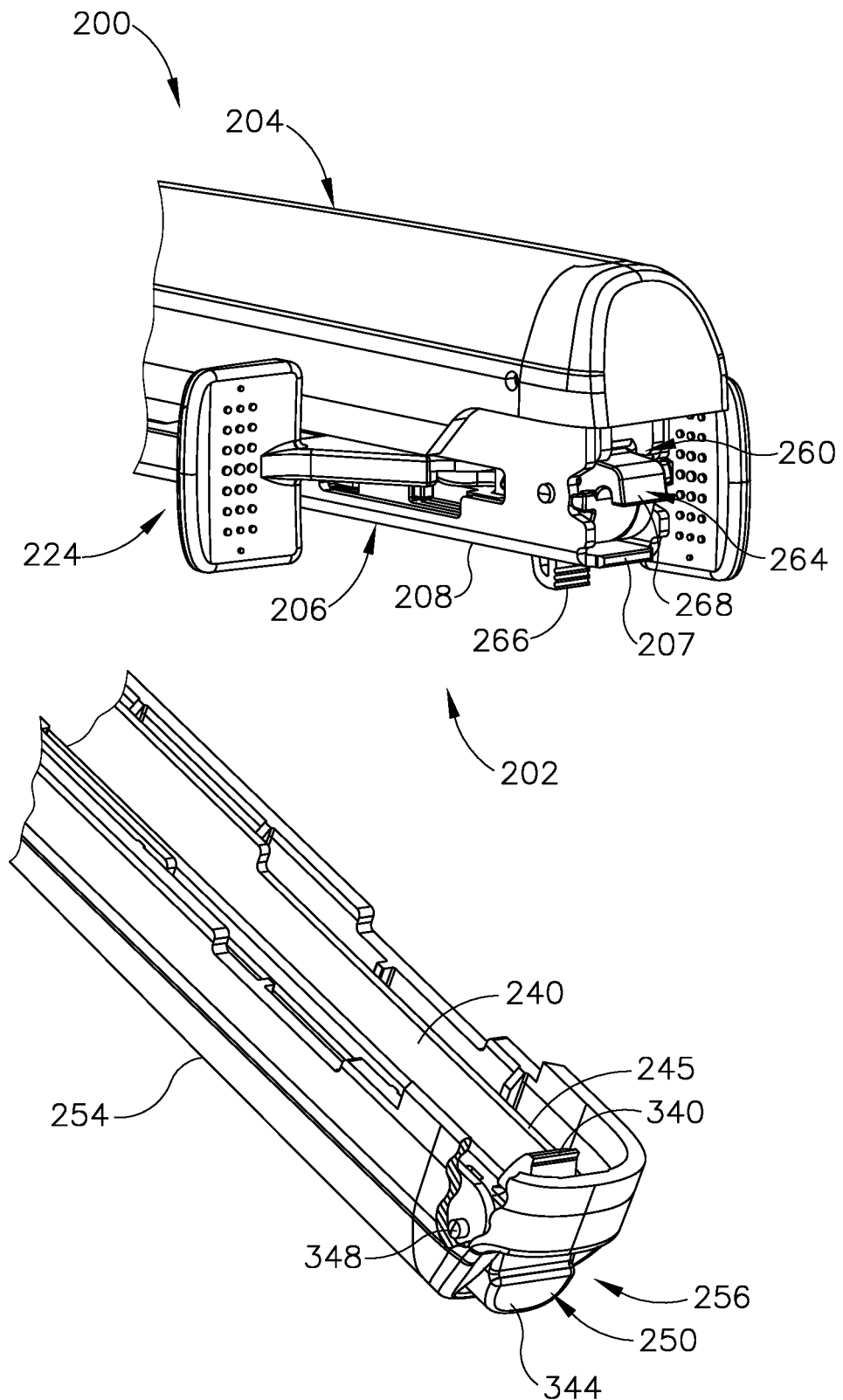
FIG. 14 depicts a perspective view of a proximal end of the linear surgical stapler of FIG. 6, showing the clamp lever in an open position.

Cartridge half (202) further includes a retaining assembly (260) arranged at a proximal end thereof. As seen best in FIGS. 12 and 16A-16D, retaining assembly (260) includes a first movable retainer in the form of an anvil latch member (262) and a second movable retainer in the form of a detent member (264) rotatably coupled to a proximal end of cartridge channel (206). Anvil latch member (262) and detent member (264) are configured to rotate independently of one another about a shared rotational axis. Anvil latch member (262) is configured to releasably capture a proximal pin (280) of anvil half (204) and thereby pivotably couple a proximal end of cartridge half (202) with a proximal end of anvil half (204). As shown in FIG. 14, anvil latch member (262) includes a lower release button (266) that is exposed through an underside of cartridge channel (206) when clamp lever (240) is opened, and which is concealed when clamp lever (240) is closed. Release button (266) is configured to be depressed by an operator to selectively disengage anvil latch member (262) from proximal anvil pin (280) and thereby permit separation of the proximal ends of stapler halves (202, 204). Detent member (264) of retaining assembly (260) is configured to releasably retain firing assembly (224) in a proximal home position. As shown in FIGS. 12 and 16A-16D, detent member (264) includes a proximal hook (268) configured to maintain clamp lever (240) in the closed position while firing assembly (224) is translated distally from its proximal home position, as described below. Retaining assembly (260) may be further configured and operable in accordance with the teachings of U.S. patent application Ser. No. 16/102,164, filed on Aug. 13, 2018, issued as U.S. Pat. No. 10,898,187 on Jan. 26, 2021, incorporated by reference above.

As shown in FIGS. 6 and 7, anvil half (204) of linear surgical stapler (200) includes an elongate body in the form of an elongate anvil channel (270) having a proximal frame portion (272) and a distal jaw portion (274). Proximal frame portion (272) includes a laterally opposed pair of side flanges (276) that are configured to be received between cartridge channel side flanges (212) when anvil half (204) is coupled with cartridge half (202). A distal coupling member in the form of a distal anvil pin (278) extends laterally through the distal ends of anvil channel side flanges (276), and a proximal coupling member in the form of a proximal anvil pin (280) extends laterally through the proximal ends of anvil channel side flanges (276). Anvil pins (278, 280) are configured to facilitate coupling of anvil half (204) with cartridge half (202) as described below.

Distal jaw portion (274) of anvil half (204) supports an anvil surface (282) having a plurality of staple forming pockets (not shown) configured to deform the legs of staples ejected by staple cartridge (230) when stapler (200) is fired. In some versions, anvil surface (282) may be formed integrally with or otherwise be rigidly connected to distal jaw portion (274). In other versions, anvil surface (282) may be adjustable relative to distal jaw portion (274) in a manner similar to anvil plate (60) of stapler (10) described above. Distal jaw portion (274) of anvil half (204) additionally supports a tapered distal tip member (284).

Similar to linear surgical stapler (10), linear surgical stapler (200) includes a plurality of shrouds (254, 300) that cover select portions of stapler (200) and promote effective grip and manipulation of stapler (200) by an operator during use. In particular, a clamp lever shroud (254) is affixed to and covers an outwardly facing side of clamp lever (240) such that clamp lever shroud (254) is configured to pivot with clamp lever (240) relative to cartridge channel (206). Additionally, an anvil shroud (300) is affixed to and covers an outwardly facing side of anvil channel (270). Exemplary methods of securing anvil shroud (300) to anvil channel (270) are described below.

During assembly of stapler halves (202, 204), proximal anvil pin (280) of anvil half (204) is directed into proximal tapered notches (216) of cartridge channel (206). Meanwhile, clamp lever (240) is held in the open position by resilient member (252) such that the open distal ends of curved jaw slots (248) align with the open upper ends of cartridge channel distal slots (214). Anvil half (204) is then pivoted about proximal anvil pin (280) to direct distal anvil pin (278) into vertical distal slots (214) of cartridge channel (206) and curved jaw slots (248) of clamp lever (240). Clamp lever (240) is then pivoted from the open position to the closed position, which causes the upper and lower camming surfaces of curved jaw slots (248) to engage and draw distal anvil pin (278) toward the closed proximal ends of curved jaw slots (248). This action draws distal jaw portion (274) of anvil channel (270) closer toward distal jaw portion (210) of cartridge channel (206), thereby clamping any tissue positioned between anvil surface (282) and staple cartridge (230). When clamp lever (240) reaches the fully closed position, clamp lever latch member (250) engages the proximal end of cartridge channel (206) to maintain clamp lever (240) in the closed position. Stapler (200) may then be fired by actuating firing assembly (224) distally, similar to firing assembly (34). After stapler (200) is fired, firing assembly (224) is returned to its proximal home position, and clamp lever latch member (250) is disengaged from cartridge channel (206) to enable opening of clamp lever (240) and subsequent separation of stapler halves (202, 204).

B. Exemplary Assembly of Anvil Half Components

Figure 8:
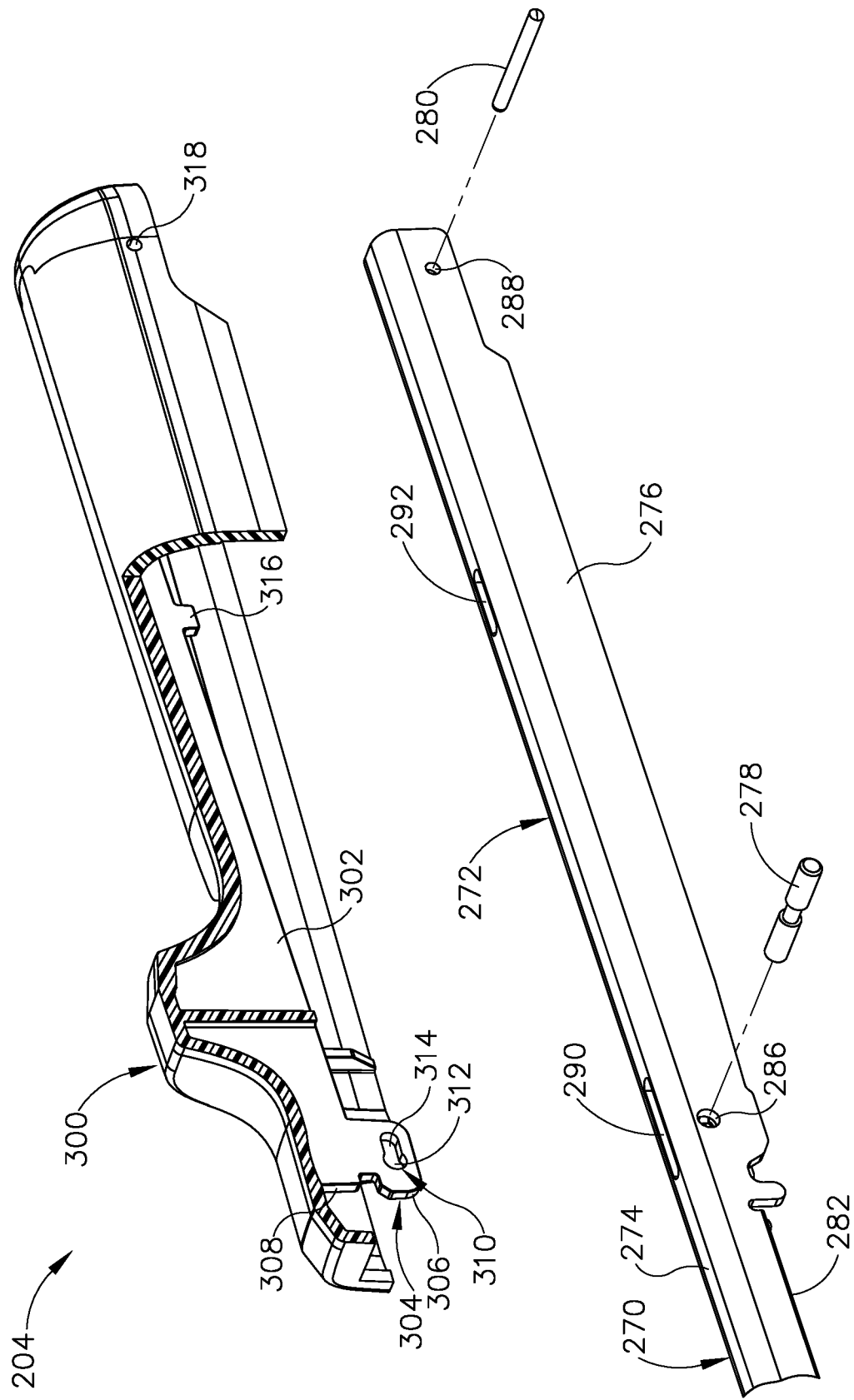
FIG. 8 depicts an exploded perspective view of the anvil half of the linear surgical stapler of FIG. 6, showing an anvil channel, an anvil shroud, and proximal and distal anvil pins, and showing the anvil shroud partially cut-away to reveal an inner flange.

FIGS. 8-10C show additional details of components of anvil half (204), and corresponding steps of assembling such components. As shown in FIG. 8, anvil channel side flanges (276) include a pair of distal openings (286) configured to receive distal anvil pin (278) laterally therethrough, and a pair of proximal openings (288) configured to receive proximal anvil pin (280) laterally therethrough. A base wall of proximal frame portion (272) includes an elongate distal slot (290) arranged approximately in alignment with distal openings (286), and a proximal slot (292) arranged longitudinally between distal openings (286) and proximal openings (288). Proximal and distal slots (290, 292) are positioned along a longitudinal centerline of anvil channel (270).

Anvil shroud (300), shown in partial cross-section in FIG. 8, includes an inner flange (302) extending longitudinally within an interior of anvil shroud (300), parallel to the longitudinal centerline of anvil channel (270), and projecting transversely in a direction toward anvil channel (270). Inner flange (302) includes a foot-shaped distal tab (304) extending transversely toward anvil channel (270) and having a distal nose (306) that extends distally beyond a distal end (308) of a base portion of inner flange (302). Distal tab (304) includes a keyhole slot (310) having a circular entry portion (312) and an elongate retaining portion (314) extending proximally from circular entry portion (312). In the present example, keyhole slot (310) is oriented parallel to a longitudinal axis of anvil channel (270). Inner flange (302) further includes a rectangular proximal tab (316) extending transversely toward anvil channel (270). Distal slot (290) of anvil channel (270) is configured to receive distal tab (304) of anvil shroud (300), and proximal slot (292) is configured to receive proximal tab (316). As described below, anvil channel slots (290, 292) are suitably sized such that the respective tab (304, 316) is slidable longitudinally therein. Anvil shroud (300) further includes a pair of proximal openings (318) extending laterally through a proximal end of anvil shroud (300), and are configured to receive proximal anvil pin (280) therethrough as described below.

Figure 9:
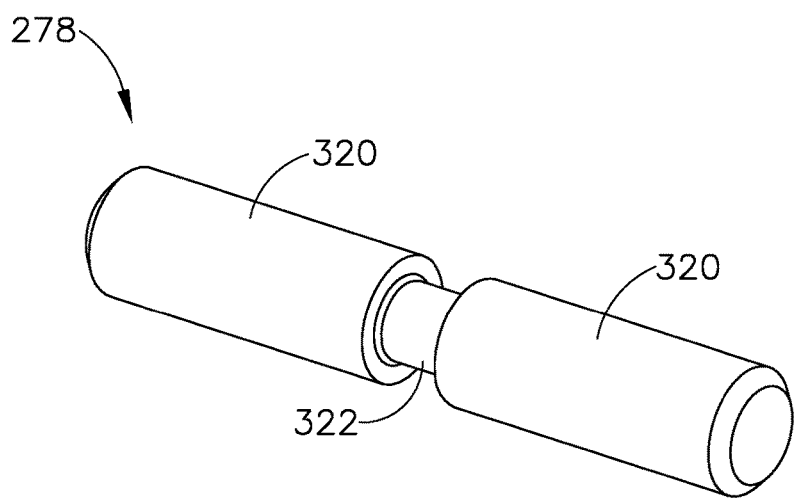
FIG. 9 depicts a perspective view of the distal anvil pin of FIG. 8.

As shown in FIG. 9, distal anvil pin (278) of the present version is in the form of a stepped pin having a pair of cylindrical shoulders (320) and a cylindrical neck (322) arranged medially therebetween. Pin neck (322) is formed with a smaller outer diameter than pin shoulders (320) such that pin shoulders (320) define a maximum outer diameter of distal anvil pin (278) and pin neck (322) defines a minimum outer diameter of distal anvil pin (278). As seen in FIG. 8, proximal pin (280) of the present example is cylindrical with a non-stepped configuration.

Figure 10A:
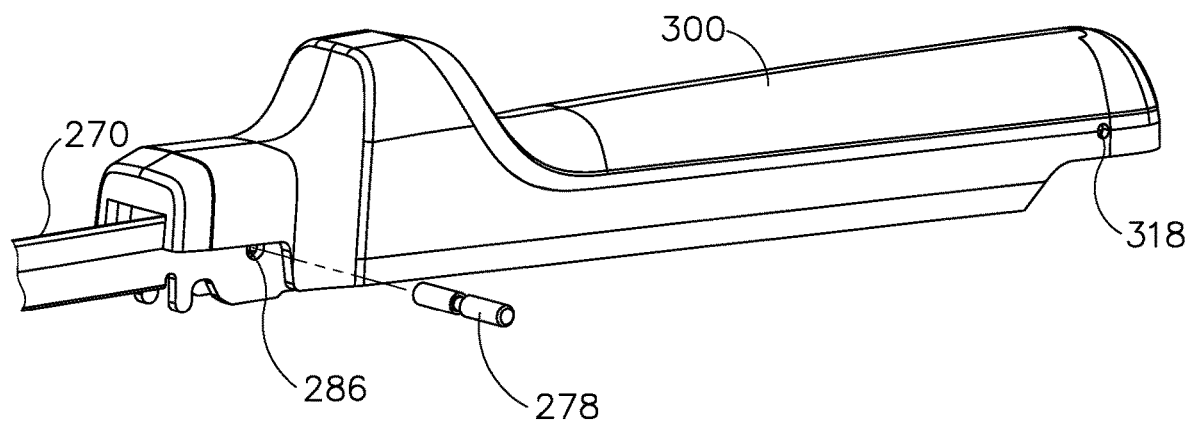
FIG. 10A depicts a perspective view of components of the anvil half of FIG. 6 during assembly, showing the distal anvil pin being aligned with a pair of distal pin openings of the anvil channel and a keyhole slot of the anvil shroud for assembly of the anvil half.
Figure 10B:
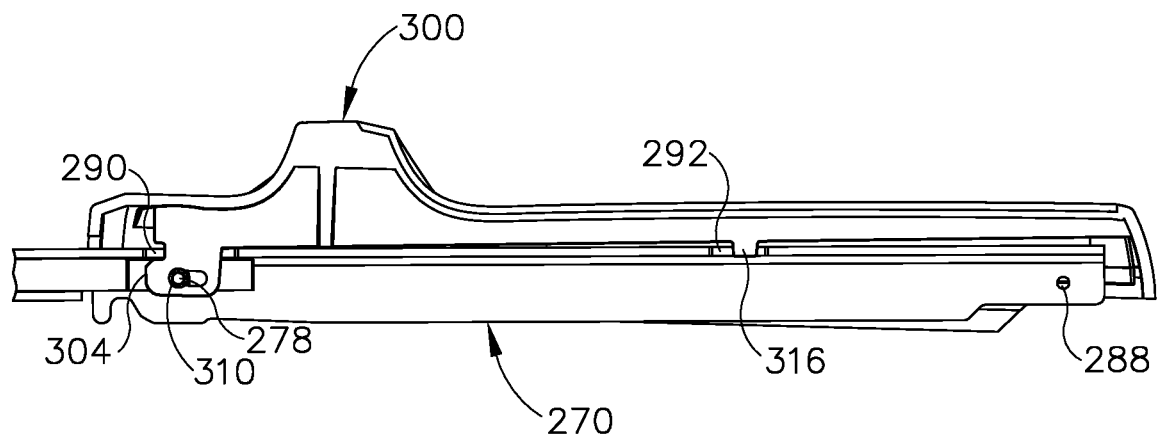
FIG. 10B depicts a side cross-sectional view of components of the anvil half of FIG. 6 during assembly, showing the distal anvil pin extending laterally through the anvil channel and the anvil shroud flange.
Figure 10C:
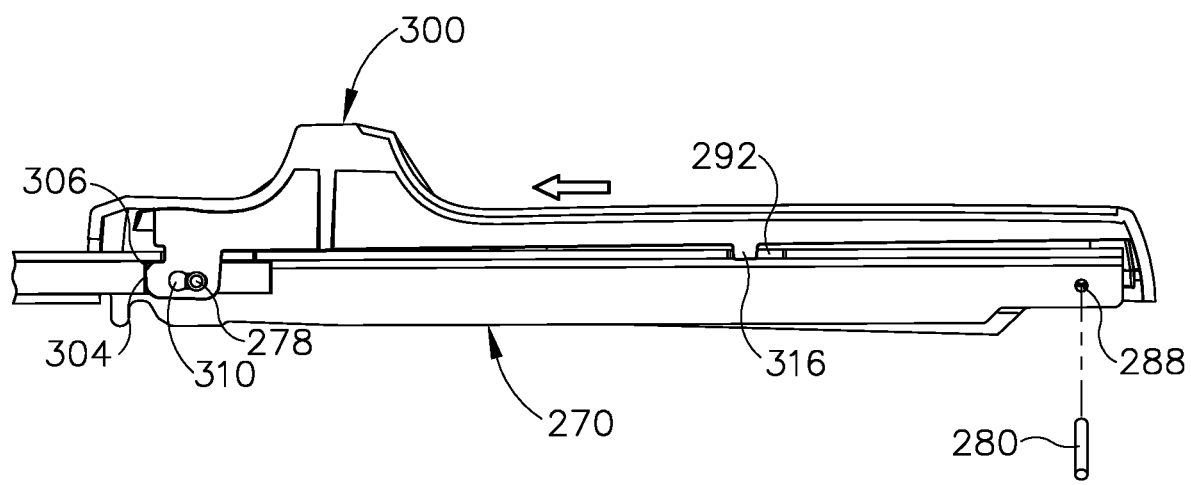
FIG. 10C depicts a side cross-sectional view of components of the anvil half of FIG. 6 during assembly, showing the anvil shroud being translated distally relative to the anvil channel and the proximal anvil pin being inserted through proximal ends of the anvil shroud and anvil channel.

FIG. 10A depicts components of anvil half (204) during an initial stage of assembly, showing anvil shroud (300) having been lowered onto anvil channel (270) such that distal tab (304) of anvil shroud (300) is received through distal slot (290) of anvil channel (270) and proximal tab (316) is received through proximal slot (292). As shown in FIG. 10B, anvil shroud tabs (304, 316) are positioned proximally within slots (290, 292) such that circular entry portion (312) of keyhole slot (310) aligns longitudinally with distal openings (286) of anvil channel (270). Stepped distal anvil pin (278) is then inserted laterally through distal openings (286) and circular entry portion (312), such that narrowed neck (322) of distal anvil pin (278) resides within keyhole slot (310). As shown in FIG. 10C, anvil shroud (300) is then translated distally relative to anvil channel (270) such that anvil shroud tabs (304, 316) slide distally within their respective anvil channel slots (290, 292), and such that proximal shroud openings (318) are brought into alignment with proximal anvil channel openings (288). Proximal anvil pin (280) is then inserted laterally through aligned proximal openings (288, 318), thereby fixing anvil shroud (300) longitudinally relative to anvil channel (270), and fixing the proximal end of anvil shroud (300) transversely relative to anvil channel (270). Proximal shroud openings (318) may be sized to receive proximal anvil pin (280) with an interference fit, thereby securing proximal pin (280) laterally relative to anvil shroud (300) and anvil channel (270) once inserted.

The distal translation of anvil shroud (300) relative to anvil channel (270) shown in FIG. 10C also operates to position distal nose (306) of distal shroud tab (304) distally of a distal end of distal anvil channel slot (290), thereby securing the distal end of anvil shroud (300) transversely relative to anvil channel (270). Additionally, narrowed neck (322) of distal anvil pin (278) is received within elongate retaining portion (314) of keyhole slot (310) of anvil shroud (300). Each pin shoulder (320) is formed with an outer diameter that is slightly larger than the diameter of elongate retaining portion (314) such that distal anvil pin (278) is constrained laterally relative to anvil shroud (300) and anvil channel (270). Furthermore, distal openings (286) of anvil channel (270) are sized slightly larger than pin shoulders (320), and elongate retaining portion (314) of keyhole slot (310) is sized slightly larger than pin neck (322), such that distal anvil pin (278) is configured to rotate relative to anvil channel (270) and anvil shroud (300) with a slip fit engagement even though constrained laterally.

Figure 11A:
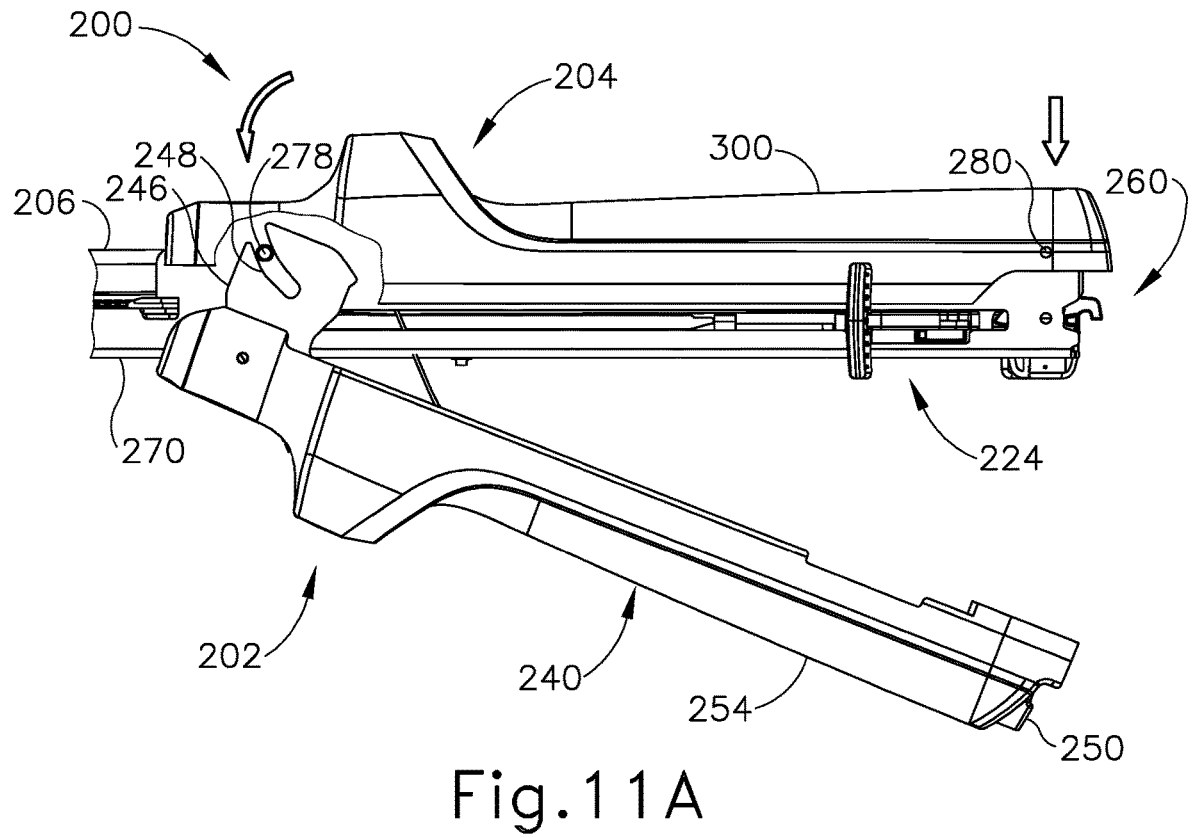
FIG. 11A depicts a side elevational view of the linear surgical stapler of FIG. 6, showing the proximal and distal anvil pins of the anvil half being aligned with the cartridge half while the clamp lever is in the open position.
Figure 11B:
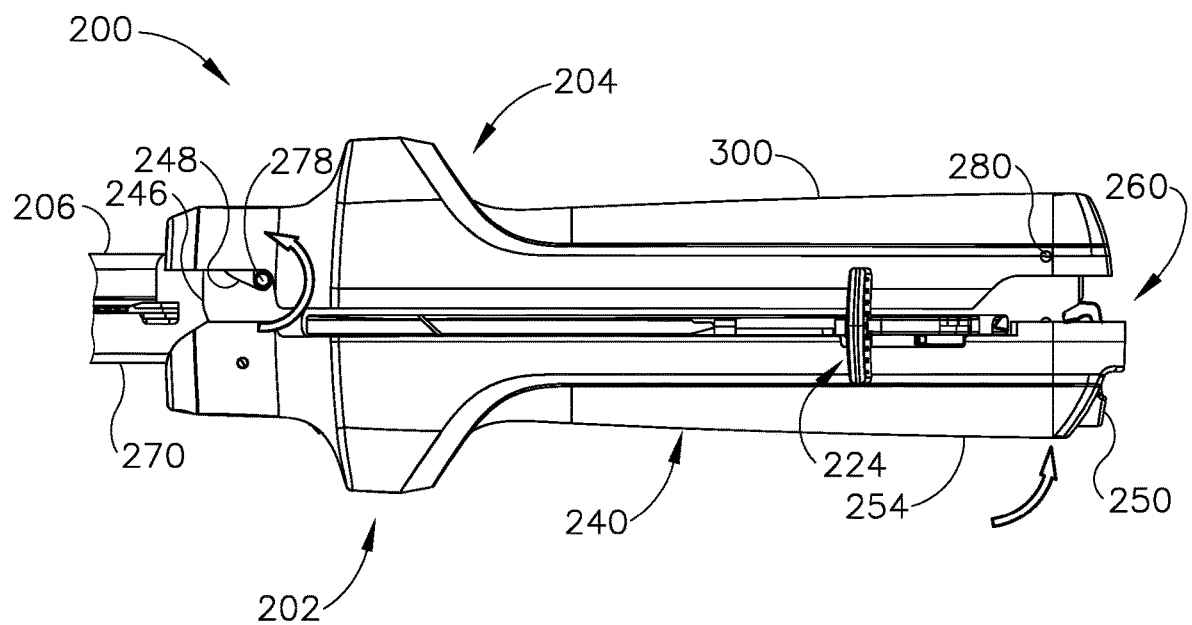
FIG. 11B depicts a side elevational view of the linear surgical stapler of FIG. 6, showing the clamp lever pivoted to a closed position such that a distal end of the clamp lever clamps the anvil half against the cartridge half.

As shown in FIGS. 11A and 11B, anvil half (204) is mounted to cartridge half (202) in the manner generally described above, such that proximal anvil pin (280) is received within proximal tapered notches (216) (see FIG. 7) of cartridge channel (206). A medial portion of proximal anvil pin (280) is captured by anvil latch member (262) (see FIG. 12) of proximal retaining assembly (260) of cartridge half (202), thereby pivotably coupling the proximal end of anvil half (204) with the proximal end of cartridge half (202). Anvil half (204) is then pivoted about proximal anvil pin (280) to direct pin shoulders (320) of distal anvil pin (278) into distal vertical slots (214) of cartridge channel (206) (see FIG. 7) and curved slots (248) of clamp lever jaws (246). Clamp lever (240) is then pivoted from the open position to the closed position so that the upper and lower camming surfaces of jaw slots (248) engage distal pin shoulders (320). In response to being engaged by the camming surfaces of jaw slots (248), distal anvil pin (278) rotates relative to anvil channel (270) and anvil shroud (300), and thereby rolls along the camming surfaces of jaw slots (248). In particular, in the left-side view shown in FIG. 11B, distal anvil pin (278) rotates in a counter-clockwise direction when clamp lever (240) is closed, and in a clockwise direction when clamp lever (240) is opened. Advantageously, this rotation of distal anvil pin (278) helps to minimize friction between clamp lever jaws (246) and distal anvil pin (278) when clamp lever (240) is closed and opened, and consequently minimize the forces that an operator must exert on clamp lever (240) to transition stapler (200) between unclamped and clamped states.

C. Proximal Hinge Stops of Linear Surgical Stapler

Figure 12:
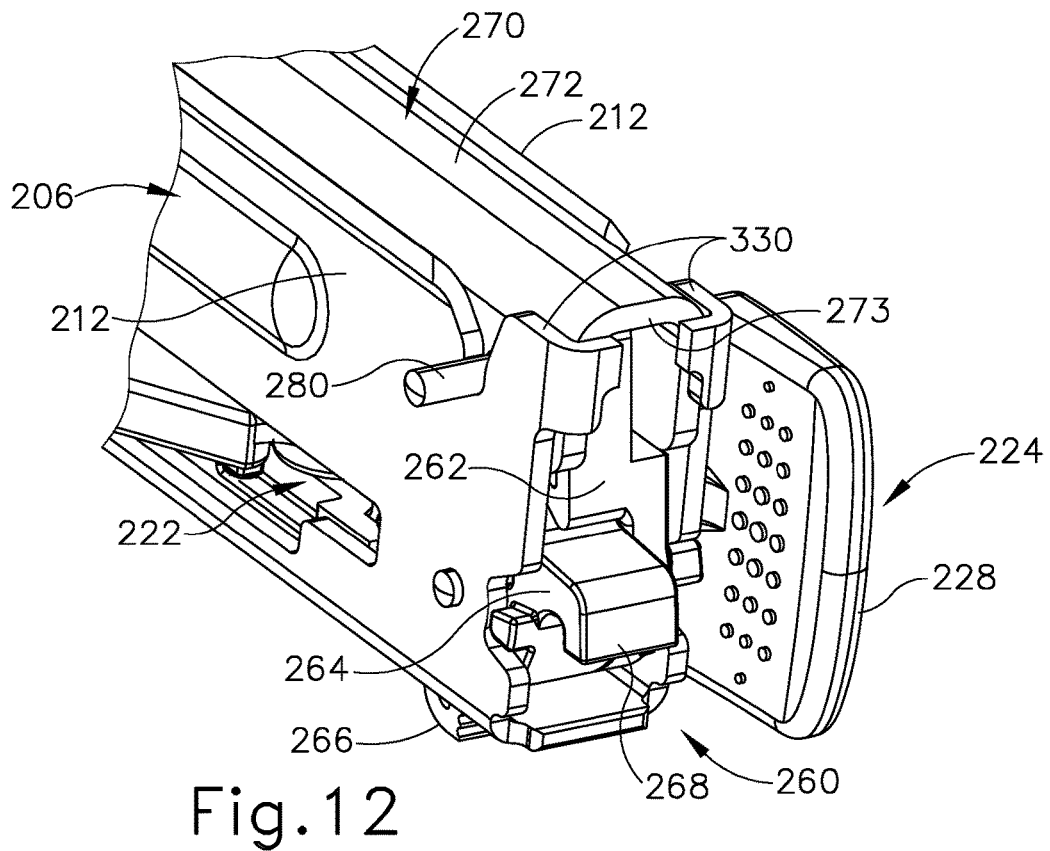
FIG. 12 depicts a perspective view of a proximal end of the linear surgical stapler of FIG. 6, with the clamp lever in an open position and with the anvil shroud being omitted from view.
Figure 13:
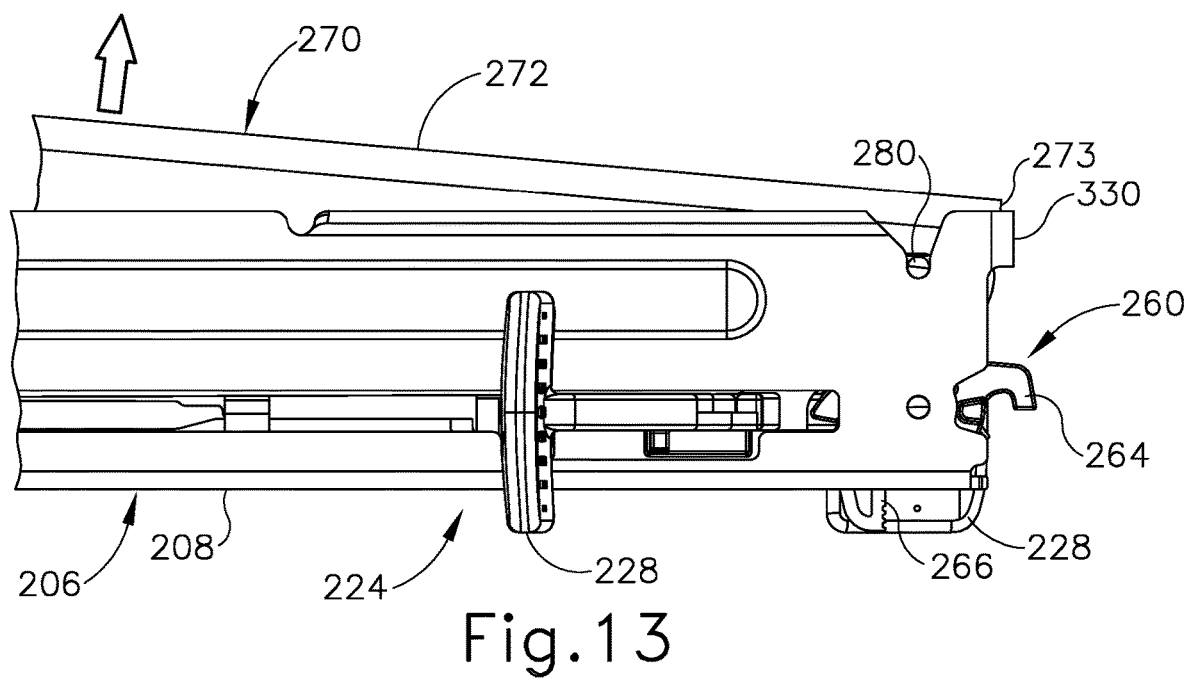
FIG. 13 depicts a side elevational view of the linear surgical stapler of FIG. 6, with the clamp lever in an open position and with the anvil shroud being omitted from view, showing the anvil channel being pivoted relative to the cartridge half.

FIGS. 12 and 13 show details of an exemplary pair of hinge stops (330) rigidly coupled with a proximal end of cartridge channel (206). In the present version, hinge stops (330) are in the form of tabs integrally formed with the upper proximal ends of cartridge channel side flanges (212), and have free ends that wrap inwardly to define a proximal-most end of cartridge channel (206). In use, hinge stops (330) are configured to abut a proximal face (273) of proximal frame portion (272) of anvil channel (270) to limit the degree to which anvil half (204) may pivotably open relative to cartridge half (202). Hinge stops (330) may be suitably configured to permit any desired degree of pivoting of anvil half (204) relative to cartridge half (202) so as to permit a corresponding maximum aperture distance between the distal ends of anvil half (204) and cartridge half (202).

D. Clamp Lever Latch Member of Linear Surgical Stapler

Figure 15:
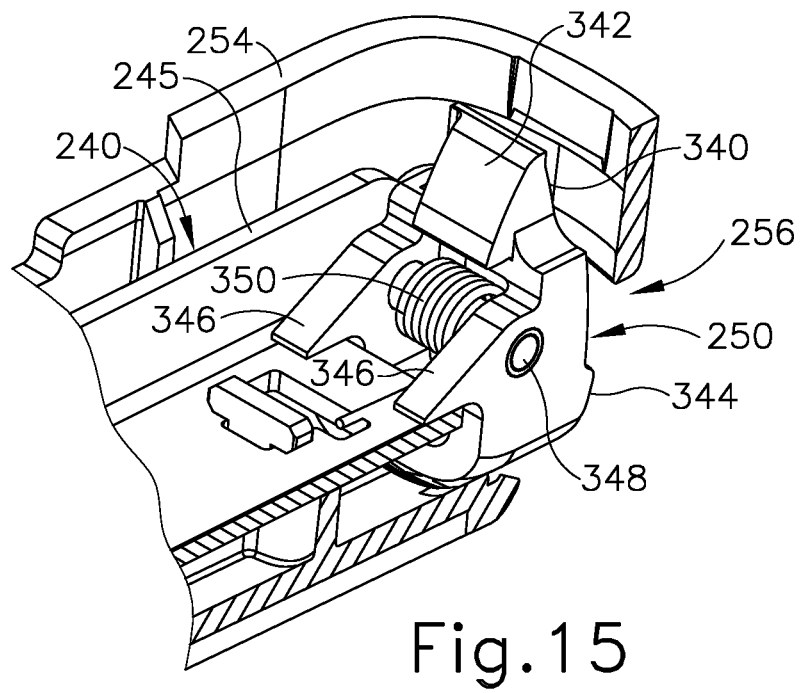
FIG. 15 depicts a perspective view of a proximal end of the clamp lever and clamp lever shroud of the linear surgical stapler of FIG. 6, showing the clamp lever and clamp lever shroud partially cut away to reveal details of a clamp lever latch member.

FIGS. 14-16D show additional details and functionality of clamp lever latch member (250) of linear surgical stapler (200). As described above, clamp lever latch member (250) is configured to releasably couple free proximal end (245) of clamp lever (240) to proximal frame portion (208) of cartridge channel (206), and thereby releasably maintain clamp lever (240) in the closed position. As shown in FIGS. 14 and 15, clamp lever latch member (250) includes an upwardly extending finger (340) having a distally facing cam surface (342), a downwardly extending release button (344), and a pair of distally extending stop arms (346). Clamp lever latch member (250) is pivotably coupled to proximal end (245) of clamp lever (240) with a laterally extending pin (348) such that upper finger (340) extends transversely toward cartridge channel (206) and lower release button (344) extends transversely away from cartridge channel (206). A proximal end of clamp lever shroud (254) wraps around clamp lever latch member (250) and includes an opening (256) that exposes lower release button (344) for access by an operator.

Figure 16A:
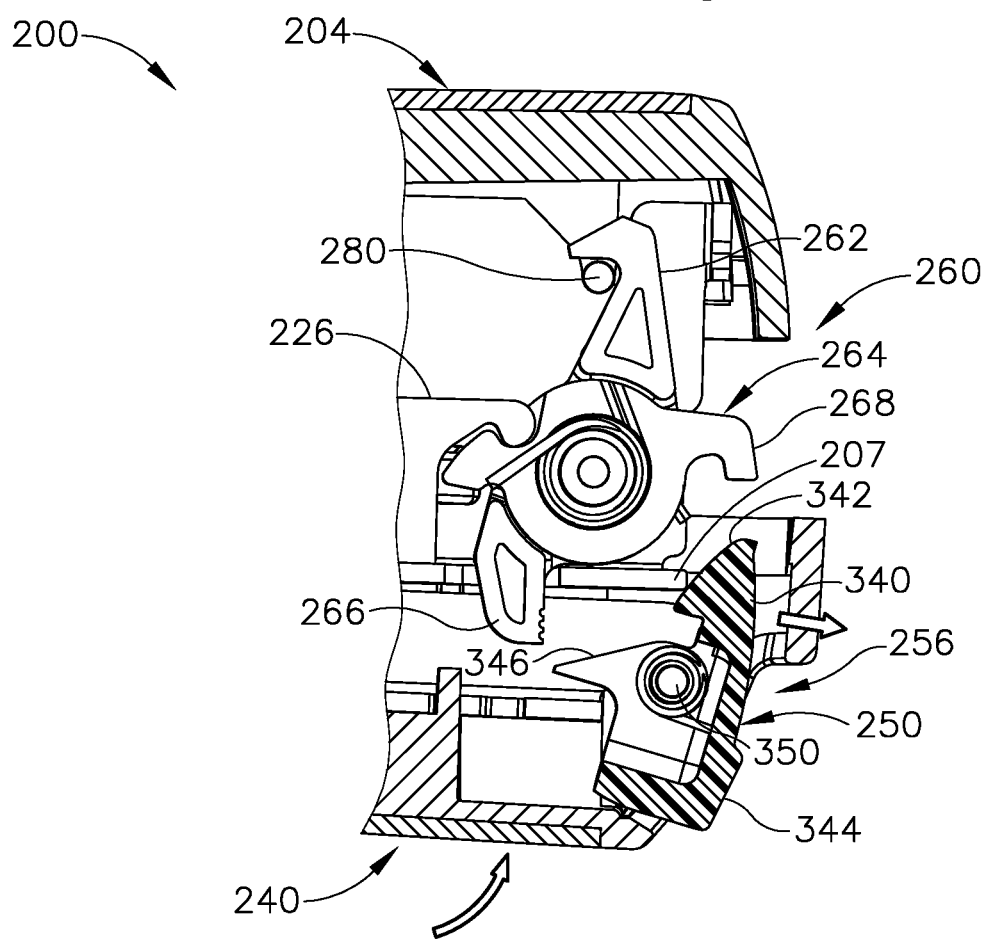
FIG. 16A depicts a side cross-sectional view of a proximal end of the linear surgical stapler of FIG. 6, showing the clamp lever being closed to engage the clamp lever latch member with a proximal end of the cartridge channel.
Figure 16B:
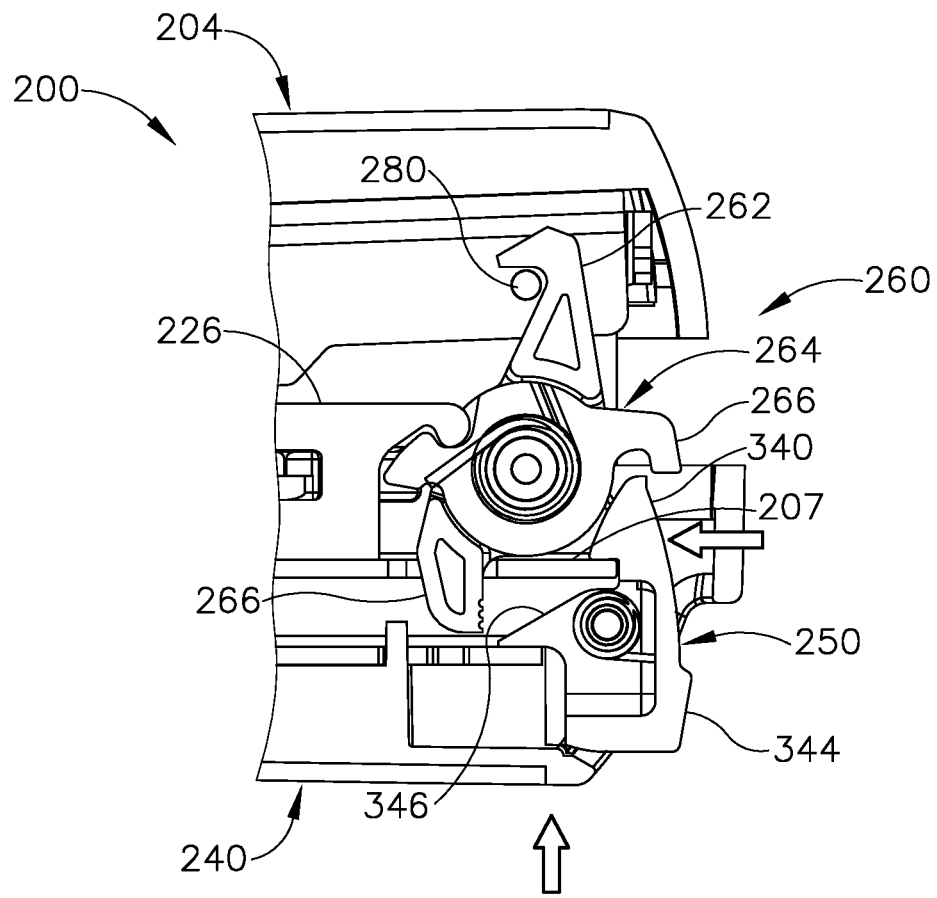
FIG. 16B depicts a side cross-sectional view of the proximal end of the linear surgical stapler of FIG. 6, showing the clamp lever in a fully closed position.

Clamp lever latch member (250) is configured to rotate relative to lever arm (244) about pivot pin (348). A resilient member shown in the form of a torsion spring (350) biases latch member (250) rotationally such that distal stop arms (346) rest against an inner base surface of lever arm (244). As shown in FIG. 16A, latch member (250) is configured to rotate against the bias of torsion spring (350) when distal cam surface (342) contacts a proximal ledge (207) of cartridge channel (206) during closure of clamp lever (240). As shown in FIG. 16B, when clamp lever (240) reaches a fully closed position, upper finger (340) of clamp lever latch member (250) hooks over proximal ledge (207), thereby maintaining clamp lever (240) in the closed position.

Figure 16C:
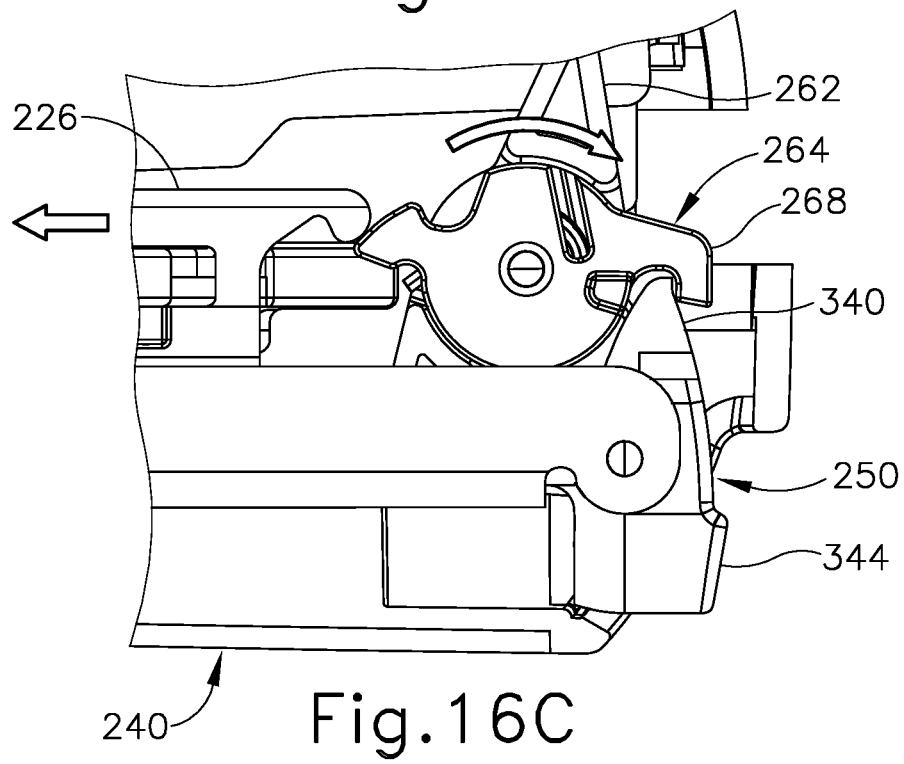
FIG. 16C depicts a side cross-sectional view of the proximal end of the linear surgical stapler of FIG. 6, showing a firing assembly being translated distally such that a lockout feature engages and locks out the clamp lever latch member.
Figure 16D:
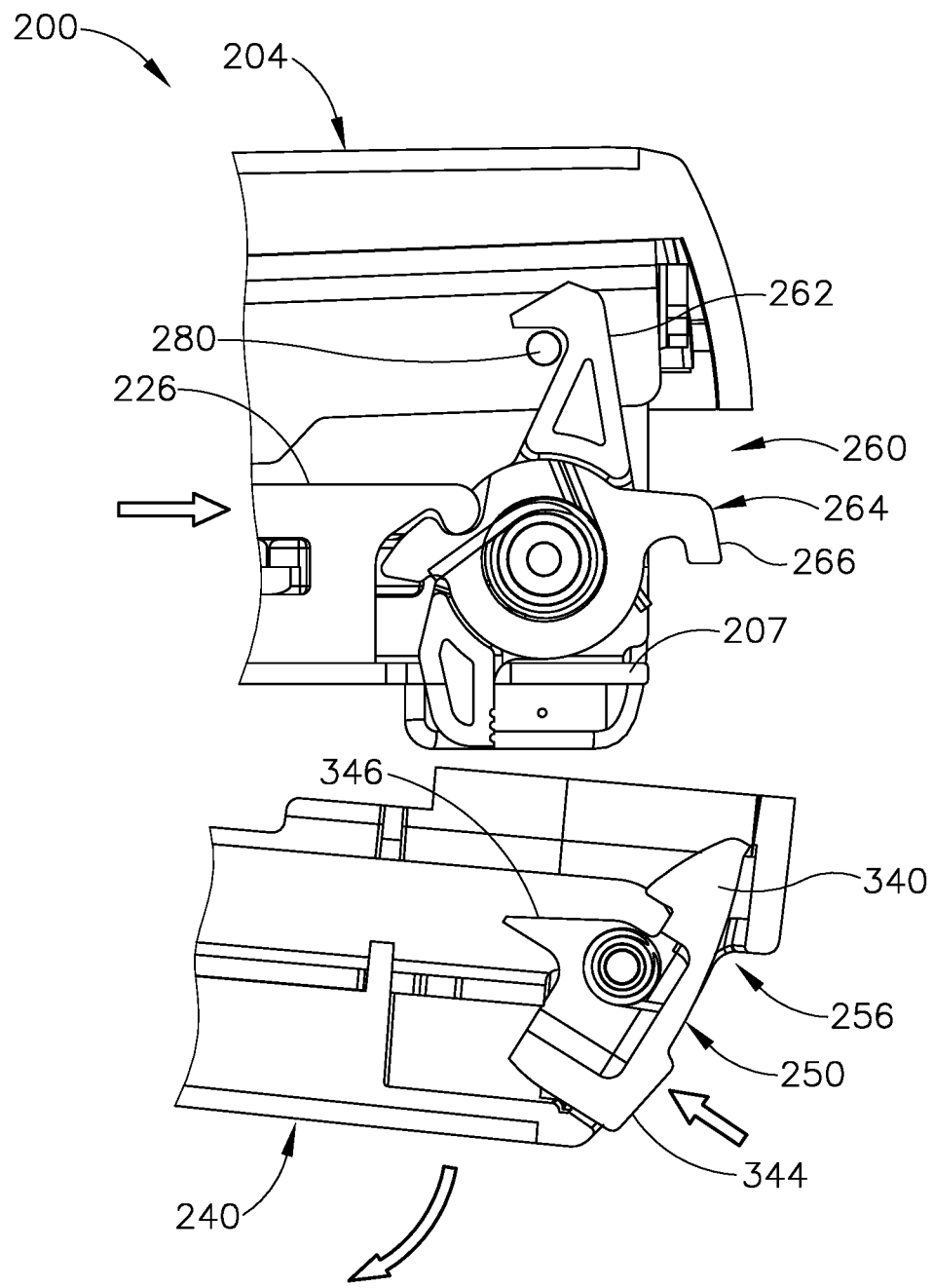
FIG. 16D depicts a side cross-sectional view of the proximal end of the linear surgical stapler of FIG. 6, showing the clamp lever latch member being actuated to disengage the channel member and permit opening of the clamp lever.

As shown in FIG. 16C, when firing assembly (224) of stapler (200) is translated distally during a firing stroke, slider block (226) disengages detent member (264) of proximal retaining assembly (260). This disengagement enables detent member (264) to rotate clockwise (in the left-side view shown in FIG. 16C) under rotational bias such that proximal hook (268) of detent member (264) latches over the tip of upper finger (340) of clamp lever latch member (250). This engagement of detent member (264) with clamp lever latch member (250) prevents latch member (250) from being rotated via release button (344) to disengage latch member (250) from cartridge channel (206). Consequently, clamp lever (240) is locked in the closed position while firing assembly (224) is translated distally from its proximal home position during a firing stroke. As shown FIG. 16D, return of slider block (226) of firing assembly (224) to its proximal home position rotates detent member (264) and its hook (268) away from clamp lever latch member (250). Consequently, lower release button (344) may be depressed by an operator to disengage clamp lever latch member (250) from cartridge channel (206) and then open clamp lever (240).

III. Exemplary Clamp Lever Latch Mechanism Having Distal Release Feature

As described above in connection with linear surgical stapler (200), clamp lever latch member (250) is configured such that its latch feature (340) and its release feature (344) are both arranged at the proximal end of clamp lever (240). In some instances, however, it may be desirable to employ a clamp lever latch mechanism that provides the release feature at a distal end of clamp lever (240) while maintaining the latch feature at a proximal end of clamp lever (240). Such a configuration may enable an operator to more easily release the latch mechanism and open clamp lever (240) with a single hand.

Figure 17:
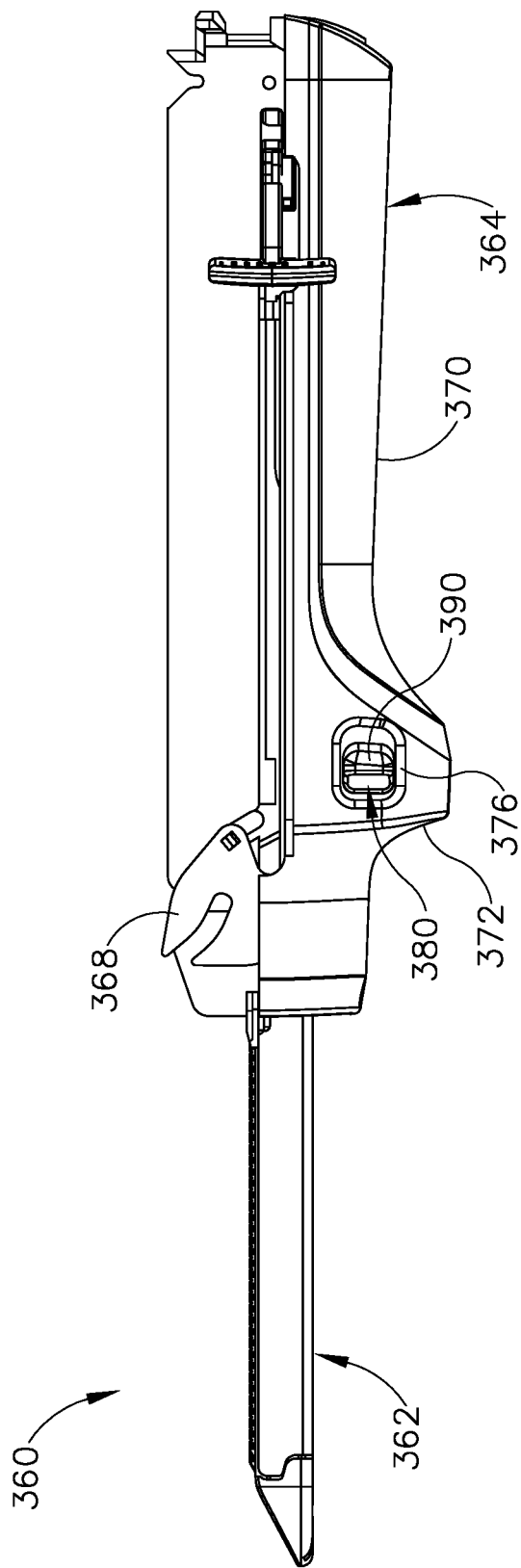
FIG. 17 depicts a side elevational view of another exemplary cartridge half of a linear surgical stapler.
Figure 18:
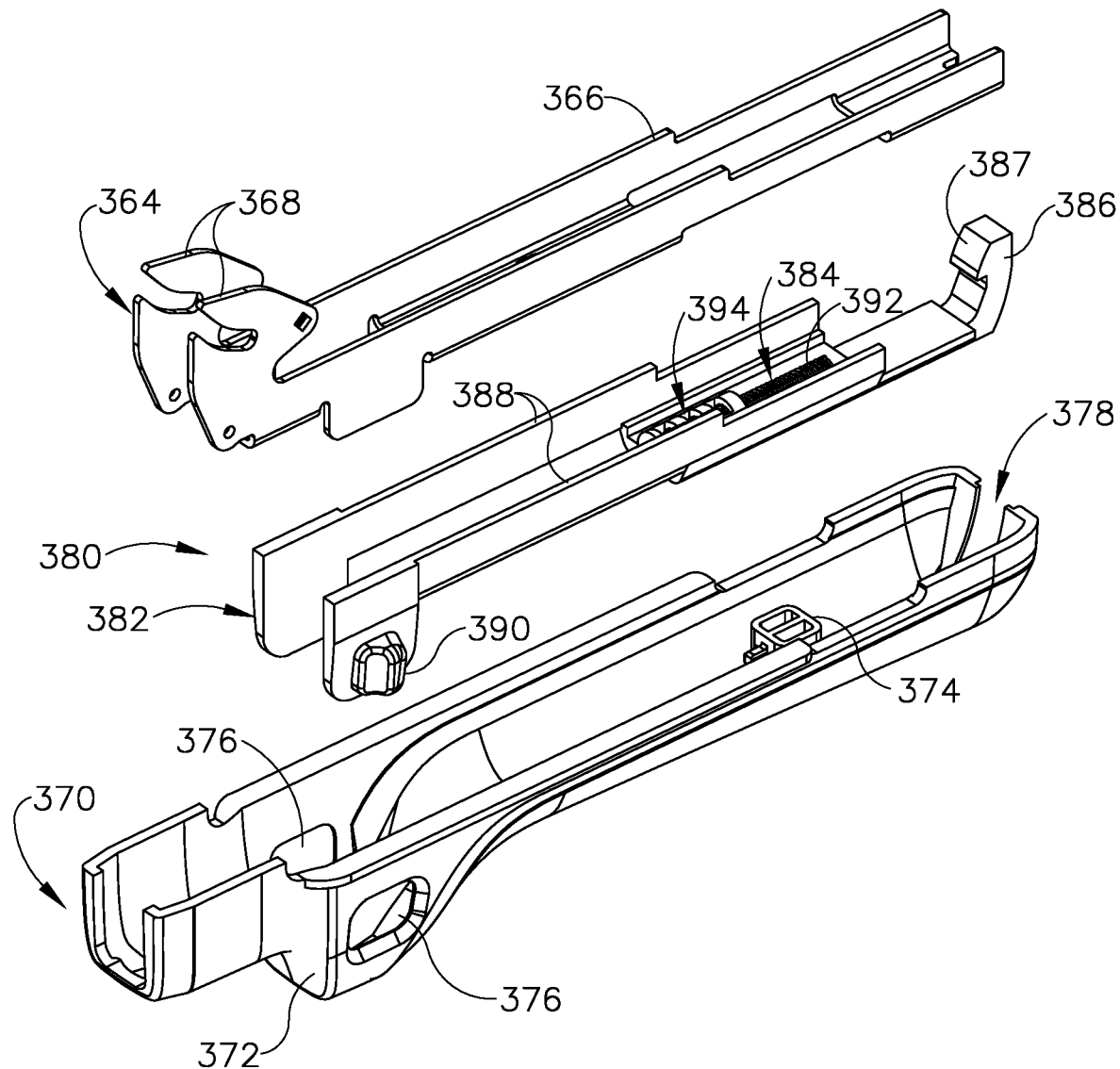
FIG. 18 depicts an exploded view of several components of the cartridge half of FIG. 17, showing a clamp lever, a translating shoulder latch mechanism, and a clamp lever shroud.

FIGS. 17 and 18 show an exemplary cartridge half (360) of a linear surgical stapler that includes a clamp lever latch mechanism (380) having a configuration of the type described above. Cartridge half (360) and/or one or more of its components are suitable for use with the complementary portions of linear surgical stapler (200) described above. Cartridge half (360) is similar to cartridge half (202) of stapler (200) except as otherwise described below. Similar to cartridge half (202), cartridge half (360) includes an elongate cartridge channel (362), a clamp lever (364) pivotably coupled with cartridge channel (362) and having a lever arm (366) and a pair of lever jaws (368), and a clamp lever shroud (370) coupled to lever arm (366) and having a distal shoulder (372).

As shown best in FIG. 18, cartridge half (360) further includes a clamp lever latch mechanism (380) that is received within clamp lever shroud (370) and about an exterior of clamp lever (364). Latch mechanism (380) of the present example includes a translating structure (382) having a central body (384), a latch finger (386) rigidly coupled to and extending proximally from central body (384), and a pair of actuator arms (388) rigidly coupled to and extending distally from central body (384). Each actuator arm (388) includes a distal actuator knob (390). Clamp lever latch mechanism (380) further includes a resilient member shown in the form of a compression spring (392). Spring (392) is constrained at a proximal end by an anchor element (374) rigidly coupled with a base surface of clamp lever shroud (370), and at a distal end by a spring basket (394) of central body (384). As described below, translating structure (382) is configured to translate relative to clamp lever (364) and clamp lever shroud (370) between proximal and distal positions, and compression spring (392) is configured to bias translating structure (382) distally.

Clamp lever (364), clamp lever shroud (370), and clamp lever latch mechanism (380) are configured to be assembled such that latch mechanism (380) is slidably received within an interior of shroud (370). Actuator arms (388) are configured to flex laterally relative to central body (384) to facilitate assembly. Each actuator knob (390) is exposed through a distal opening (376) formed in a respective lateral side of shroud shoulder (372), and proximal latch finger (386) is exposed through a proximal opening (378) formed in a proximal end of shroud (370). Latch mechanism (380) and shroud (370) are then mounted to clamp lever arm (366) such that shroud (370) is fixed relative to lever arm (366) while translating structure (382) of latch mechanism (380) remains longitudinally translatable relative to clamp lever (364) and shroud (370).

Figure 19A:
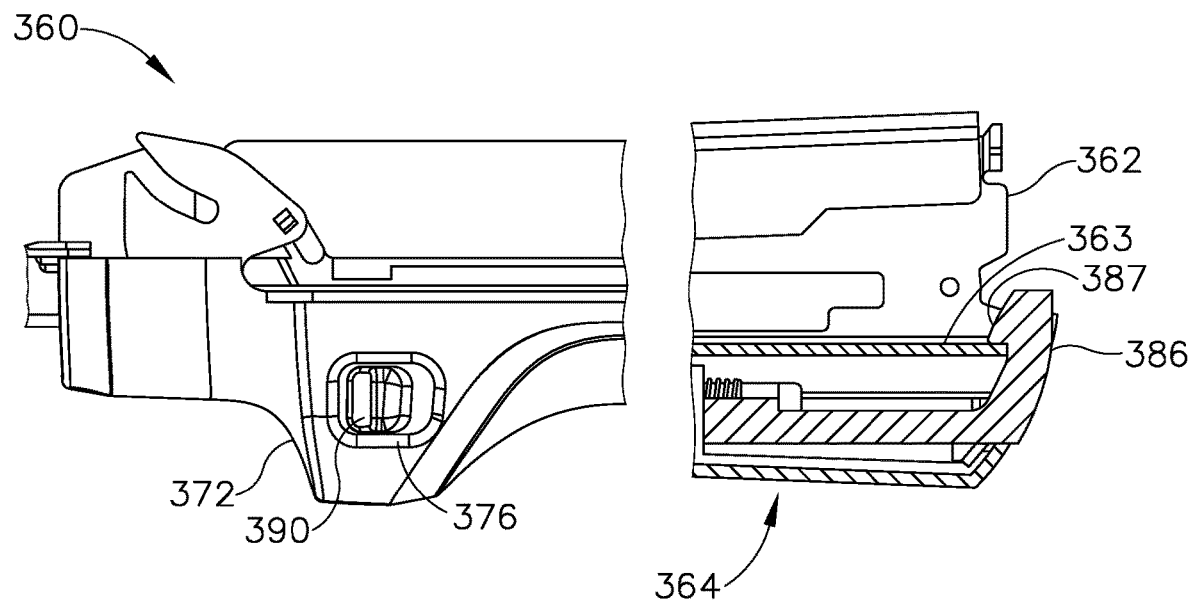
FIG. 19A depicts a combination side elevational view and side cross-sectional view of the cartridge half of FIG. 17, showing the shoulder latch mechanism resiliently biased in a distal home position in which a proximal latch member of the mechanism couples the clamp lever with the cartridge channel.
Figure 19B:
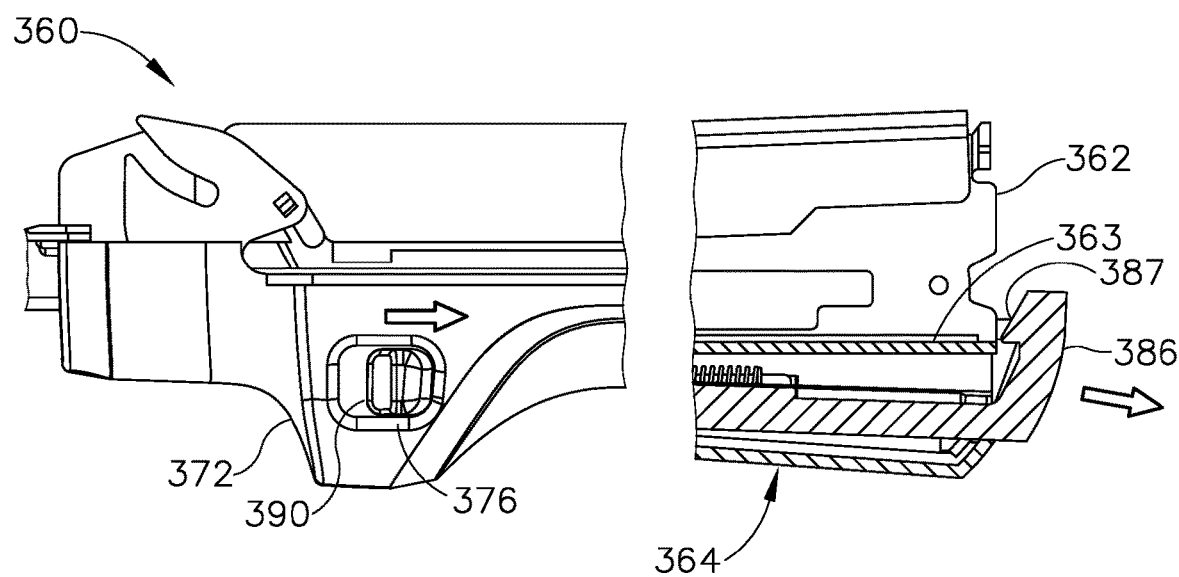
FIG. 19B depicts a combination side elevational view and side cross-sectional view of the cartridge half of FIG. 17, showing the shoulder latch mechanism actuated to a proximal position to disengage the proximal latch member from the cartridge channel and permit opening of the clamp lever.

As shown in FIGS. 19A and 19B, translating structure (382) of clamp lever latch mechanism (380) is configured to translate between a distal home position (FIG. 19A), and a proximal extended position (FIG. 19B). Compression spring (392) biases translating structure (382) toward the distal home position. During closure of clamp lever (364), a proximal cam surface (387) of latch finger (386) engages the proximal end of a base wall (363) of cartridge channel (362) and drives translating structure (382) proximally through proximal opening (378) of shroud (370). Upon clamp lever (364) reaching a fully closed position, translating structure (382) automatically returns to its distal home position via compression spring (392) so that proximal latch finger (386) hooks over and captures a proximal end of cartridge channel base wall (363), thereby releasably securing clamp lever (364) in the closed position. To release latch finger (386) from cartridge channel (362) and permit opening of clamp lever (364), an operator actuates knobs (390) proximally, which in turn drives latch finger (386) proximally via actuator arms (388) and central body (384).

IV. Exemplary Anvil Latch Member Having Anvil Pin Ejection Feature

As described above in connection with linear surgical stapler (200), anvil latch member (262) of proximal retaining assembly (260) of cartridge half (202) is configured to releasably capture proximal anvil pin (280) of anvil half (204) to couple the proximal ends of stapler halves (202, 204) together, even while clamp lever (240) remains in a fully open position. Release button (266) of retaining assembly (260) may then be actuated by an operator to disengage anvil latch member (262) from proximal anvil pin (280) and permit manual separation of stapler halves (202, 204) by the operator. In some instances, it may be desirable to configure the anvil latch member of a linear surgical stapler such that the release feature not only enables separation of the proximal ends of the stapler halves, but furthermore drives automatic separation of the proximal ends. The exemplary alternative anvil latch member (408) described below incorporates features that provide such functionality.

Figure 20:
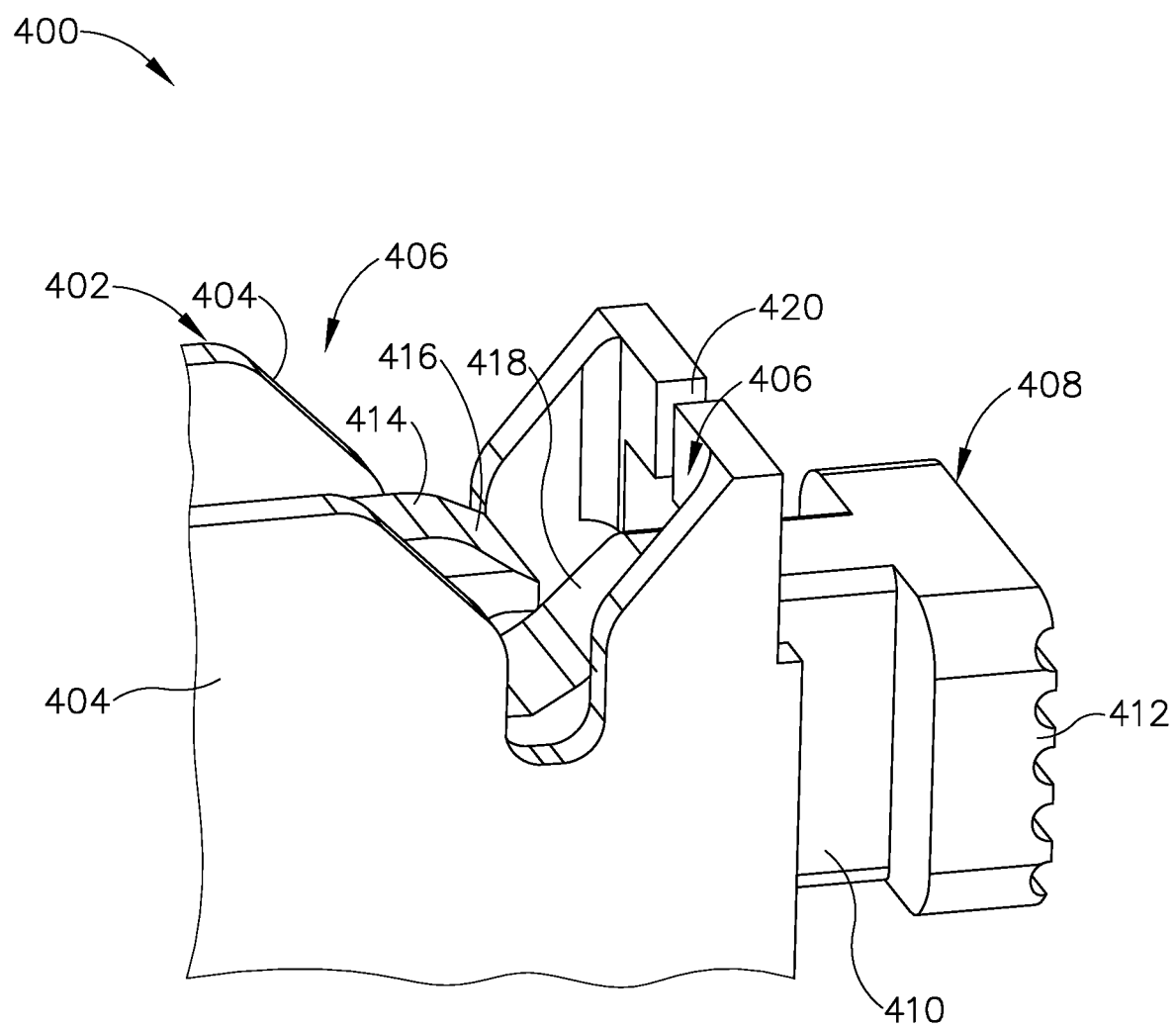
FIG. 20 depicts a perspective view of the proximal end of an exemplary cartridge channel and an anvil latch member coupled to the channel, showing the anvil latch member resiliently biased in a proximal home position.

FIG. 20 shows the proximal end of an exemplary cartridge half (400) that is similar to cartridge half (202) described above except as otherwise described below. Cartridge half (400) includes, among other components not shown, an elongate cartridge channel (402) having a proximal frame portion that includes a pair of upright side flanges (404). A pair of tapered notches (406) are formed in the proximal ends of upright side flanges (404) and are configured to receive a proximal pin (422) (see FIGS. 21A-21D) of an anvil half (not shown), which may be similar to anvil half (204) described above. Cartridge half (400) further includes an anvil latch member (408) moveably coupled to a proximal end of cartridge channel (402). Like anvil latch member (262) of stapler (200), anvil latch member (408) is configured to releasably couple the proximal end of cartridge half (400) with the proximal end of an anvil half (not shown).

Anvil latch member (408) of the present example includes a tab-like latch body (410), a transversely oriented release button (412) arranged at a proximal end of latch body (410), and a proximally facing latch finger (414) arranged at a distal end of latch body (410). An upper face of distal latch finger (414) defines a loading cam surface (416) that slopes proximally, and a distal face of latch body (410) defines an unloading cam surface (418) that slopes distally such that cam surfaces (416, 418) are sloped toward one another. Latch body (410) is configured to translate longitudinally through a slot (420) formed in the proximal end of cartridge channel (402), and a resilient member (not shown) is configured to bias anvil latch member (408) proximally. Slot (420) may be sized slightly larger than latch body (410) in a vertical direction to enable anvil latch member (408) to both translate and pivot relative to cartridge channel (402), as shown in FIGS. 21A-21C.

Figure 21A:
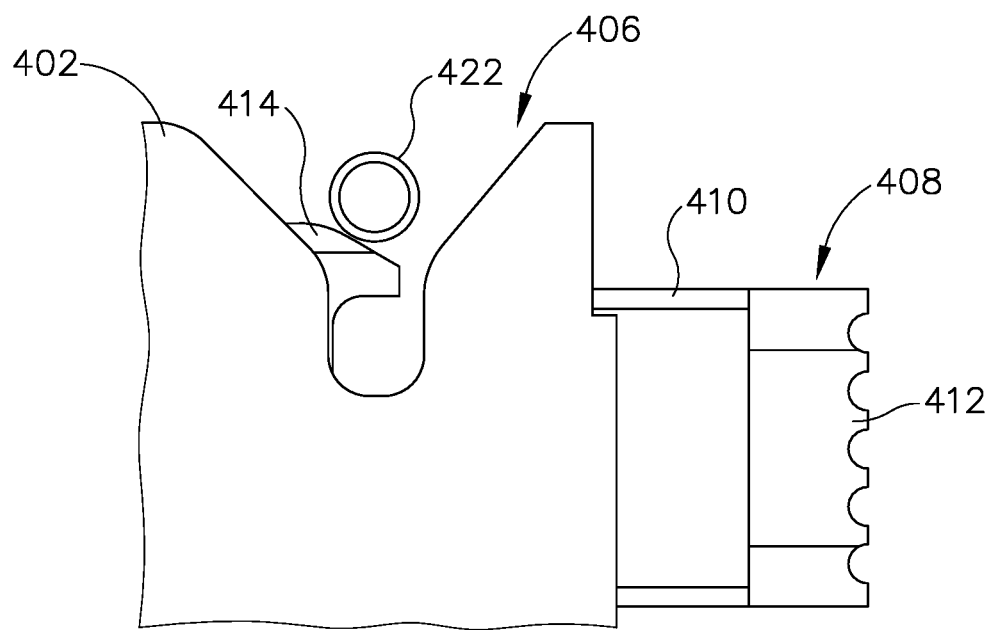
FIG. 21A depicts a side elevational view of the cartridge channel proximal end and anvil latch member of FIG. 20, showing the proximal pin of an anvil half of a linear surgical stapler being brought into engagement with an upper cam surface of the anvil latch member.
Figure 21B:
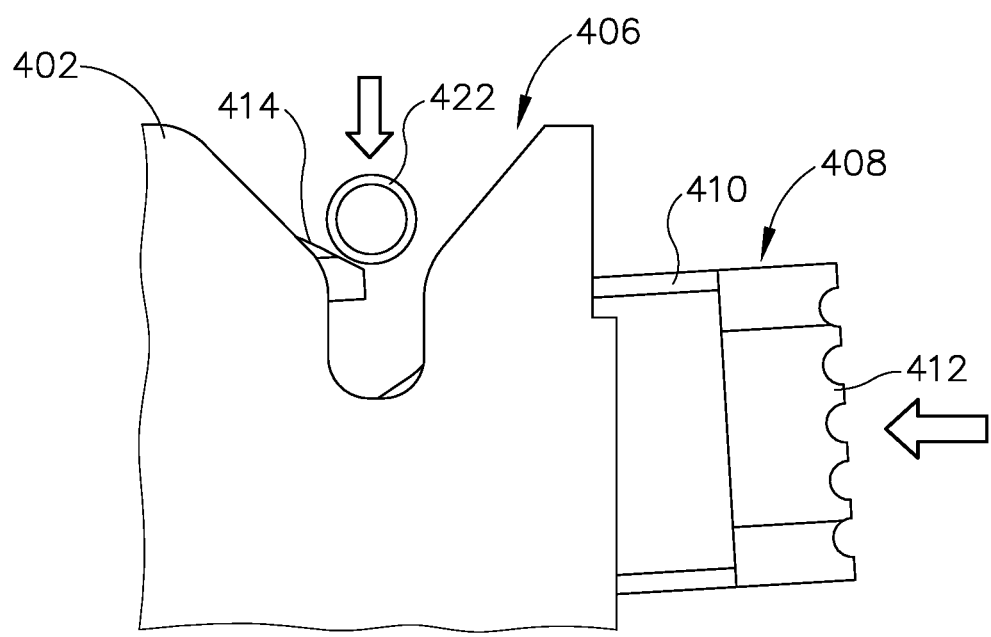
FIG. 21B depicts a side elevational view of the cartridge channel proximal end and anvil latch member of FIG. 20, showing the proximal anvil pin being directed into proximal notches of the cartridge channel to drive the anvil latch member distally via the upper cam surface.
Figure 21C:
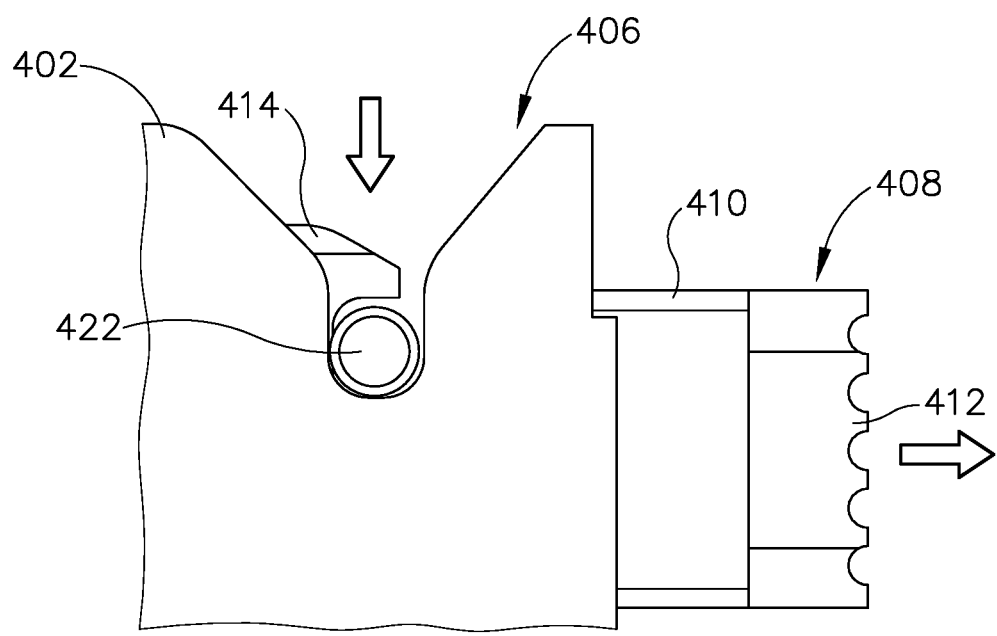
FIG. 21C depicts a side elevational view of the cartridge channel proximal end and anvil latch member of FIG. 20, showing the proximal anvil pin captured by the anvil latch member.
Figure 21D:
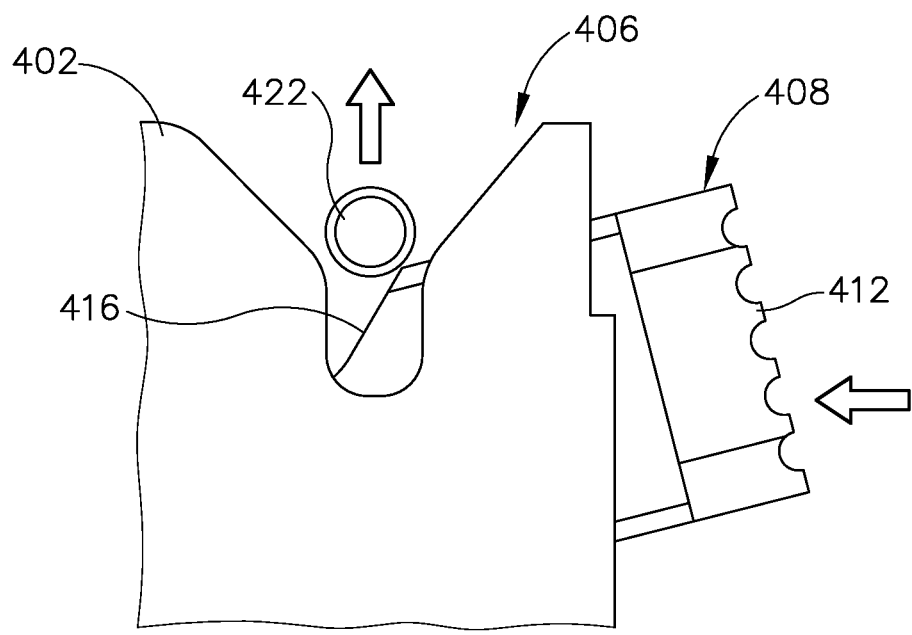
FIG. 21D depicts a side elevational view of the cartridge channel proximal end and anvil latch member of FIG. 20, showing the anvil latch member being depressed distally to eject the proximal anvil pin from the anvil latch member and the cartridge channel notches.

FIGS. 21A-21C show exemplary coupling and decoupling of the proximal end of an anvil half (not shown) having a proximal pin (422), with the proximal end of cartridge half (400). As shown in FIG. 21A, the proximal end of the anvil half is aligned with the proximal end of cartridge half (400) so as to direct proximal anvil pin (422) into channel notches (406) and into engagement with loading cam surface (416) of latch finger (414). As shown in FIG. 21B, this engagement drives anvil latch member (408) distally against the bias of its resilient member (not shown), until anvil pin (422) is captured by latch finger (414) as shown in FIG. 21C. The proximal ends of cartridge half (400) and the anvil half are now coupled together such that the anvil half may pivot relative to cartridge half (400) about proximal anvil pin (422). To separate the proximal ends of the stapler halves from one another, release button (412) of anvil latch member (408) is depressed distally by an operator as shown in FIG. 21D. This actuation causes anvil latch member (408) to simultaneously translate and pivot distally such that unloading cam surface (418) drives anvil pin (422) upwardly and ejects pin (422) from proximal notches (406) of cartridge channel (402). In this manner, the proximal end of the anvil half is automatically separated from the proximal end of cartridge half (400) upon actuation of release button (412), without requiring the operator to manually pull the stapler halves apart to release anvil pin (422) from cartridge channel (402).

V. Exemplary Alternative Anvil Halves Having Rotating Distal Anvil Pins

As described above in connection with linear surgical stapler (200), anvil shroud (300) includes features that facilitate assembly of the components of anvil half (204) and permit distal anvil pin (278) to freely rotate during clamping of stapler halves (202, 204). As described below, FIGS. 22A-26F show additional exemplary anvil halves (430, 500, 530) suitable for use with cartridge half (202) and having exemplary alternative features configured to permit rotation of a distal anvil pin during clamping of the stapler halves.

A. Exemplary Anvil Half Having Anvil Channel with Longitudinal Keyhole Slot

FIGS. 22A-24B show an exemplary anvil half (430) that is similar to anvil half (204) described above except as otherwise described below. Anvil half (430) includes, among other components, an elongate anvil channel (432) having a proximal frame portion (434) and a distal jaw portion (436). Proximal frame portion (434) includes a laterally opposed pair of upright side flanges (438) that are configured to be received between the side flanges of a cartridge half, such as cartridge half (202) described above, when anvil half (430) is coupled with the cartridge half. Anvil half (430) further includes a distal coupling member in the form of a laterally extending distal pin (440), and a proximal coupling member in the form of a laterally extending proximal pin (442) (see FIG. 24A). As described below, anvil pins (440, 442) are configured to secure an anvil shroud (456) to anvil channel (432), in addition to being configured to facilitate coupling of anvil half (430) with a cartridge half in the manner described above in connection with stapler (200).

Figure 22A:
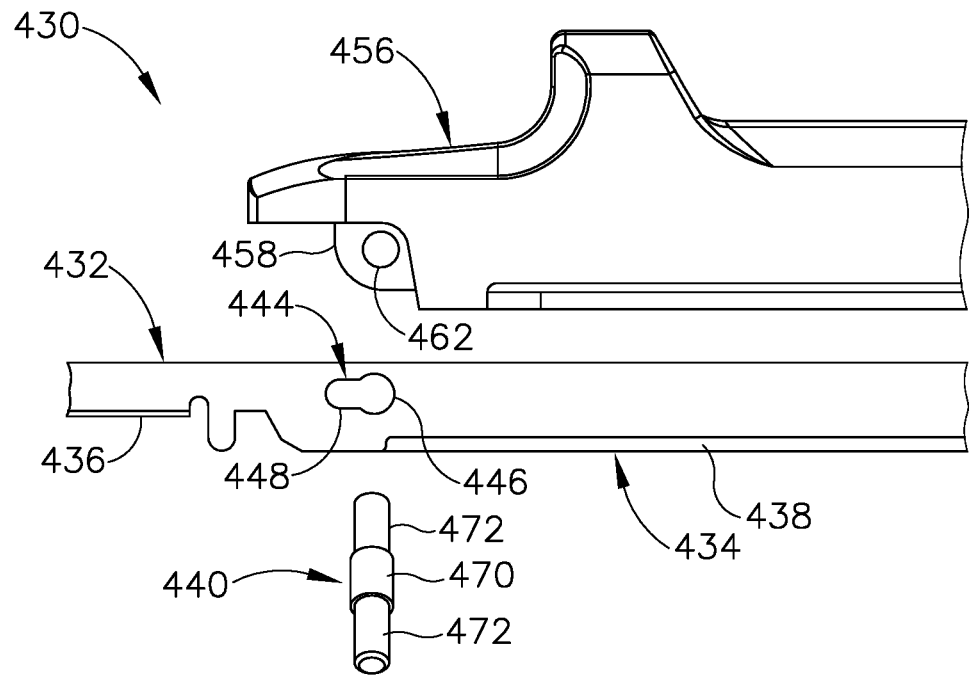
FIG. 22A depicts a side elevational view of components of another exemplary anvil half of a linear surgical stapler, showing an anvil shroud, an anvil channel, and a distal anvil pin separated from one another prior to assembly.

As shown in FIG. 22A, anvil channel (432) further includes a pair of keyhole slots (444) that are oriented longitudinally on the distal ends of side flanges (438) and are configured to receive distal anvil pin (440) laterally therethrough with a slip fit. Each keyhole slot (444) includes a circular entry portion (446) oriented proximally and an elongate retaining portion (448) oriented distally, such that keyhole slots (444) extend parallel to a longitudinal axis of anvil channel (432). Anvil channel (432) further includes a pair of proximal openings (450) (see FIG. 24A) that are arranged at the proximal ends of side flanges (438) and are configured to receive proximal anvil pin (442) laterally therethrough.

Figure 23:
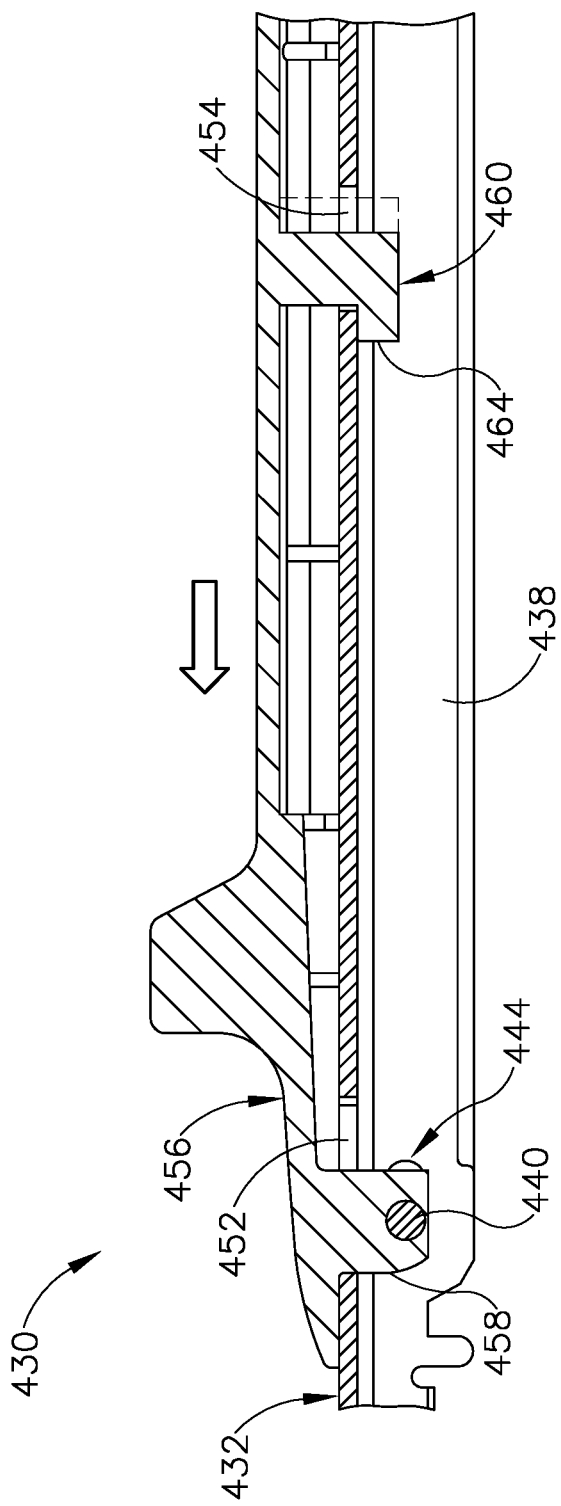
FIG. 23 depicts a side cross-sectional view of the anvil half components of FIG. 22A, showing the anvil shroud and distal anvil pin in the distal position relative to the anvil channel.
Figure 24A:
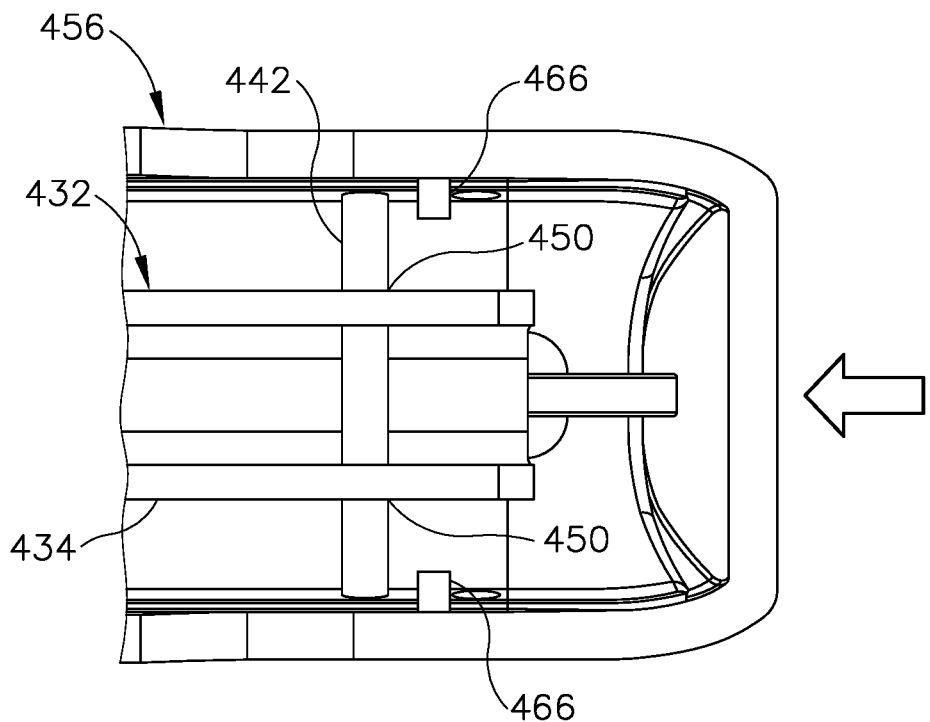
FIG. 24A depicts a bottom plan view of proximal ends of the anvil channel, anvil shroud, and a proximal anvil pin of the anvil half of FIG. 22A, showing the anvil shroud in a proximal position relative to the anvil channel and the proximal anvil pin during assembly.

As shown in FIGS. 22A and 23, anvil shroud (456) includes a distal inner tab (458) and a proximal inner tab (460) (see FIG. 23) extending transversely toward anvil channel (432) along a longitudinal centerline of anvil shroud (456). Distal inner tab (458) includes a circular opening (462) configured to receive distal anvil pin (440) laterally therethrough with a slip fit. Proximal inner tab (460) is generally foot-shaped and has a distally extending tip (464). Tabs (458, 460) of anvil shroud (456) are configured to be received through and translate longitudinally within respective elongate slots (452, 454) formed in a base wall of anvil channel (432) (see FIG. 23). As shown in FIG. 24A, anvil shroud (456) further includes a pair of proximal projections (466) extending inwardly from the proximal ends of opposed inner walls of anvil shroud (456).

As shown in FIG. 22A, distal anvil pin (440) is in the form of a stepped pin having a medial shoulder (470) and a pair of cylindrical shafts (472) extending outwardly from either end of shoulder (470). Pin shoulder (470) is formed with a larger outer diameter than pin shafts (472) such that pin shoulder (470) defines a maximum outer diameter of distal anvil pin (440) and pin shafts (472) each define a minimum outer diameter of distal anvil pin (440). As seen in FIG. 24A, proximal anvil pin (442) of the present example is cylindrical with a non-stepped configuration.

Figure 22B:
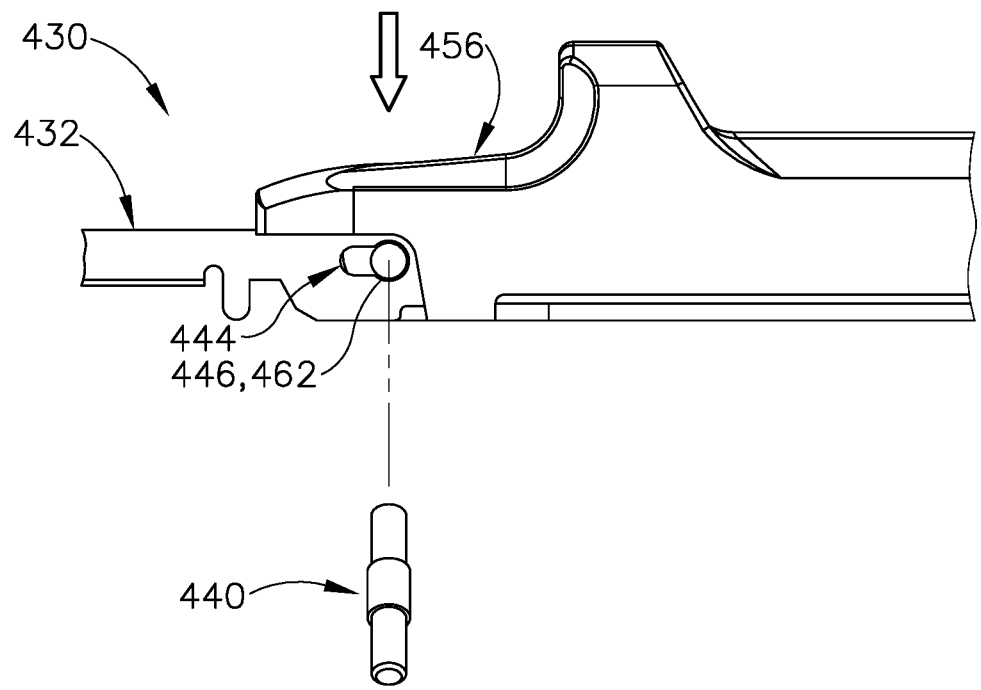
FIG. 22B depicts a side elevational view of the anvil half components of FIG. 22A during assembly, showing the anvil shroud applied to the anvil channel and the distal anvil pin being inserted laterally therethrough.

FIGS. 22A and 22B depict the components of anvil half (430) during an initial stage of assembly in which anvil shroud (456) is lowered onto anvil channel (432) such that distal inner tab (458) of anvil shroud (456) is received through distal anvil channel slot (452) and proximal inner tab (460) is received through proximal anvil channel slot (454). Anvil shroud (456) is positioned proximally relative to anvil channel (432) such that circular entry portions (446) of keyhole slots (444) on anvil channel (432) align with circular opening (462) on distal inner tab (458) of anvil shroud (456). Distal anvil pin (440) is then inserted laterally through circular entry portions (446) and circular opening (462) such that pin shoulder (470) resides within circular opening (462). The insertion of distal anvil pin (440) operates to secure the distal end of anvil shroud (456) transversely relative to anvil channel (432). Though not shown, proximal anvil pin (442) is inserted laterally through proximal openings (450) of anvil channel (432) prior to mounting anvil shroud (456) to anvil channel (432).

Figure 22C:
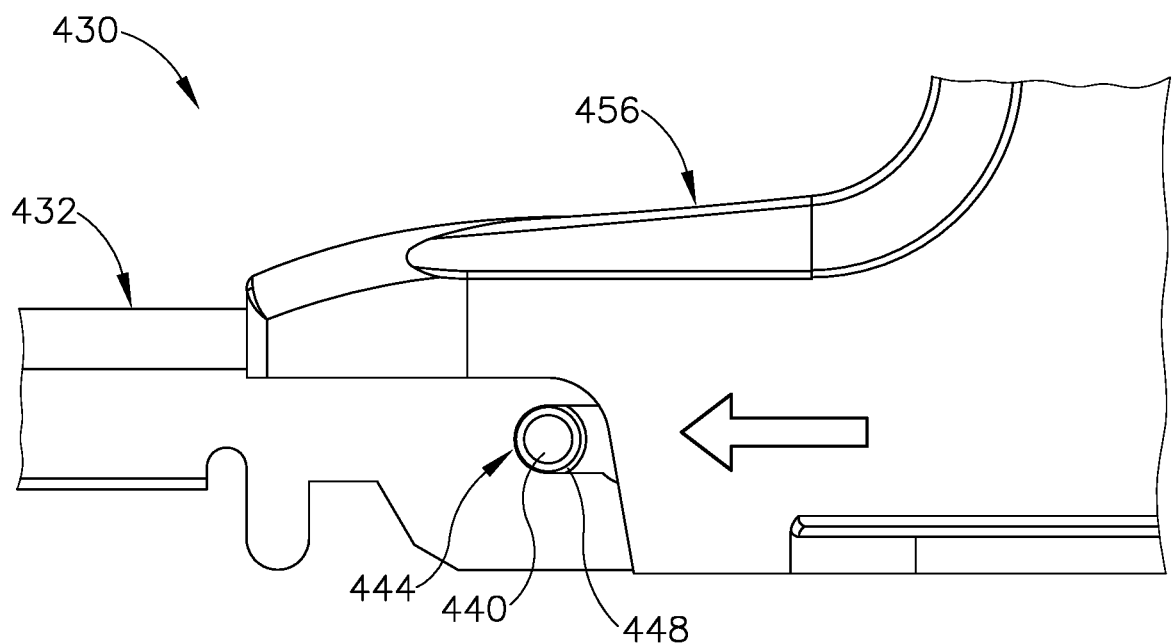
FIG. 22C depicts a side elevational view of the anvil half components of FIG. 22A, showing the anvil shroud and distal anvil pin translated to a distal position relative to the anvil channel.
Figure 22D:
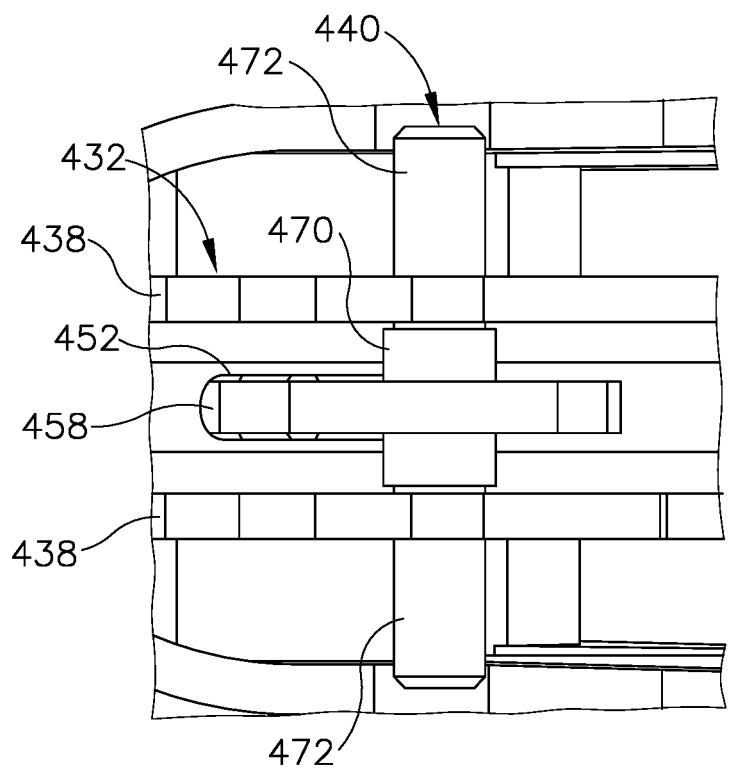
FIG. 22D depicts a bottom plan view of the anvil half components of FIG. 22A, showing the distal anvil pin constrained laterally relative to the anvil channel and the anvil shroud with the anvil shroud and distal anvil pin in the distal position.
Figure 24B:
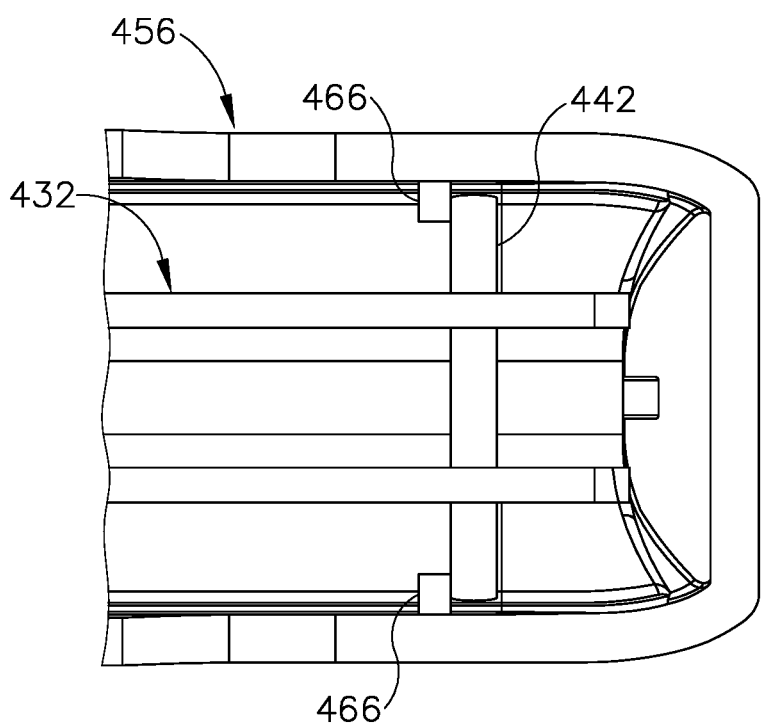
FIG. 24B depicts a bottom plan view of the anvil half components of FIG. 24A, showing the anvil shroud in the distal position relative to the anvil channel and the proximal anvil pin upon completion of assembly.

As shown in FIG. 22C, anvil shroud (456) and distal anvil pin (440) are then translated distally relative to anvil channel (432) such that pin shafts (472) are received within elongate retaining portions (448) of keyhole slots (444) on anvil channel (432). Pin shoulder (470) is sized larger than elongate retaining portions (448) such that distal anvil pin (440) becomes constrained laterally relative to anvil channel (432) and anvil shroud (456) as a result of the distal translation of anvil shroud (456) and distal anvil pin (440), as shown in FIG. 22D. As shown in FIGS. 23 and 24A-24B, the distal translation of anvil shroud (456) operates to advance additional features of anvil shroud (456) relative to anvil channel (432). In particular, as shown in FIG. 23, distal tip (464) of proximal inner tab (460) is advanced distally beyond a distal end of proximal anvil channel slot (454), thus securing the proximal end of anvil shroud (456) transversely relative to anvil channel (432). Additionally, as shown in FIGS. 24A and 24B, proximal inner projections (466) of anvil shroud (456) are advanced distally over and beyond the lateral ends of proximal anvil pin (442) in a detent-like engagement, thereby securing anvil shroud (456) longitudinally relative to anvil channel (432).

Accordingly, following the steps shown in FIGS. 22A-24B, the components of anvil half (430) are fully assembled such that distal anvil pin (440) is constrained laterally while still being permitted to rotate relative to anvil channel (432) and anvil shroud (456). As described above in connection with anvil half (204), such rotatability of distal anvil pin (440) provides friction-reducing advantages when clamping of anvil half (430) against a corresponding cartridge half of a linear surgical stapler.

Figure 25A:
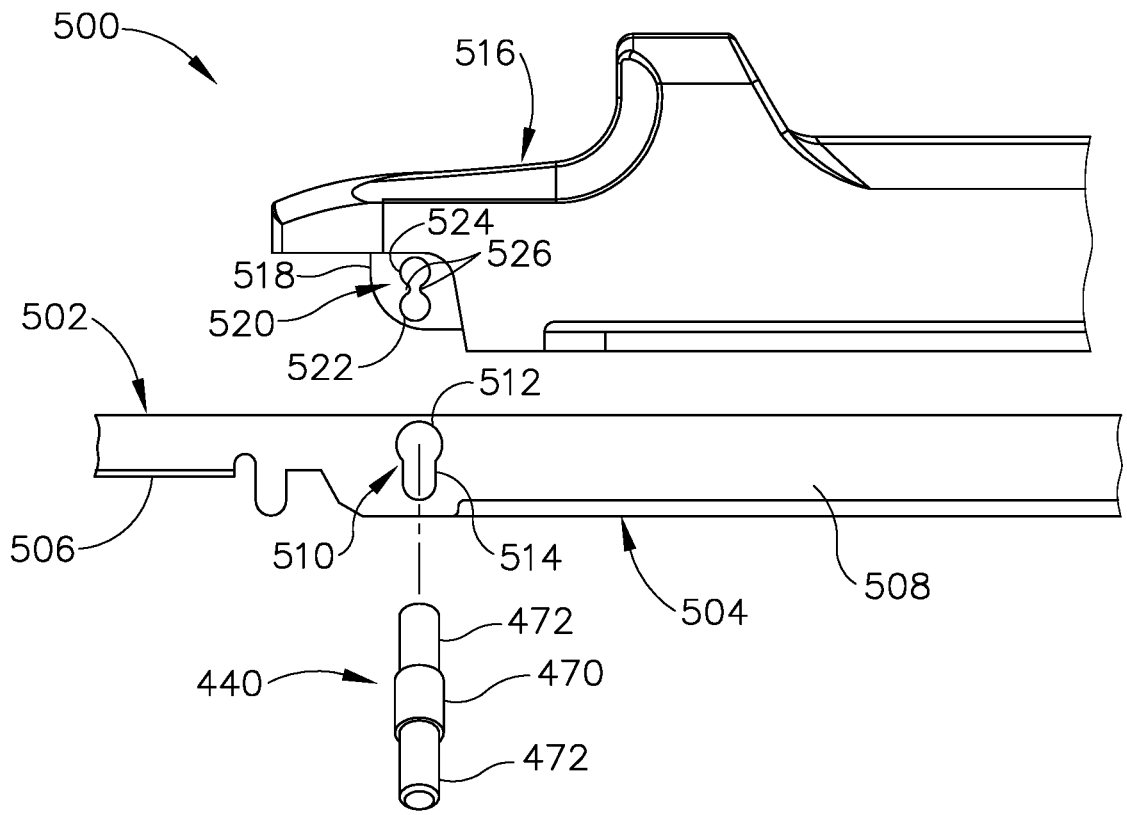
FIG. 25A depicts a side elevational view of components of another exemplary anvil half of a linear surgical stapler, showing an anvil shroud, an anvil channel, and a distal anvil pin separated from one another prior to assembly.
Figure 25B:
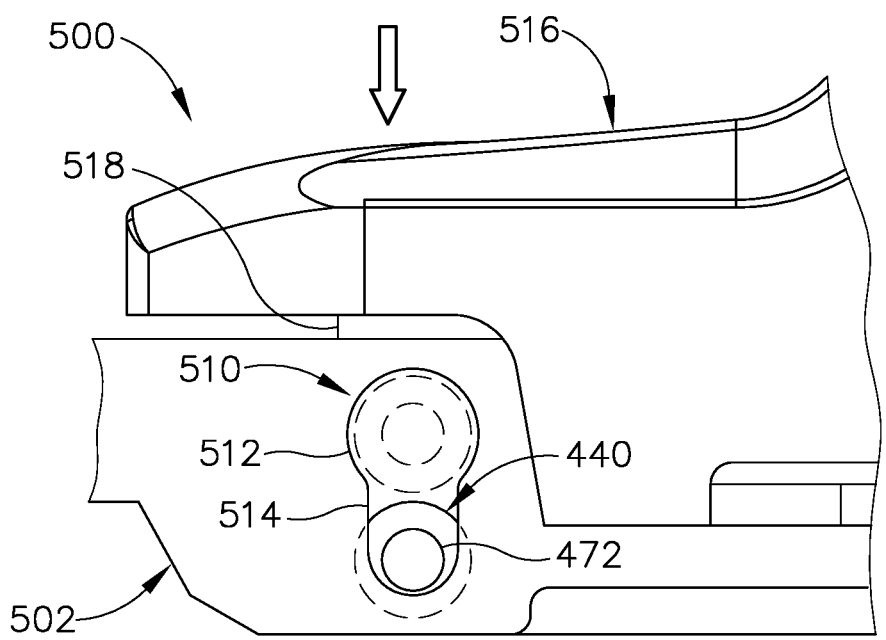
FIG. 25B depicts a side elevational view of the anvil half components of FIG. 25A during assembly, showing the anvil shroud applied to the anvil half and the distal anvil pin inserted laterally therethrough, showing the anvil shroud in a first, raised transverse position relative to the anvil channel.
Figure 25C:
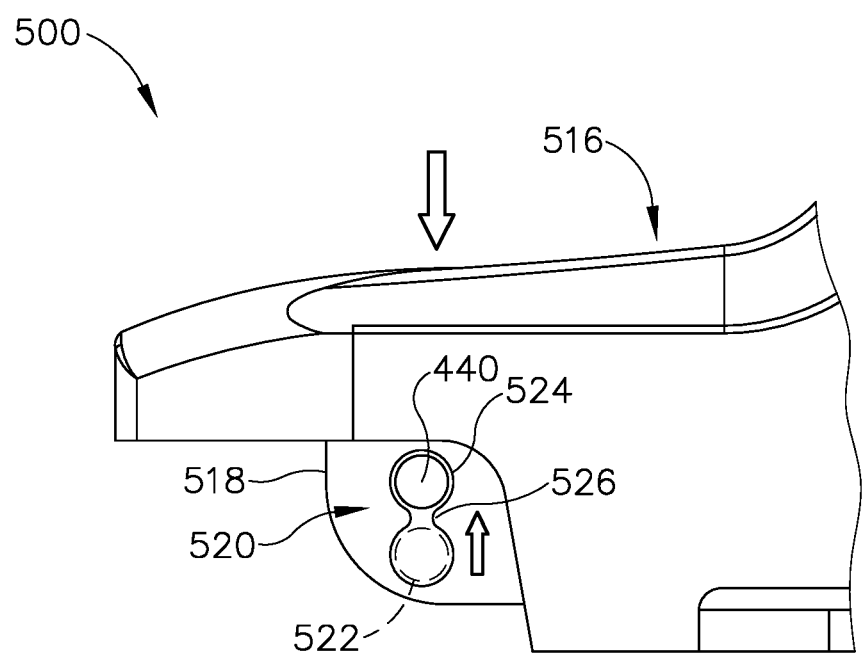
FIG. 25C depicts a schematic side elevational view of the anvil shroud and the distal anvil pin of the anvil half of FIG. 25A, with the anvil channel omitted from view, showing the position of the distal anvil pin within a slot of the anvil shroud when the anvil shroud is in a second, lowered transverse position relative to the anvil channel.

B. Exemplary Anvil Half Having Anvil Channel with Transverse Keyhole Slot and Anvil Shroud with Transverse Detented Slot FIGS. 25A-25C show another exemplary anvil half (500) that is similar to anvil halves (204, 430) described above except as otherwise described below. Anvil half (500) includes, among other components, an elongate anvil channel (502) having a proximal frame portion (504) and a distal jaw portion (506). Proximal frame portion (504) includes a laterally opposed pair of upright side flanges (508) that are configured to be received between side flanges of a cartridge half, such as cartridge half (202) described above, when anvil half (500) is coupled with the cartridge half. Anvil half (500) further includes a distal coupling member in the form of stepped distal anvil pin (440), described above. Though not shown, anvil half (500) further includes a proximal coupling member in the form of a laterally extending proximal pin, which may be similar to proximal anvil pins (280, 442) described above. Distal anvil pin (440) and the proximal anvil pin are configured to secure an anvil shroud (516) to anvil channel (502), in addition to being configured to facilitate coupling of anvil half (500) with a cartridge half in the manner described above in connection with stapler (200).

As shown in FIG. 25A, anvil channel (502) further includes a pair of keyhole slots (510) that are oriented transversely on the distal ends of side flanges (508) and are configured to receive distal anvil pin (440) laterally therethrough with a slip fit. Each keyhole slot (510) includes a circular entry portion (512) oriented toward a base wall of anvil channel (502), and an elongate retaining portion (514) oriented toward a free edge of the respective side flange (508). Anvil channel (502) further includes a pair of proximal openings (not shown), similar to proximal openings (288, 450), that are arranged at the proximal ends of side flanges (508) and are configured to receive the proximal anvil pin (not shown) laterally therethrough.

As shown in FIG. 25A, anvil shroud (516) includes a distal inner tab (518) extending transversely toward anvil channel (502) and having a detented slot (520). Detented slot (520) includes a generally circular entry portion (522) and a generally circular retaining portion (524) separated from one another by a pair of detent bumps (526). Entry portion (522) and retaining portion (524) are each similar in size and are configured to receive distal anvil pin (440) therethrough with a slip fit. Entry and retaining portions (522, 524) cooperate to define a centerline of detented slot (520) that is oriented transversely to a longitudinal axis of anvil half (500). Accordingly, detented slot (520) and keyhole slots (510) of the present example are oriented parallel to one another, and transversely to a longitudinal axis of anvil half (500).

FIG. 25A depicts the components of anvil half (500) in an initial stage of assembly in which anvil shroud (516) is lowered onto anvil channel (502) such that entry portion (522) of detented slot (520) aligns with entry portions (512) of keyhole slots (510). Distal anvil pin (440) is then inserted laterally through entry portions (512, 522), as shown in FIG. 25A, and anvil shroud (516) is then lowered further relative to anvil channel (502) to seat pin shafts (472) within retaining portions (514) of keyhole slots (510). Consequently, distal anvil pin (440) is now constrained laterally relative to anvil channel (502) and anvil shroud (516), and anvil shroud (516) is secured longitudinally relative to anvil channel (502).

To secure the distal end of anvil shroud (516) transversely relative anvil channel (502), anvil shroud (516) is pressed further transversely toward anvil channel (502). Distal anvil pin (440) resists further movement in this direction as a result of being seated within retaining portions (514) of keyhole slots (510). Accordingly, anvil shroud (516) advances transversely relative to distal anvil pin (440) such that pin shoulder (470) passes from entry portion (522) of detented slot (520), over detent bumps (526), and into retaining portion (524) of detented slot (520), as shown in FIG. 25C. Detent bumps (526) thus secure the proximal end of anvil shroud (516) transversely relative to anvil channel (502) while still permitting distal anvil pin (440) to freely rotate relative to anvil shroud (516) and anvil channel (502).

The proximal end of anvil shroud (516) may be secured to anvil channel (502) with a proximal anvil pin (not shown) in a manner similar to that described above in connection with anvil half (204).

Accordingly, following the steps shown in FIGS. 25A-25C, the components of anvil half (500) are fully assembled such that distal anvil pin (440) is constrained laterally while still being permitted to rotate relative to anvil channel (502) and anvil shroud (516). As described above in connection with anvil half (204), such rotatability of distal anvil pin (440) provides friction-reducing advantages when clamping of anvil half (500) against a corresponding cartridge half of a linear surgical stapler.

C. Exemplary Anvil Half Having Anvil Channel with Transverse Keyhole Slot and Anvil Shroud with Longitudinal Slot FIGS. 26A-26F show another exemplary anvil half (530) that is similar to anvil halves (204, 430, 500) described above except as otherwise described below. Anvil half (530) includes, among other components, an elongate anvil channel (532) having a proximal frame portion (534) and a distal jaw portion (536). Proximal frame portion (534) includes a laterally opposed pair of upright side flanges (538) that are configured to be received between the side flanges of a cartridge half, such as cartridge half (202) described above, when anvil half (530) is coupled with the cartridge half. Anvil half (530) further includes a distal coupling member in the form of stepped distal anvil pin (440) described above, and a proximal coupling member in the form of cylindrical proximal anvil pin (442) described above. Anvil pins (440, 442) are configured to secure an anvil shroud (550) to anvil channel (432), in addition to being configured to facilitate coupling of anvil half (530) with a cartridge half in the manner described above in connection with stapler (200).

Figure 26A:
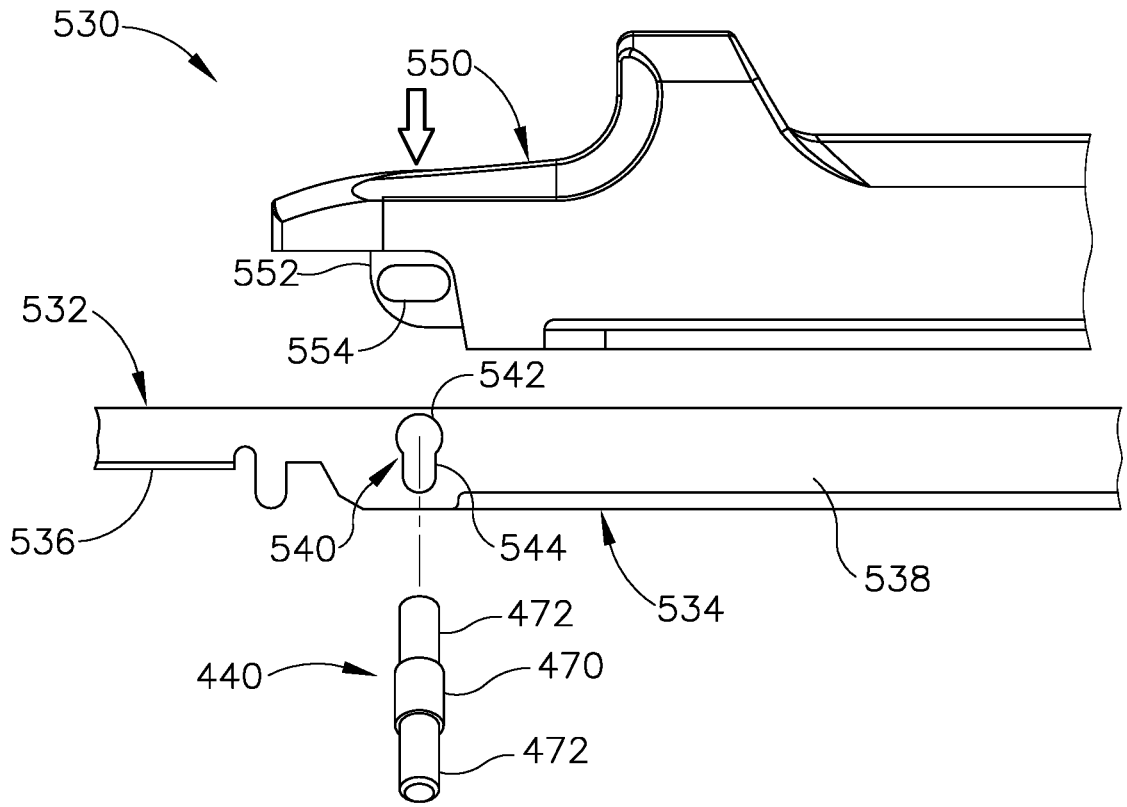
FIG. 26A depicts a side elevational view of components of another exemplary anvil half of a linear surgical stapler, showing an anvil shroud, an anvil channel, and a distal anvil pin separated from one another prior to assembly.

As shown in FIG. 26A, anvil channel (532) further includes a pair of keyhole slots (540) that are oriented transversely on the distal ends of side flanges (538) and are configured to receive distal anvil pin (440) laterally therethrough with a slip fit. Each keyhole slot (540) includes a circular entry portion (542) oriented toward a base wall of anvil channel (532), and an elongate retaining portion (544) oriented toward a free edge of the respective side flange (538). Anvil channel (532) further includes a pair of proximal openings (not shown), similar to proximal openings (288, 450) that are arranged at the proximal ends of side flanges (538) and are configured to receive proximal anvil pin (442) laterally therethrough. A base wall of anvil channel (532) includes a distal slot (not shown), similar to distal slot (290), configured to slidably receive a distal inner tab (552) of anvil shroud (550) therethrough, and a proximal slot (546) (see FIG. 26E) configured to slidably receive a proximal inner tab (556) of anvil shroud (550) therethrough.

As shown in FIG. 26A, distal inner tab (552) of anvil shroud (550) extends transversely toward anvil channel (532) and has a longitudinal slot (554) configured to receive distal anvil pin (440) laterally therethrough with a slip fit. As shown in FIG. 26E, proximal inner tab (556) of anvil shroud (550) extends transversely toward anvil channel (532) and has a circular opening (558). As shown in FIG. 26F, anvil shroud (550) further includes a pair of proximal openings (560) extending laterally through opposed sidewalls of anvil shroud (550). In the present example, proximal openings (560) are formed with hexagonal shapes. Circular opening (558) of proximal inner tab (556) and proximal openings (560) of the shroud sidewalls are aligned with one another and are configured to receive proximal anvil pin (442) laterally therethrough with an interference fit.

Figure 26B:
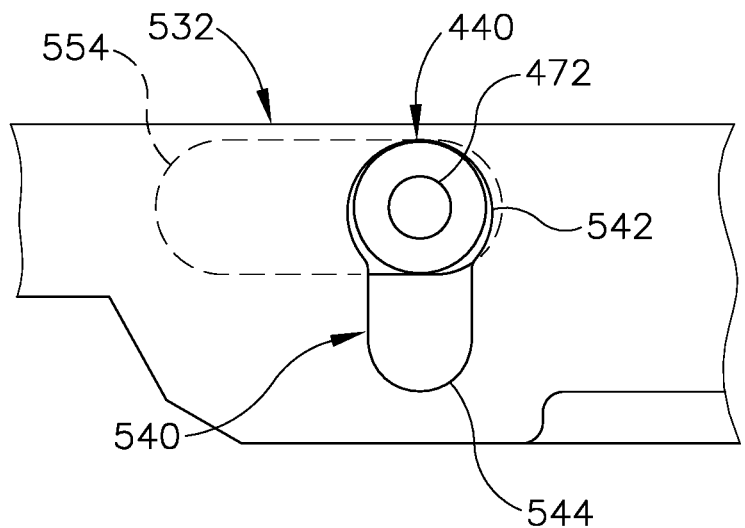
FIG. 26B depicts a schematic side elevational view of the anvil channel and distal anvil pin of FIG. 26A during assembly, showing the distal anvil pin in a first transverse position relative to the anvil channel.
Figure 26C:
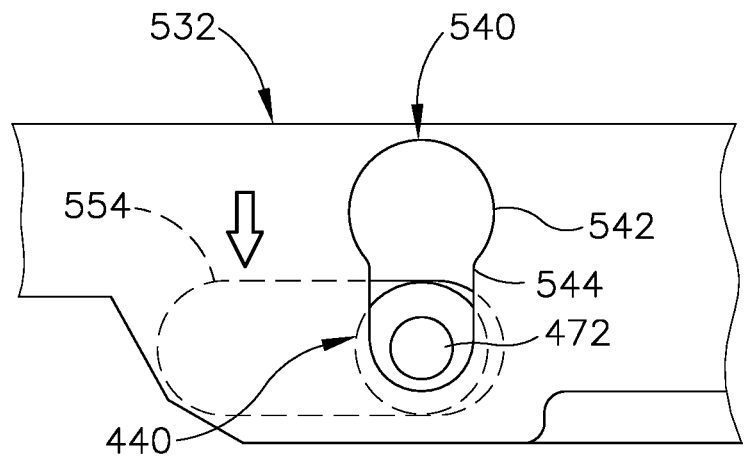
FIG. 26C depicts a schematic side elevational view of the anvil channel and distal anvil pin of FIG. 26A, showing the distal anvil pin in a second transverse position relative to the anvil channel and showing the anvil shroud in an initial distal position relative to the anvil channel and the distal anvil pin.
Figure 26D:
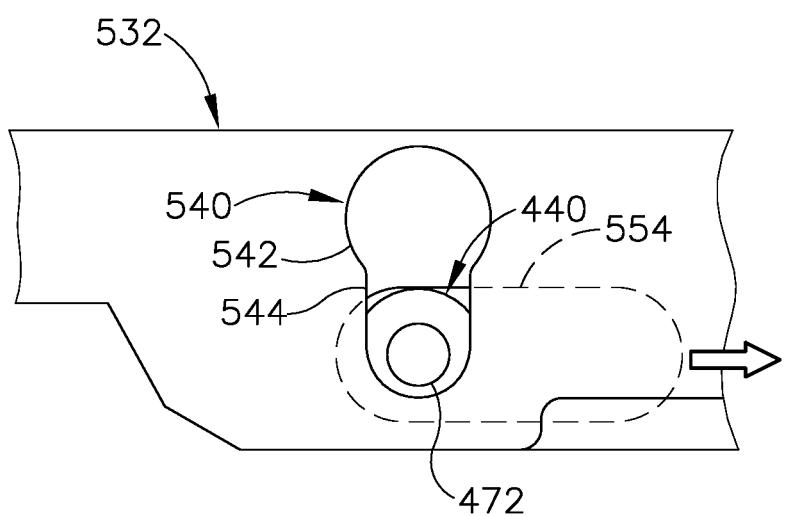
FIG. 26D depicts a schematic side elevational view of the anvil channel and distal anvil pin of FIG. 26A, showing the anvil shroud in a final proximal position relative to the anvil channel and the distal anvil pin.
Figure 26E:
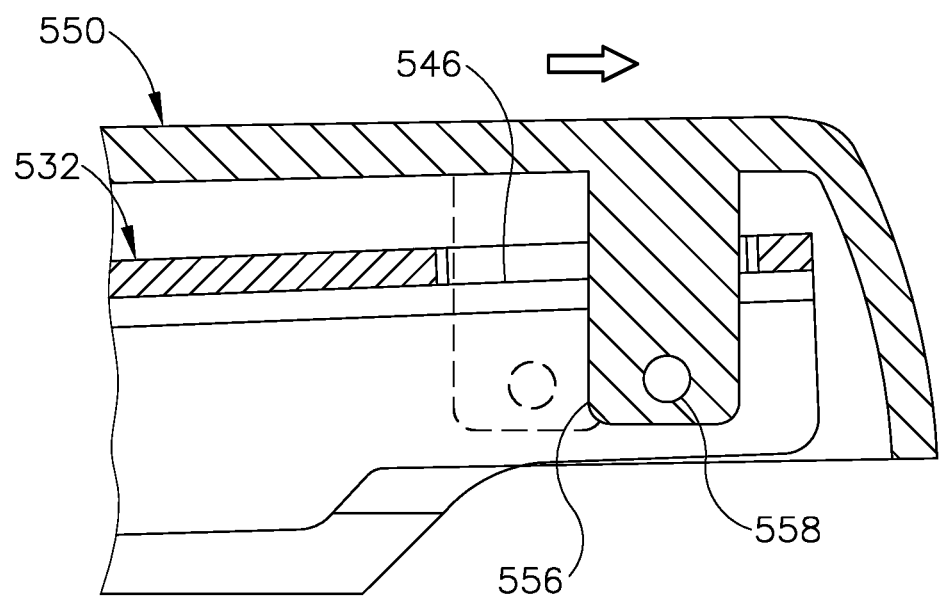
FIG. 26E depicts a side cross-sectional view of proximal ends of the anvil channel and anvil shroud of FIG. 26A, showing the anvil shroud translated to the final proximal position relative to the anvil channel.
Figure 26F:
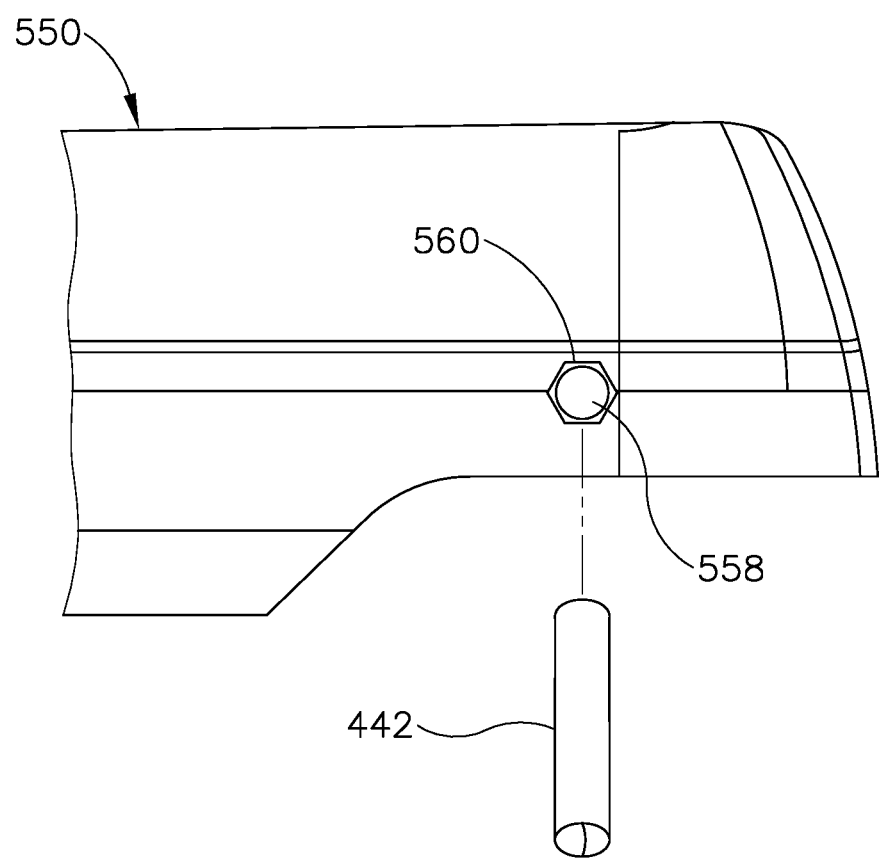
FIG. 26F depicts a side elevational view of the proximal ends of the anvil shroud and the anvil channel in the configuration of FIG. 26E, showing insertion of a proximal anvil pin through the anvil shroud and anvil channel.

FIGS. 26A and 26B depict the components of anvil half (530) in an initial stage of assembly in which anvil shroud (550) is lowered onto anvil channel (532) such that distal inner tab (552) is received through the distal slot (not shown) of anvil channel (532). Anvil shroud (550) is initially positioned such that longitudinal slot (554) of distal inner tab (552) is aligned with circular entry portions (542) of keyhole slots (540) of anvil channel (532). Distal anvil pin (440) is then inserted laterally through circular entry portions (542) and longitudinal slot (554), as shown in FIG. 26B. As shown in FIG. 26C, anvil shroud (550) is lowered further to seat pin shafts (472) within lower retaining portions (544) of keyhole slots (540), thereby constraining distal anvil pin (440) laterally relative to anvil channel (532) and anvil shroud (550). As shown in FIGS. 26D-26F, anvil shroud (550) is then translated proximally relative to anvil channel (532) to align opening (558) of proximal inner tab (556) and proximal openings (560) of the sidewalls of shroud (550) with the proximal openings (not shown) of anvil channel (532). As shown in FIG. 26F, proximal anvil pin (442) is then inserted laterally through the anvil and shroud openings (558, 560), thereby securing anvil shroud (550) longitudinally and transversely relative to anvil channel (532).

Accordingly, following the steps shown in FIGS. 26A-26F, the components of anvil half (530) are fully assembled such that distal anvil pin (440) is constrained laterally while still being permitted to rotate relative to anvil channel (532) and anvil shroud (550). As described above in connection with anvil half (204), such rotatability of distal anvil pin (440) provides friction-reducing advantages when clamping of anvil half (530) against a corresponding cartridge half of a linear surgical stapler.

VI. Exemplary Linear Surgical Stapler with Clamp Lever Lockout Member Coupled to Cartridge Channel As described above in connection with linear surgical stapler (200), clamp lever latch member (250) and proximal hook (268) of retaining assembly (260) are configured to releasably lock clamp lever (240) in the closed position. In some instances, it may be desirable to provide stapler (200) with an alternative feature operable to releasably lock clamp lever (240) in the fully open position until stapler halves (202, 204) are properly aligned with one another. The exemplary linear surgical stapler (600) described below in connection with FIGS. 27-29C includes such a clamp lever lockout member (640), which is operable to prevent closure of clamp lever (618) until stapler halves (602, 604) are properly aligned to ensure that distal anvil pin (636) is effectively captured by clamp lever jaws (622).

Linear surgical stapler (600) is generally similar to linear surgical stapler (200) described above except as otherwise described below. Moreover, any one or more features of stapler (600), such as lockout member (640), may be implemented with stapler (200) or any of other exemplary stapler halves disclosed herein. Similar to stapler (200), stapler (600) includes a cartridge half (602) and an anvil half (604) configured to releasably couple together to clamp tissue therebetween. Cartridge half (602) includes an elongate cartridge channel (606) having a proximal frame portion (608) configured to slidably house a firing assembly (not shown), which may be similar to firing assembly (224), and a distal jaw portion (610) configured to receive a staple cartridge (not shown), which may be similar to staple cartridge (230). Proximal frame portion (608) includes a laterally opposed pair of upright side flanges (612), a pair of vertical slots (614) arranged in the distal ends of side flanges (612), and a pair of tapered notches (616) arranged in the proximal ends of side flanges (612). Cartridge half (602) further includes a clamp lever (618) pivotably coupled to proximal frame portion (608). Clamp lever (618) includes an elongate lever arm (620) and a pair of laterally opposed jaws (622) extending distally from a distal end of elongate lever arm (620). Each jaw (622) includes a curved jaw slot (624) defining upper and lower camming surfaces.

Anvil half (604) of linear surgical stapler (600) includes an elongate anvil channel (630) having a proximal frame portion (632) and a distal jaw portion (634) that supports an anvil surface (not shown) configured to deform staples ejected by the staple cartridge (not shown). Anvil half (604) further includes a distal coupling member in the form of a laterally extending distal pin (636), and a proximal coupling member in the form of a laterally extending proximal pin (638). Though not shown, stapler (600) may further include a plurality of shrouds, such as a clamp lever shroud and an anvil shroud similar to clamp lever shroud (254) and anvil shroud (300) described above, for example.

Cartridge half (602) of stapler (600) further includes a clamp lever lockout member (640) pivotably coupled to a distal end of a cartridge channel side flange (612) via outwardly projecting support tabs (642) arranged proximally of vertical slots (614). Clamp lever lockout member (640) is configured to pivot about a horizontal axis, which extends parallel to a longitudinal axis of cartridge channel (606), to prevent closure of clamp lever (618) until stapler halves (602, 604) are properly aligned with one another, as described in greater detail below.

Figure 29A:
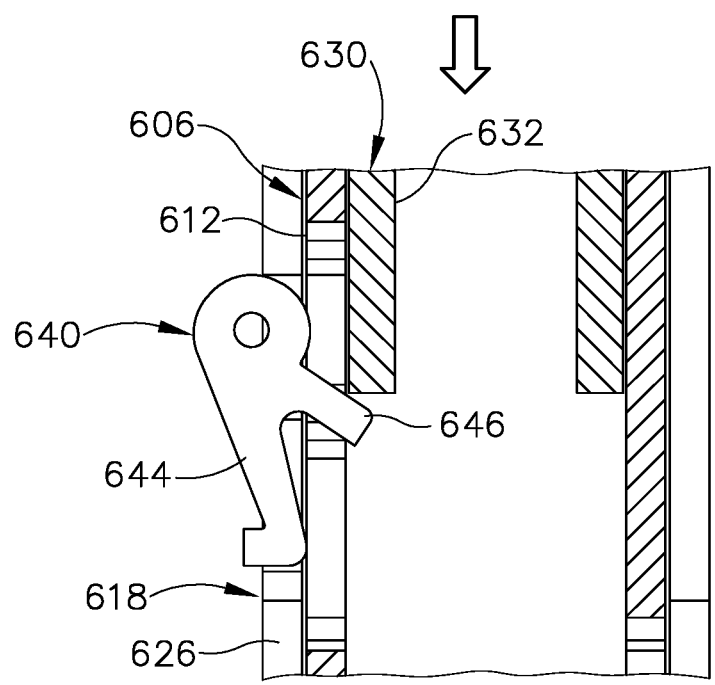
FIG. 29A depicts an end cross-sectional view of the surgical stapler of FIG. 27, taken along line 29A-29A in FIG. 27, showing the lockout member in a lockout position in which the lockout member prevents the clamp lever from closing.
Figure 29B:
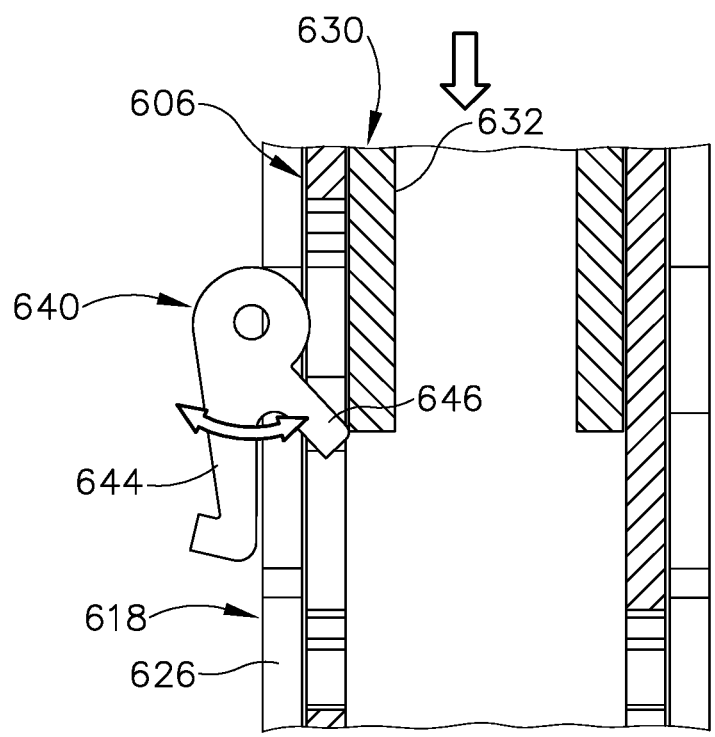
FIG. 29B depicts an end cross-sectional view of the surgical stapler of FIG. 27, taken along line 29A-29A in FIG. 27, showing the lockout member after having been actuated to a release position by a side flange of the anvil half.
Figure 29C:
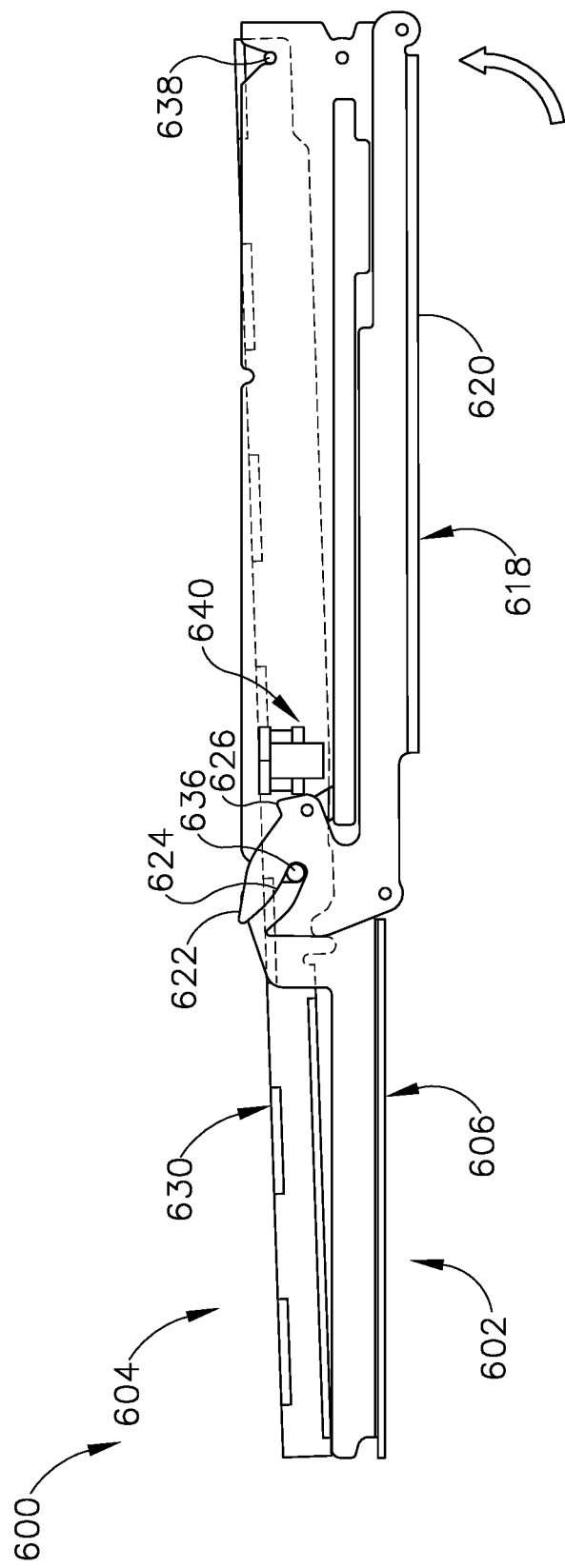
FIG. 29C depicts a side elevational view of the linear surgical stapler of FIG. 29A, showing the clamp lever pivoted to the closed position following release of the clamp lever lockout member.

As shown best in FIGS. 29A and 29B, clamp lever lockout member (640) includes an outer arm (644) that extends along an exterior of cartridge channel side flange (612), and an inner arm (646) that is angled relative to outer arm (644) and extends into an interior of cartridge channel (606). As shown in FIGS. 27 and 29A, outer arm (644) is configured to engage a jaw shoulder (626) of clamp lever (618) and hold clamp lever (618) in the fully open position such that the open distal ends of jaw slots (624) remain aligned with vertical slots (614) of cartridge channel (606). Inner arm (646) of lockout member (640) is configured to be engaged by proximal frame portion (632) of anvil channel (630) when anvil half (604) is initially received by cartridge half (602). Specifically, as shown in FIGS. 29A and 29B, engagement of anvil proximal frame portion (632) with inner arm (646) causes lockout member (640) to pivot outwardly such that outer arm (644) disengages jaw shoulder (626) and permits clamp lever (618) to be closed, as shown in FIG. 29C. In this manner, clamp lever lockout member (640) ensures that clamp lever (618) may be closed only once distal anvil pin (636) of anvil half (604) has been received by vertical slots (614) of cartridge channel (606) and jaw slots (624) of clamp lever (618), thereby preventing premature closure of clamp lever (618). Upon return of clamp lever (618) to the fully open position, lockout member (640) automatically returns to its lockout position to reengage jaw shoulder (626) in the manner described above.

VII. Linear Surgical Stapler Having Spring-Assisted Separation Feature

Figure 30:
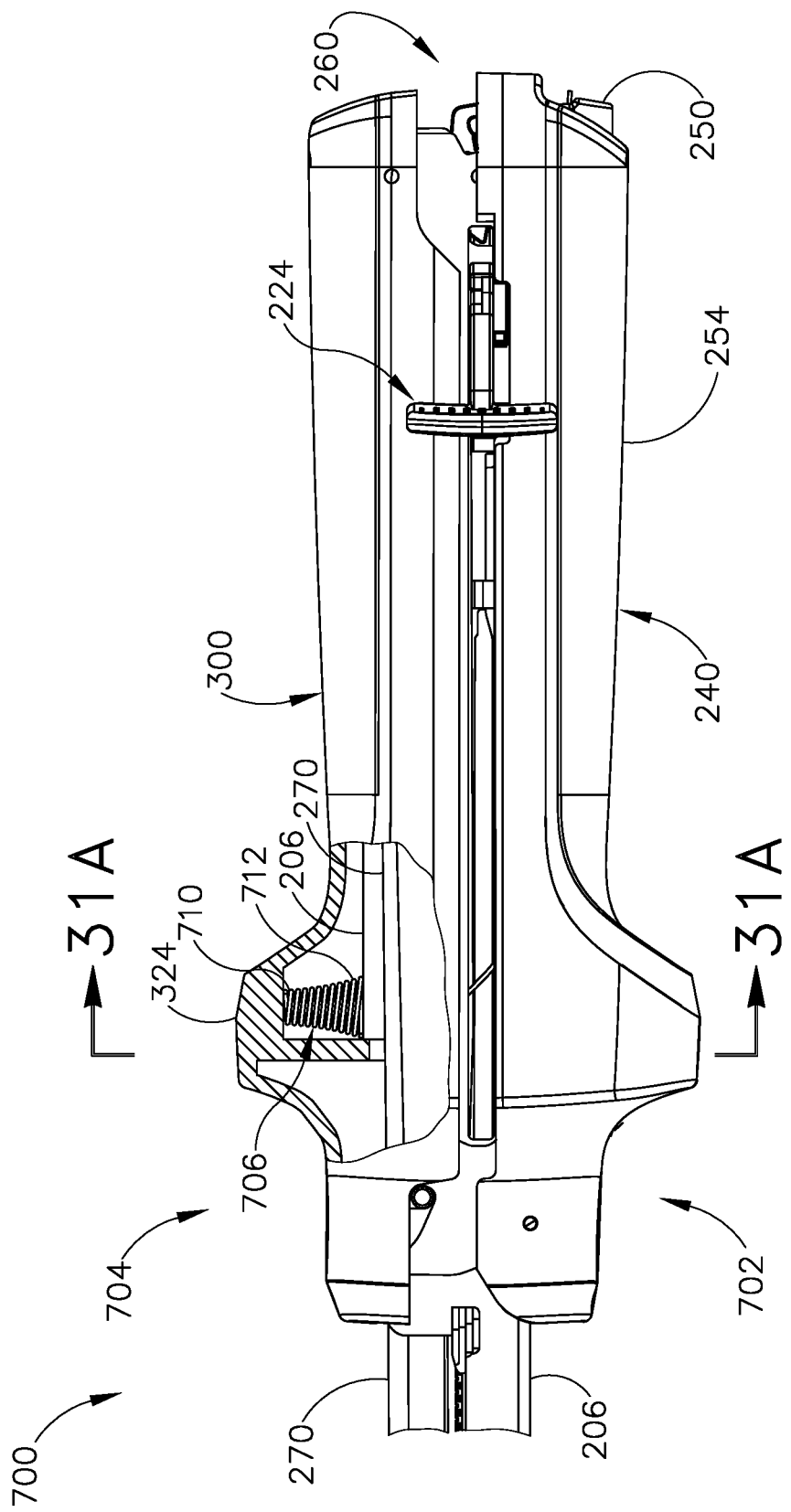
FIG. 30 depicts a perspective view of another exemplary linear surgical stapler, showing a portion of an anvil shroud cut away to reveal an inner resilient member.

A. Exemplary Configuration Having Resilient Member Housed within Distal Anvil Shoulder FIGS. 30-32 show another exemplary linear surgical stapler (700) having a cartridge half (702) and an anvil half (704) that are substantially similar to stapler halves (202, 204) described above, as indicated by use of like reference numerals in FIGS. 30-32, except as otherwise described below. In particular, stapler halves (702, 704) are resiliently biased away from one another to provide assisted separation of halves (702, 704) and enhanced one-handed usability of stapler (700), as described in greater detail below.

Anvil half (704) of linear surgical stapler (700) includes a resilient member shown in the form of a compression spring (706) housed within the interior of a distal shoulder (324) of anvil shroud (300). In the present version, the interior of shoulder (324) includes a post (708) that projects inwardly toward proximal frame portion (272) of anvil channel (270). An outer end (710) of spring (706) encircles post (708) and is thereby constrained relative to anvil shroud (300), and a free inner end (712) of spring (706) extends transversely toward proximal frame portion (272) of anvil channel (270). As shown in FIG. 31B, inner spring end (712) is configured to confront an outer surface of the base wall of anvil channel (270) when spring (706) is in a relaxed stated. Post (708) may be formed integrally with anvil shroud (300) or otherwise rigidly connected to shroud (300). In some versions, post (708) may be omitted and outer spring end (710) may be secured directly to anvil shroud (300). In other versions, compression spring (706) may be substituted with various alternative types of resilient members readily apparent to those of ordinary skill in the art in view of the teachings herein, such as a leaf spring or a wave spring, for example.

Figure 31A:
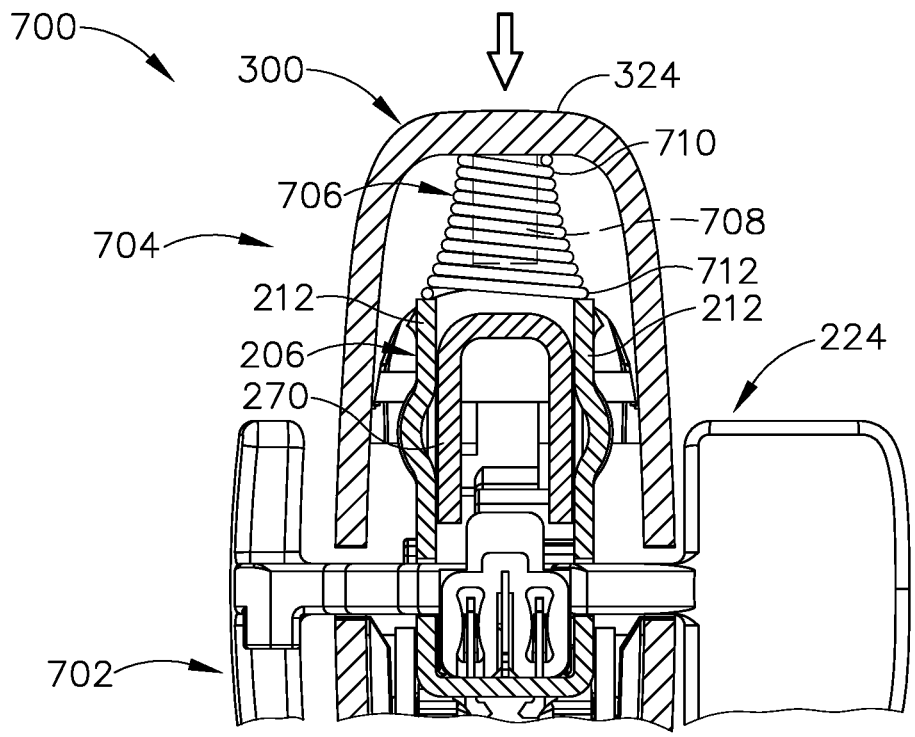
FIG. 31A depicts an end cross-sectional view of the surgical stapler of FIG. 30, taken along line 31A-31A, showing the resilient member in a compressed state when a clamp lever of the stapler is closed.
Figure 31B:
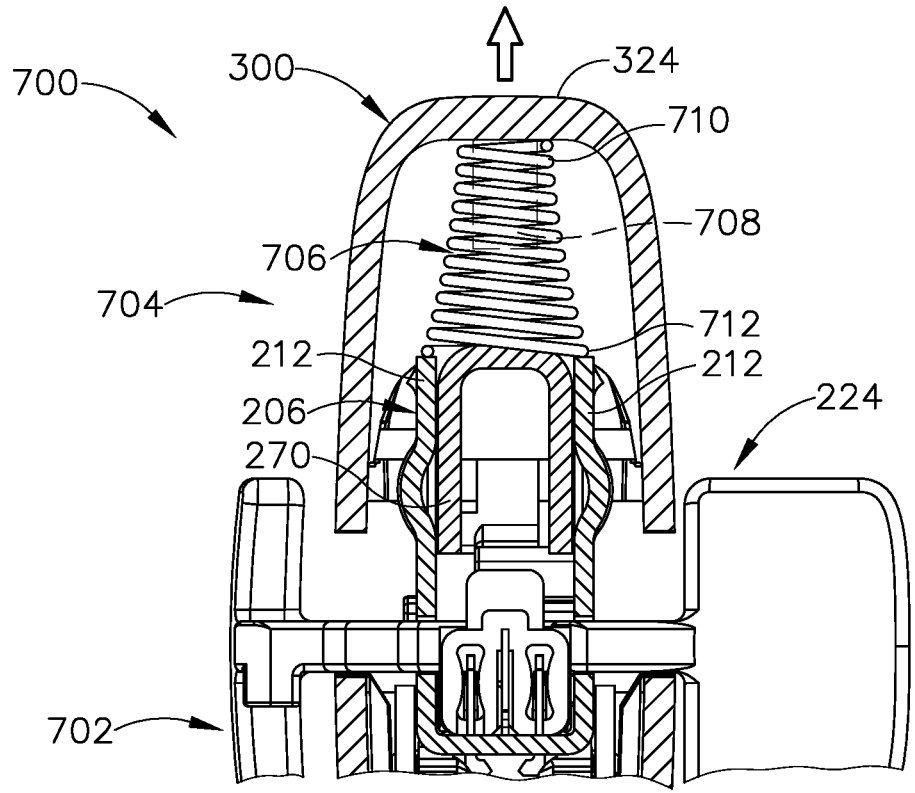
FIG. 31B depicts an end cross-sectional view of the surgical stapler of FIG. 30, taken along line 31A-31A, showing the resilient member in an expanded state when the clamp lever is open.
Figure 32:
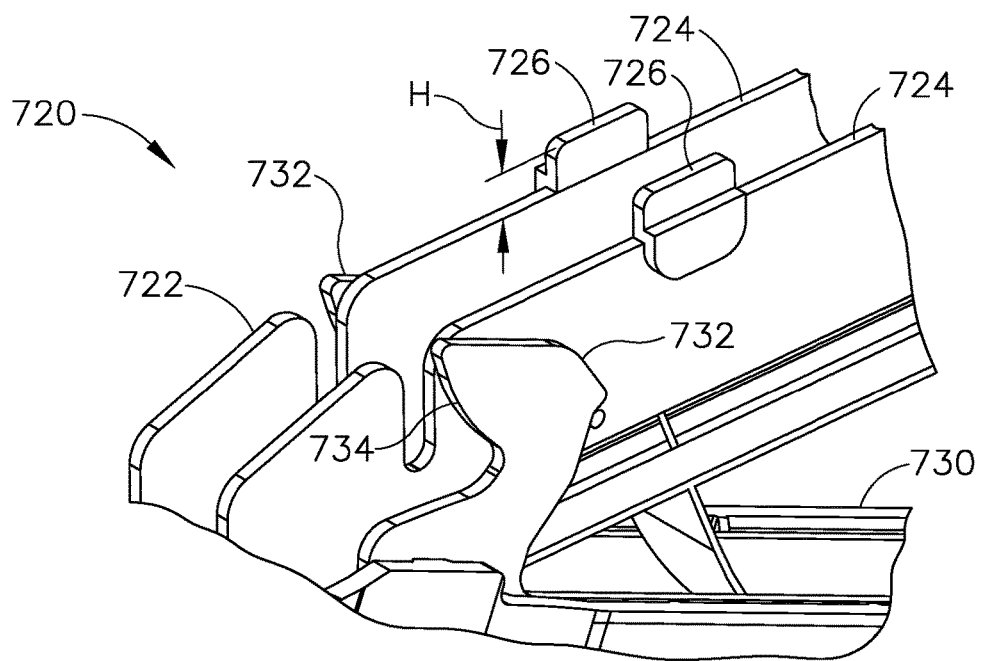
FIG. 32 depicts an enlarged perspective view of an exemplary alternative cartridge half suitable for use with the anvil half of the surgical stapler of FIG. 30.

As shown in FIGS. 31A and 31B, inner end (712) of compression spring (706) defines a spring width that is greater than a width of proximal frame portion (272) of anvil channel (270), and greater than or equal to a width of proximal frame portion (208) of cartridge channel (206). In the present version, inner spring end (712) flares outwardly relative to outer spring end (710), though in other versions spring (706) may be formed with a constant outer diameter. Accordingly, inner spring end (712) is configured to directly contact the upper surfaces of cartridge channel side flanges (212) when anvil half (704) is clamped against cartridge half (702) by closing clamp lever (240) in the manner described above in connection with stapler (200). Consequently, as shown in FIG. 31A, cartridge channel side flanges (212) compress inner spring end (712) toward outer spring end (710) when stapler halves (702, 704) are fully clamped together by clamp lever (240).

Figure 31C:
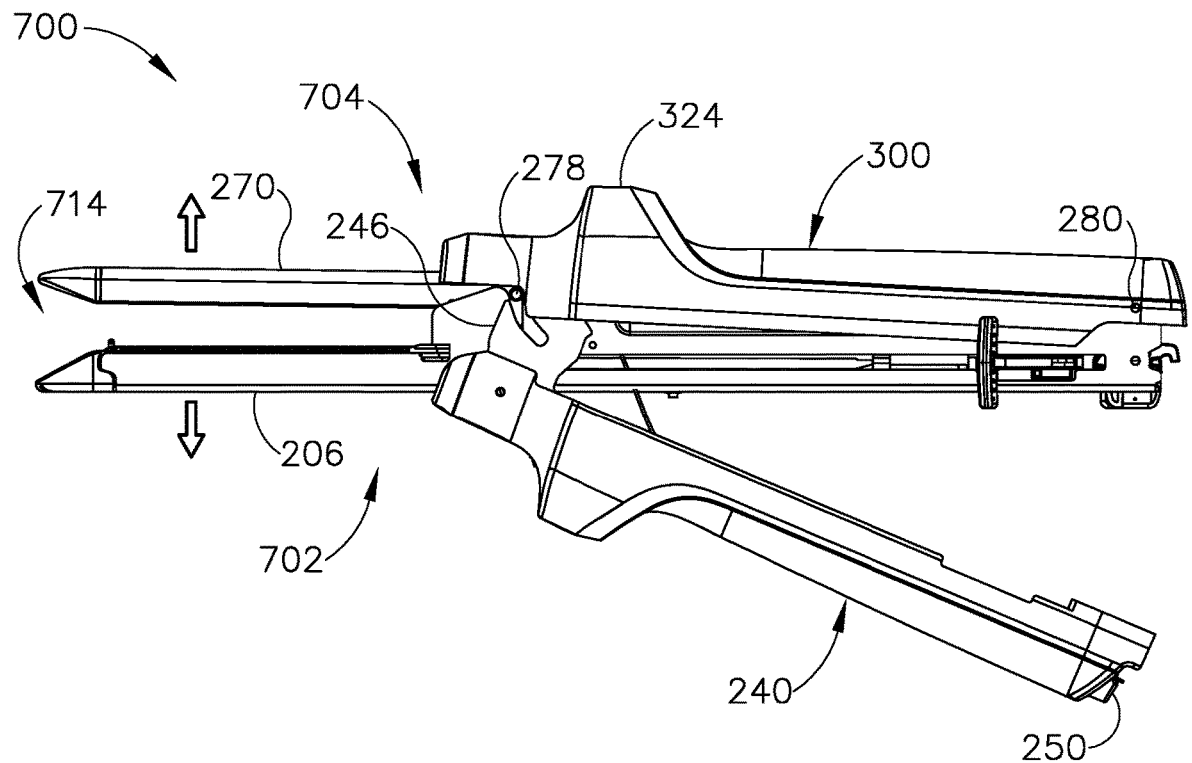
FIG. 31C depicts a side elevational view of the surgical stapler of FIG. 30, showing the clamp lever in the open position such that the resilient member can expand.

As shown in FIGS. 31B and 31C, upon clamp lever (240) being moved toward the open position such that clamp lever jaws (246) begin to release distal anvil pin (278), compression spring (706) decompresses and drives against cartridge channel side flanges (212) to push cartridge channel (206) away from anvil channel (270). In this manner, spring (706) urges stapler halves (702, 704) to pivot open about proximal anvil pin (280) such that a distal aperture (714) is formed between the distal portions of stapler halves (702, 704). Because stapler halves (702, 704) remain coupled together at their proximal ends via anvil latch member (262) (see FIGS. 16A-16D), the operator is enabled to easily remove tissue from staple halves (702, 704) while holding stapler (700) with a single hand.

FIG. 32 shows an exemplary alternative cartridge half (720) suitable for use with anvil half (704) of linear surgical stapler (700). Cartridge half (720) is similar to cartridge halves (202, 702) described above except as otherwise described below. Similar to cartridge halves (202, 702), cartridge half (720) includes an elongate cartridge channel (722) having a proximal frame portion with upright side flanges (724), and a clamp lever (730) pivotably coupled with cartridge channel (722). Cartridge half (720) further includes a pair of protrusions shown in the form of raised tabs (726) extending upwardly from distal portions of cartridge channel side flanges (724). Tabs (726) may be formed integrally with side flanges (724), or otherwise be rigidly coupled to side flanges (724). The upper end of each tab (726) is configured to engage a respective side of inner end (712) of compression spring (706) of anvil half (704) in a manner similar to side flanges (212) of cartridge channel (206). Each tab (726) is formed with a transverse height (H) above the upper edge of the respective cartridge channel side flange (724). Tab heights (H) may be selected to compress spring (706) by a predetermined amount when anvil half (704) is clamped against cartridge half (720), and thereby tune the resulting spring force exerted by compression spring (706) on cartridge channel (722). It will be appreciated that the selected tab heights (H) will also dictate a size of the resulting aperture defined between the distal ends of stapler halves (704, 720) when clamp lever (730) is opened, for example as seen in FIG. 31C.

As described above in connection with stapler (200), each jaw (246) of clamp lever (240) includes a curved slot (248) that defines first and second camming structures arranged on opposing sides of curved slot (248). The first (or proximal) camming structure defines a first camming surface configured to draw distal anvil pin (278) into jaw slot (248) and the respective cartridge channel distal slot (214) when clamp lever (240) is closed. The second (or distal) camming structure defines a second camming surface configured to eject distal anvil pin (278) from jaw slot (248) and the respective cartridge channel distal slot (214) when clamp lever (240) is opened.

Clamp lever (730) of cartridge half (720) differs from clamp lever (240) in that clamp lever (720) includes a pair of jaws (732) each having a single camming structure. The single camming structure defines a curved distal camming surface (734) configured to draw in distal anvil pin (278) for clamping an anvil half (204, 704) against cartridge half (720). This configuration of jaws (732), in which second camming structures are omitted, reduces the risk of a "friction-locking" scenario in which clamp lever (730) becomes stuck in the closed position, particularly when clamping tissues of greater thicknesses. Moreover, omission of the second camming structures on jaws (732) enables clamp lever (730) to more easily move toward the open position via the resilient bias of compression spring (706) when the proximal end of clamp lever (730) is decoupled from cartridge channel (722), for example via a clamp lever latch member similar to latch member (250) described above. Accordingly, jaws (732) are configured to enhance the spring-assisted separation of stapler halves (704, 720) provided by compression spring (706).

Figure 33:
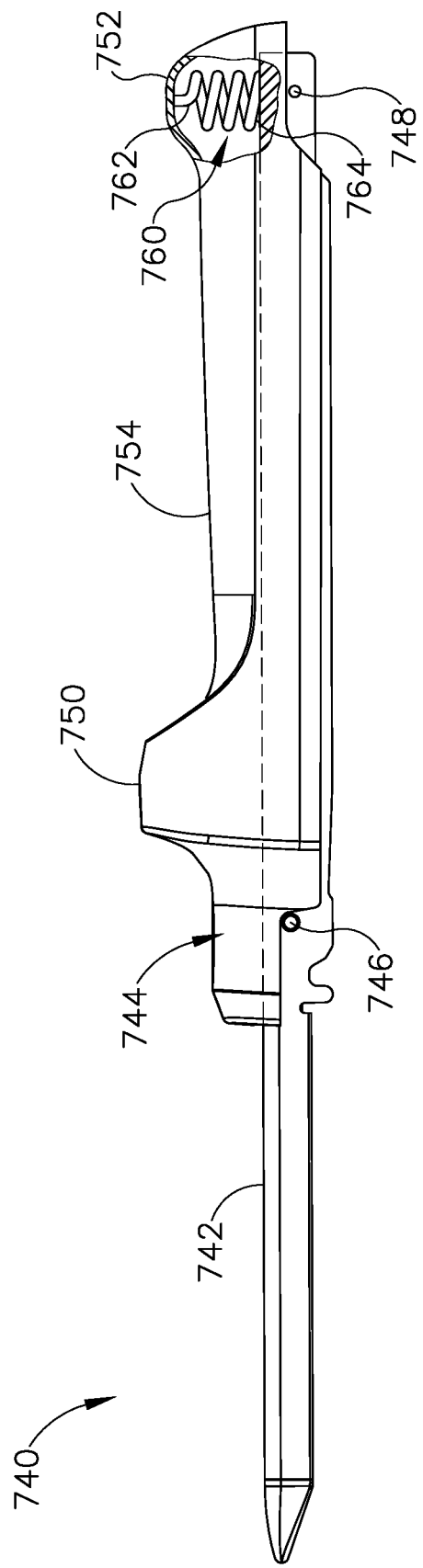
FIG. 33 depicts a side elevational view of an exemplary alternative anvil half having anvil shroud with a proximal gripping feature, showing the proximal gripping feature partially cut away to reveal a resilient member housed therein.

B. Exemplary Configuration Having Resilient Member Housed within Proximal Anvil Shoulder In some instances, it may be desirable to provide the anvil shroud of a linear surgical stapler with a proximal feature configured to provide the operator with enhanced grip of the stapler during use. FIG. 33 shows an exemplary alternative anvil half (740) configured in such a manner as described below, and which is suitable for use with any of the exemplary cartridge halves (202, 702, 720) described above. Anvil half (740) is similar to anvil halves (204, 704) in that anvil half (740) includes an elongate anvil channel (742) and an anvil shroud (744) secured to a proximal frame portion of anvil channel (742) with a distal anvil pin (746) and a proximal anvil pin (748).

Anvil shroud (744) is similar to anvil shroud (300) described above except as otherwise described below. Like anvil shroud (300), anvil shroud (744) includes a distal shoulder (750) arranged at a distal end of shroud (744). However, anvil shroud (744) further includes a proximal grip feature shown in the form of a second shoulder (752) arranged at a proximal end of shroud (744). Proximal shoulder (752) of the present example protrudes outwardly relative to a medial portion (754) of anvil shroud (744) and has a hollow interior similar to distal shoulder (750). In use, medial shroud portion (754) is configured to be gripped by the operator such that proximal shoulder (752) constrains the operator's hand proximally, for instance during distal firing of firing assembly (224), and distal shoulder (750) constrains the operator's hand distally, for instance during proximal retraction of firing assembly (224).

Anvil half (740) further includes a resilient member shown schematically in the form of a compression spring (760) that is similar in structure and function to compression spring (706) of anvil half (704) described above. In the present version, compression spring (760) is housed within the open interior of proximal shoulder (752) of anvil shroud (744) at a location just distally of proximal anvil pin (748). Compression spring (760) includes an outer end (762) that is fixed relative to anvil shroud (744), and a free inner end (764) that extends toward and confronts a proximal end of anvil channel (742). Inner spring end (764) is configured to directly contact and provide for resilient compression of spring (760) against upper surfaces of the proximal ends of cartridge channel side flanges (212, 724) when anvil half (740) is clamped against cartridge half (202, 702, 720). Accordingly, similar to compression spring (706) described above, compression spring (760) is configured to provide spring-assisted opening of anvil half (740) relative to a cartridge half (202, 702, 720) when clamp lever (240, 730) is opened.

Though not shown, it will be appreciated that in some versions raised tabs (726) of cartridge half (720) may be located proximally to interact with compression spring (760) of anvil half (740). Additionally, in some versions compression spring (760) may be housed within distal shoulder (750) of anvil shroud (744), similar to compression spring (760). In other versions, resilient members such as compression springs (706, 760) may be housed within both distal shoulder (750) and proximal shoulder (752).

VIII. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical stapler comprising: (a) a first elongate member having a distal portion that supports an anvil surface, wherein the anvil surface includes a plurality of staple forming pockets; (b) a second elongate member having a distal portion configured to receive a staple cartridge; (c) a pin rotatably coupled with the first elongate member; and (d) a clamp member movably coupled with the second elongate member, wherein the clamp member is operable to releasably capture the pin to thereby clamp the first elongate member against the second elongate member, wherein the pin is configured to rotate relative to the first elongate member in response to being captured by the clamp member.

Example 2

The surgical stapler of Example 1, wherein the pin comprises a stepped pin.

Example 3

The surgical stapler of any of the preceding Examples, wherein the pin includes a first cylindrical end portion, a second cylindrical end portion, and a medial portion extending therebetween, when the medial portion has a different outer diameter than the first cylindrical end portion and the second cylindrical end portion.

Example 4

The surgical stapler of any of the preceding Examples, further comprising a shroud configured to cover at least a portion of the first elongate member, wherein the pin couples the shroud with the first elongate member.

Example 5

The surgical stapler of Example 4, wherein the pin is configured to rotate relative to the shroud and the first elongate member in response to being captured by the clamp member.

Example 6

The surgical stapler of any of Examples 4 through 5, wherein the pin is arranged at a distal end of the shroud.

Example 7

The surgical stapler of Examples 4 through 6, further comprising a keyhole slot arranged on one of the shroud or the first elongate member, wherein the pin extends through the keyhole slot.

Example 8

The surgical stapler of Example 7, wherein the keyhole slot is configured to constrain the pin laterally relative to the shroud and the first elongate member.

Example 9

The surgical stapler of any of Examples 7 through 8, wherein the keyhole slot is configured to permit longitudinal movement of the shroud relative to the first elongate member during assembly thereof while the pin is positioned within the keyhole slot.

Example 10

The surgical stapler of any of Examples 7 through 9, wherein the keyhole slot is oriented parallel to a longitudinal axis of the first elongate member.

Example 11

The surgical stapler of any of Examples 7 through 9, wherein the keyhole slot is configured to permit transverse movement of the shroud relative to the first elongate member during assembly thereof while the pin is positioned within the keyhole slot.

Example 12

The surgical stapler of any of Examples 7 through 9 or Example 11, wherein the keyhole slot is oriented transversely to a longitudinal axis of the first elongate member.

Example 13

The surgical stapler of any of the preceding Examples, wherein the clamp member is moveable from an unclamped position to a clamped position to clamp the first elongate member against the second elongate member, wherein the clamp member includes a latching feature configured to releasably retain the clamp member in the clamped position.

Example 14

The surgical stapler of Example 13, wherein the clamp member comprises a lever, wherein the latching feature comprises a latch member pivotably coupled to a free end of the lever.

Example 15

The surgical stapler of any of the preceding Examples, further comprising a latch member movably coupled to a proximal end of the second elongate member, wherein the latch member is operable to releasably couple the proximal end of the second elongate member with a proximal end of the first elongate member.

Example 16

A surgical stapler comprising: A surgical stapler comprising: (a) a first stapler half comprising: (i) an elongate member having a distal portion that supports an anvil surface, wherein the anvil surface includes a plurality of staple forming pockets, (ii) a shroud, (iii) a keyhole slot arranged in one of the elongate member or the shroud, and (iv) a coupling member, wherein the coupling member extends through the keyhole slot and couples the shroud with the elongate member; and (b) a second stapler half comprising: (i) a distal portion configured to support a staple cartridge, and (ii) a clamp member operable to releasably capture the coupling member to thereby clamp the first stapler half against the second stapler half

Example 17

The surgical stapler of Example 16, wherein the coupling member is configured to rotate relative to the elongate member and the shroud in response to being captured by the clamp member.

Example 18

The surgical stapler of any of Examples 16 through 17, wherein the coupling member comprises a pin, wherein the keyhole slot is configured to constrain the pin laterally relative to the elongate member and the shroud.

Example 19

A surgical stapler comprising: A surgical stapler comprising: (a) a first elongate member having a distal portion that supports an anvil surface, wherein the anvil surface includes a plurality of staple forming pockets; (b) a second elongate member having a distal portion configured to receive a staple cartridge; (c) a clamp lever operable to pivot from a first position to a second position to clamp the first elongate member against the second elongate member; and (d) a latch member coupled to the clamp lever, wherein the latch member is operable to releasably couple a free end of the clamp lever with the second elongate member when the clamp lever is in the second position.

Example 20

The surgical stapler of Example 19, wherein the latch member is configured to pivot relative to the free end of the clamp lever to releasably engage the second elongate member.

Example 21

A surgical stapler comprising: (a) a first elongate member having a distal portion that supports an anvil surface, wherein the anvil surface includes a plurality of staple forming pockets; (b) a second elongate member having a distal portion configured to receive a staple cartridge; (c) a clamp member, wherein the clamp member is moveable from a first position to a second position to releasably clamp the first elongate member against the second elongate member; and (d) a resilient member, wherein the resilient member is configured to urge the distal portion of the first elongate member away from the distal portion of the second elongate member when the clamp member is in the first position.

Example 22

The surgical stapler of Example 21, further comprising a shroud that covers at least a portion of the first elongate member, wherein the resilient member is housed at least partially within the shroud.

Example 23

The surgical stapler of Example 22, wherein the shroud includes a shoulder that projects away from the first elongate member, wherein the resilient member is housed at least partially within an interior of the shoulder.

Example 24

The surgical stapler of any of Examples 22 through 23, wherein an end of the resilient member is fixed relative to the shroud.

Example 25

The surgical stapler of any of Examples 22 through 24, wherein an interior of the shroud includes a post, wherein the resilient member is coupled to the post.

Example 26

The surgical stapler of any of Examples 21 through 25, wherein the resilient member comprises a compression spring.

Example 27

The surgical stapler of any of Examples 21 through 26, wherein the resilient member is supported by the first elongate member, wherein the resilient member is configured to resiliently contact the second elongate member to thereby urge the distal portion of the first elongate member away from the distal portion of the second elongate member.

Example 28

The surgical stapler of Example 27, wherein the second elongate member includes at least one protrusion that extends toward the first elongate member, wherein the resilient member is configured to resiliently contact the at least one protrusion.

Example 29

The surgical stapler of Example 28, wherein the at least one protrusion comprises a pair of tabs.

Example 30

The surgical stapler of any of Examples 21 through 29, wherein a proximal end of the first elongate member is configured to releasably couple with a proximal end of the second elongate member, wherein the resilient member is configured to urge the distal portion of the first elongate member away from the distal portion of the second elongate member while the proximal ends of the first and second elongate members remain coupled together.

IX. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. patent application Ser. No. 15/889,363, entitled "Release Mechanism for Linear Surgical Stapler," filed on Feb. 6, 2018, issued as U.S. Pat. No. 10,631,866 on Apr. 28, 2020; U.S. patent application Ser. No. 15/889,370, entitled "Lockout Assembly for Linear Surgical Stapler," filed on Feb. 6, 2018, issued as U.S. Pat. No. 10,677,818 on Jun. 2, 2020; U.S. patent application Ser. No. 15/889,374, entitled "Features to Align and Close Linear Surgical Stapler"," filed on Feb. 6, 2018, issued as U.S. Pat. No. 10,932,781 on Mar. 3, 2021; U.S. patent application Ser. No. 15/889,376, entitled "Releasable Coupling Features for Proximal Portions of Linear Surgical Stapler," filed on Feb. 6, 2018, issued as U.S. Pat. No. 10,898,197 on Jan. 26, 2021; U.S. patent application Ser. No. 15/889,388, entitled "Firing Lever Assembly for Linear Surgical Stapler," filed on Feb. 6, 2018, issued as U.S. Pat. No. 10,874,398 on Dec. 29, 2020; and/or U.S. patent application Ser. No. 15/889,390, entitled "Clamping Mechanism for Linear Surgical Stapler," filed on Feb. 6, 2018, issued as U.S. Pat. No. 10,687,819 on Jun. 23, 2020. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
    (a) a first elongate body having a distal portion configured to present a first stapling surface;
    (b) a second elongate body configured to releasably couple with the first elongate body and having a distal portion configured to present a second stapling surface, wherein the first and second stapling surfaces are configured to cooperate to clamp and staple tissue with a plurality of staples;
    (c) a clamp coupled with one of the first elongate body or the second elongate body, wherein the clamp is movable relative to the first and second elongate bodies from a first position to a second position to approximate the first and second stapling surfaces for clamping tissue;
    (d) a latch, wherein the latch is coupled with the clamp such that the latch is movable with the clamp between the first and second positions, wherein the latch is operable to releasably retain the clamp in the second position, wherein the latch is selectively rotatable by a user relative to the clamp to release the clamp from the second position and thereby permit the clamp to move toward the first position;
    (e) a firing assembly movable from a home position to a fired position to fire the staples into the clamped tissue; and
    (f) a retainer operable to releasably retain the firing assembly in the home position, wherein the retainer is movable to inhibit actuation of the latch relative to the clamp when the clamp is in the second position and the firing assembly is displaced from the home position,
    wherein the latch is actuatable by the user to release the clamp from the second position only when the firing assembly is retained in the home position by the retainer.

2. The apparatus of claim 1, wherein the clamp comprises a clamp lever pivotably coupled with the second elongate body, wherein the clamp lever is pivotable toward the second elongate body from the first position to the second position.

3. The apparatus of claim 2, wherein a distal portion of the clamp lever is pivotably coupled with the second elongate body, wherein the latch is pivotably coupled to a proximal end of the clamp lever.

4. The apparatus of claim 3, wherein the latch is configured to releasably capture a proximal end of the second elongate body when the clamp lever is in the second position, wherein the latch is selectively actuatable to release the proximal end and permit movement of the clamp lever toward the first position.

5. The apparatus of claim 1, wherein the home position comprises a proximal position and the fired position comprises a distal position.

6. The apparatus of claim 1, wherein the retainer is arranged at a proximal end of one of the first elongate body or the second elongate body.

7. The apparatus of claim 1, wherein the latch is arranged at a proximal end of the clamp, wherein the retainer is arranged at the proximal end of the second elongate body, wherein the distal portion of the second elongate body is configured to support a stapling assembly having a deck that defines the second stapling surface.

8. The apparatus of claim 1, wherein the retainer comprises a first retainer, further comprising
    a second retainer configured to releasably couple a proximal end of the first elongate body with a proximal end of the second elongate body,
    wherein the first and second retainers are movable relative to one another.

9. The apparatus of claim 1, further comprising a spring configured to urge the distal portions of the first and second elongate bodies away from one another when the clamp is in the first position.

10. The apparatus of claim 9, wherein proximal ends of the first and second elongate bodies are configured to pivotably couple with one another about a pivot axis, wherein the spring is located distal to the pivot axis and separately from the clamp.

11. The apparatus of claim 1, wherein one of the first stapling surface or the second stapling surface includes a plurality of openings that house a plurality of staples, wherein the other of the first stapling surface or the second stapling surface includes a plurality of staple forming pockets configured to form the staples when the apparatus is fired.

12. An apparatus comprising:
    (a) a first elongate body having a distal portion configured to present a first stapling surface;
    (b) a second elongate body configured to releasably couple with the first elongate body and having a distal portion configured to present a second stapling surface, wherein the first and second stapling surfaces are configured to cooperate to clamp and staple tissue with a plurality of staples;
    (c) a clamp coupled with one of the first elongate body or the second elongate body, wherein the clamp is movable relative to the first and second elongate bodies from a first position to a second position to approximate the first and second stapling surfaces for clamping tissue;
    (d) a latch rotatably coupled to the clamp and operable to releasably retain the clamp in the second position; and
    (e) a firing assembly, wherein the firing assembly is movable relative to the first and second elongate bodies through a firing stroke from a home position to a fired position to fire the staples into the clamped tissue, and subsequently through a return stroke from the fired position to the home position,
    wherein the latch is configured to operatively couple with the firing assembly such that the latch is rotatably actuatable by a user relative to the clamp to release the clamp from the second position when the firing assembly is in the home position and is non-actuatable by a user relative to the clamp to release the clamp from the second position when the firing assembly is displaced from the home position, wherein when the firing assembly is in the home position the latch is configured to maintain the clamp in the second position until the latch is actuated by the user.

13. The apparatus of claim 12, wherein the latch is coupled with the clamp such that the latch is movable with the clamp between the first and second positions.

14. The apparatus of claim 12, further comprising a retainer configured to releasably retain the firing assembly in the home position, wherein the retainer is configured to inhibit actuation of the latch relative to the clamp when the clamp is in the second position and the firing assembly is located away from the home position.

15. An apparatus comprising:
   (a) a first half having a distal portion configured to present a first stapling surface; and
   (b) a second half configured to releasably couple with the first half, wherein the second half comprises:
      (i) an elongate body having a distal portion configured to present a second stapling surface, wherein the first and second stapling surfaces are configured to cooperate to clamp and staple tissue with a plurality of staples,
      (ii) a clamp lever pivotably coupled with the elongate body, wherein the clamp lever is pivotable toward the elongate body from an open position to a closed position to approximate the first and second stapling surfaces for clamping tissue,
      (iii) a latch rotatably coupled with a proximal end of the clamp lever and rotatable relative to the clamp lever to releasably retain the clamp lever in the closed position, wherein the latch is externally exposed for direct contact and actuation by a user to release the clamp lever from the closed position, and
      (iv) a firing assembly movable from a home position to a fired position to fire the staples into the clamped tissue,
   wherein the latch is rotatably actuatable by the user to release the clamp lever from the closed position when the firing assembly is in the home position,
   wherein the latch is inhibited from releasing the clamp lever from the closed position when the firing assembly is displaced from the home position.

16. The apparatus of claim 15, wherein the latch is configured to releasably capture a proximal end of the elongate body when the clamp lever is in the closed position, wherein the latch is selectively actuatable by the user to release the proximal end and permit movement of the clamp lever toward the open position when the firing assembly is in the home position.

17. The apparatus of claim 1, wherein the latch is externally exposed in each of the first position and the second position of the clamp.

* * * * *